US010588907B2

(12) United States Patent
Grembecka et al.

(10) Patent No.: US 10,588,907 B2
(45) Date of Patent: Mar. 17, 2020

(54) METHODS AND COMPOSITIONS FOR INHIBITING THE INTERACTION OF MENIN WITH MLL PROTEINS

(71) Applicants: KURA ONCOLOGY, INC., San Diego, CA (US); THE REGENTS OF THE UNIVERSITY OF MICHIGAN, Ann Arbor, MI (US)

(72) Inventors: Jolanta Grembecka, Ann Arbor, MI (US); Tomasz Cierpicki, Ann Arbor, MI (US); Dmitry Borkin, Ann Arbor, MI (US); Jonathan Pollock, Ann Arbor, MI (US); Liansheng Li, San Diego, CA (US); Tao Wu, Carlsbad, CA (US); Jun Feng, San Diego, CA (US); Pingda Ren, San Diego, CA (US); Yi Liu, San Diego, CA (US)

(73) Assignees: KURA ONCOLOGY, INC., San Diego, CA (US); THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 15/578,837

(22) PCT Filed: Jun. 3, 2016

(86) PCT No.: PCT/US2016/035869
§ 371 (c)(1),
(2) Date: Dec. 1, 2017

(87) PCT Pub. No.: WO2016/197027
PCT Pub. Date: Dec. 8, 2016

(65) Prior Publication Data
US 2018/0243303 A1 Aug. 30, 2018

Related U.S. Application Data

(60) Provisional application No. 62/171,111, filed on Jun. 4, 2015.

(51) Int. Cl.
C07D 471/04 (2006.01)
C07D 401/14 (2006.01)
A61K 31/519 (2006.01)
A61P 35/02 (2006.01)
A61P 3/10 (2006.01)
A61K 31/5377 (2006.01)
A61K 31/541 (2006.01)

(52) U.S. Cl.
CPC ........ A61K 31/519 (2013.01); A61K 31/5377 (2013.01); A61K 31/541 (2013.01); A61P 3/10 (2018.01); A61P 35/02 (2018.01)

(58) Field of Classification Search
CPC .. C07D 471/04; C07D 401/14; A61K 31/519; A61K 31/517

USPC .......... 544/279, 283; 514/258, 259
See application file for complete search history.

(56) References Cited

U.S. PATENT DOCUMENTS

| | | | |
|---|---|---|---|
| 5,445,764 A | 8/1995 | Poetsch et al. | |
| 5,861,510 A | 1/1999 | Piscopio et al. | |
| 5,863,949 A | 1/1999 | Robinson et al. | |
| 5,866,562 A * | 2/1999 | Schohe-Loop .... | A61K 31/4709 514/183 |
| 6,849,638 B2 | 2/2005 | Stolle et al. | |
| 7,030,240 B2 | 4/2006 | Dhanoa et al. | |
| 7,744,968 B2 | 6/2010 | Reiffenrath et al. | |
| 8,207,174 B2 | 6/2012 | Tasler et al. | |
| 8,507,491 B2 * | 8/2013 | Cheng .................... | A61K 31/47 514/252.04 |
| 8,993,552 B2 | 3/2015 | Grembecka et al. | |
| 9,216,993 B2 | 12/2015 | Grembecka et al. | |
| 9,505,781 B2 | 11/2016 | Grembecka et al. | |
| 9,505,782 B2 | 11/2016 | Grembecka et al. | |
| 10,077,271 B2 | 9/2018 | Grembecka et al. | |
| 2003/0119829 A1 | 6/2003 | Stolle et al. | |
| 2003/0153556 A1 | 8/2003 | Levy et al. | |
| 2005/0123906 A1 | 6/2005 | Rana | |
| 2005/0222175 A1 | 10/2005 | Dhanoa et al. | |
| 2005/0222176 A1 | 10/2005 | Dhanoa et al. | |
| 2006/0025406 A1 | 2/2006 | Zembower et al. | |
| 2006/0281769 A1 | 12/2006 | Baumann et al. | |
| 2006/0281771 A1 | 12/2006 | Baumann et al. | |
| 2007/0078133 A1 | 4/2007 | Liu et al. | |

(Continued)

FOREIGN PATENT DOCUMENTS

| | | |
|---|---|---|
| EP | 1382603 A1 | 1/2004 |
| JP | H10330377 A | 12/1998 |

(Continued)

OTHER PUBLICATIONS

Agarwal, et al. Menin molecular interactions: insights into normal functions and tumorigenesis. Horm Matab Res, 37(6), pp. 369-374 (2005).

(Continued)

Primary Examiner — Charanjit Aulakh
(74) Attorney, Agent, or Firm — Wilson Sonsini Goodrich & Rosati

(57) ABSTRACT

The present disclosure provides compositions and methods of use to inhibit the interaction of menin with MLL1, MLL2 and MLL-fusion oncoproteins. The compositions and methods of use are useful for the treatment of leukemia, solid cancers, diabetes and other diseases dependent on activity of MLL1, MLL2, MLL fusion proteins, and/or menin.

1 Claim, 3 Drawing Sheets
Specification includes a Sequence Listing.

(56) References Cited

U.S. PATENT DOCUMENTS

| | | |
|---|---|---|
| 2008/0249114 A1 | 10/2008 | Tasler et al. |
| 2008/0293699 A1 | 11/2008 | Reed et al. |
| 2009/0163545 A1 | 6/2009 | Goldfarb |
| 2009/0298772 A1 | 12/2009 | Thirman |
| 2010/0063047 A1 | 3/2010 | Borchardt et al. |
| 2011/0065690 A1 | 3/2011 | Grembecka et al. |
| 2012/0322742 A1 | 12/2012 | Thirman |
| 2013/0210831 A1* | 8/2013 | Su et al. ............. C07D 487/04 544/280 |
| 2014/0275070 A1 | 9/2014 | Grembecka et al. |
| 2014/0371239 A1 | 12/2014 | Grembecka et al. |
| 2016/0045504 A1 | 2/2016 | Grembecka et al. |
| 2016/0046647 A1 | 2/2016 | Grembecka et al. |
| 2017/0247391 A1 | 8/2017 | Grembecka et al. |
| 2017/0253611 A1 | 9/2017 | Grembecka et al. |
| 2018/0105531 A1 | 4/2018 | Grembecka et al. |

FOREIGN PATENT DOCUMENTS

| | | |
|---|---|---|
| JP | 2009507004 A | 2/2009 |
| JP | 2013503906 A | 2/2013 |
| WO | WO-9633172 A1 | 10/1996 |
| WO | WO-9834915 A1 | 8/1998 |
| WO | WO-9943675 A1 | 9/1999 |
| WO | WO-9965909 A1 | 12/1999 |
| WO | WO-02088138 A1 | 11/2002 |
| WO | WO-03022214 A2 | 3/2003 |
| WO | WO-2004030671 A2 | 4/2004 |
| WO | WO-2004030672 A1 | 4/2004 |
| WO | WO-2005020897 A2 | 3/2005 |
| WO | WO-2006135630 A1 | 12/2006 |
| WO | WO-2006135636 A2 | 12/2006 |
| WO | WO-2007026024 A2 | 3/2007 |
| WO | WO-2007042669 A2 | 4/2007 |
| WO | WO-2007076034 A2 | 7/2007 |
| WO | WO-2007115822 A1 | 10/2007 |
| WO | WO-2008070303 A2 | 6/2008 |
| WO | WO-2008090140 A1 | 7/2008 |
| WO | WO-2008099019 A1 | 8/2008 |
| WO | WO-2008107320 A1 | 9/2008 |
| WO | WO-2008114275 A2 | 9/2008 |
| WO | WO-2008135232 A1 | 11/2008 |
| WO | WO-2009017838 A2 | 2/2009 |
| WO | WO-2009064388 A2 | 5/2009 |
| WO | WO-2009143058 A1 | 11/2009 |
| WO | WO-2010030757 A2 | 3/2010 |
| WO | WO-2011003418 A1 | 1/2011 |
| WO | WO-2011029054 A1 | 3/2011 |
| WO | WO-2011101069 A2 | 8/2011 |
| WO | WO-2013024291 A2 | 2/2013 |
| WO | WO-2013072694 A1 | 5/2013 |
| WO | WO-2014164543 A1 | 10/2014 |
| WO | WO-2015154039 A2 | 10/2015 |
| WO | WO-2015191701 A1 | 12/2015 |
| WO | WO-2016040330 A1 | 3/2016 |
| WO | WO-2016195776 A1 | 12/2016 |
| WO | WO-2016197027 A1 | 12/2016 |
| WO | WO-2017112768 A1 | 6/2017 |
| WO | WO-2017132398 A1 | 8/2017 |
| WO | WO-2017161002 A1 | 9/2017 |
| WO | WO-2017161028 A1 | 9/2017 |
| WO | WO-2017192543 A1 | 11/2017 |
| WO | WO-2017207387 A1 | 12/2017 |
| WO | WO-2017214367 A1 | 12/2017 |
| WO | WO-2018024602 A1 | 2/2018 |
| WO | WO-2018050684 A1 | 3/2018 |
| WO | WO-2018050686 A1 | 3/2018 |
| WO | WO-2018053267 A1 | 3/2018 |

OTHER PUBLICATIONS

Arkin et al. Small-molecule inhibitors of protein-protein interactions: progressing toward the reality. Chem Biol. 21(9):1102-1114 (2014).

Bhaskar, et al. Synthesis, Antimicrobial and Antihyperlipidemic Activities of Some 4-Substituted-5,6,7,8-tetrhydrol. Asian J Chemistry 2007, 19(7):5187-5194.

Borkin et al. Pharmacologic inhibition of the Menin-MLL interaction blocks progression of MLL leukemia in vivo. Cancer Cell. Apr. 13, 2015;27(4):589-602. doi: 10.1016/j.ccell.2015.02.016. Epub Mar. 26, 2015.

Borkin et al. Property Focused Structure-Based Optimization of Small Molecule Inhibitors of the Protein-Protein Interaction between Menin and Mixed Lineage Leukemia (MLL). J Med Chem. Feb. 11, 2016;59(3):892-913.

Chen, et al. The tumor suppressor menin regulates hematopoiesis and myeloid transformation by influencing Hox gene expression. Proc Natl Acad Sci USA, 103(4), pp. 1018-1023 (2006).

Cox, et al. Chromosomal aberration of the 11q23 locus in acute leukemia and frequency of MLL gene translocation: results in 378 adult patients. Am J Clin Pathol, 122(2), pp. 298-306 (2004).

Eguchi, et al. The role of the MLL gene in infant leukemia. Int J Hematol, 78(5), pp. 390-401 (2003).

F1174-09147, Pubchem, http://pubchem.ncbi.nlm.nih.gov/summary/summary.cgi?cid=711090, 2007, 13 pages.

Grembecka, et al. Menin-MLL inhibitors reverse oncogenic activity of MLL fusion proteins in leukemia. Nature Chemical Biology. 2012 No. 8. pp. 277-284.

International Search Report and Written Opinion dated Sep. 1, 2016 for International PCT Patent Application No. PCT/US2016/035869.

Kim, et al. Chemical Biology Investigation of Cell Death Pathways Activated by Endoplasmic Reticulum Stress Cytoprotective Modulators of ASK1. J Biological Chemistry Jan. 2009, 284(3):1593-1603.

Marx, Stephen J. Molecular genetics of multiple endocrine neoplasia types 1 and 2. Nat Rev Cancer, 5(5), pp. 367-375 (2005).

Mayer, et al. Group epitope mapping by saturation transfer difference NMR to identify segments of a ligand in direct contact with a protein receptor. J Am Chem Soc, 123(25), pp. 6108-6117 (2001).

Mosmann, et al. Rapid colorimetric assay for cellular growth and survival: application to proliferation and cytotoxicity assays. J Immunol Methods, 65, (1-2), pp. 55-63 (1983).

Nairn, J.G. Solutions, Emulsions, Suspensions and Extracts. Chapter 83 of Remington's Pharmaceutical Sciences. 18th Ed. Gennaro, Alfonso R. Mack Publishing Company, Pennsylvania. 1990. 35 pages.

National Center for Biotechnology Information. PubChem Substance Database; SID=25433807, https://pubchem.ncbi.nlm.nih.gov/substance/25433807, deposit date Jul. 30, 2007.

Pollock et al. Rational Design of Orthogonal Multipolar Interactions with Fluorine in Protein-Ligand Complexes. J Med Chem. Sep. 24, 2015;58(18):7465-74.

Pubchem CID 88912571. Create Date: Feb. 13, 2015. Date Accessed: Jul. 10, 2017; p. 4, compound listed.

Sharma, et al. Synthesis of Thienopyrimidines and their Antipsychotic Activity. E Journal of Chemistry. 2010. 7(2):655-664.

Shi, et al. Structural insights into inhibition of the bivalent menin-MLL interaction by small molecules in leukemia. Blood. Nov. 29, 2012;120(23):4461-9.

Slany, Robert K. The molecular biology of mixed lineage leukemia. Haematologica. 94(7), pp. 984-993 (2009).

Slany, Robert K. When epigenetics kills: MLL fusion proteins in leukemia. Hematol Oncol, 23(1), pp. 1-9 (2005).

SMR00018765, Pubchem, http://pubchem.ncbi.nlm.nih.gov/summary/summary.cgi?cid=1323703, 2007, 16 pages.

Sorensen, et al. Molecular rearrangements of the MLL gene are present in most cases of infant acute myeloid leukemia and are strongly correlated with monocytic or myelomonocytic phenotypes. J Clin Invest, 93(1), pp. 429-437 (1994).

Yokoyama, et al. The menin tumor suppressor protein is an essential oncogenic cofactor for MLL-associated leukemogenesis. Cell, 123(2), pp. 207-218 (2005).

AC1MFIB7, Pubchem, [Online], 2005, [searched on Mar. 29, 2016], Internet< url,< a="" href="https://pubchem.ncbi.nlm.nih.gov/compounds/2894865#section=Top">https://pubchem.ncbi.nlm.nih.gov/compounds/2894865#section=Top</url,>.

(56) References Cited

OTHER PUBLICATIONS

AC1N5DGQ, PubChem, [Online], 2005, [searched on Mar. 29, 2016], Internet< url,< a="" href="https://pubchem.ncbi.nlm.nih.gov/compound/4143243">https://pubchem.ncbi.nlm.nih.gov/compound/4143243</url,>.

Arkin, et al. Small-molecule inhibitors of protein-protein interactions: progressing toward the reality. Chem Biol. Sep. 18, 2014;21(9):1102-14. doi: 10.1016/j.chembiol.2014.09.001.

Blackburn, et al. Identification and characterization of aminopiperidinequinolones and quinazolinones as MCHr1 antagonists. Bioorg Med Chem Lett. May 15, 2006;16(10):2621-7. Epub Mar. 9, 2006.

Co-pending U.S. Appl. No. 16/082,649, filed Sep. 6, 2018.

Co-pending U.S. Appl. No. 16/185,673, filed Nov. 9, 2018.

European search report with written opinion dated Oct. 19, 2018 for EP Application No. 16804583.

Kym, et al. Screening for cardiovascular safety: a structure-activity approach for guiding lead selection of melanin concentrating hormone receptor 1 antagonists. J Med Chem. Apr. 6, 2006;49(7):2339-52.

Pubchem. CID 10631635. Oct. 25, 2006, pp. 1-12.

Pubchem. CID10614048. Oct. 25, 2006, pp. 1-9. Retrieved from the Internet< url:<ahref="https://pubchem.ncbi.nlm.nih.gov/compound/10614048">https://pubchem.ncbi.nlm.nih.gov/compound/10614048.</url:<a>.

\* cited by examiner

FIG. 1

Amino acid sequence of human menin, isoform 1 (SEQ ID NO: 1):

```
MGLKAAQKTLFPLRSIDDVVRLFAAELGREEPDLVLLSLVLGFVEHFLAVNRVIPTNVPE
LTFQPSPAPDPPGGLTYFPVADLSIIAALYARFTAQIRGAVDLSLYPREGGVSSRELVKK
VSDVIWNSLSRSYFKDRAHIQSLFSFITGWSPVGTKLDSSGVAFAVVGACQALGLRDVHL
ALSEDHAWVVFGPNGEQTAEVTWHGKGNEDRRGQTVNAGVAERSWLYLKGSYMRCDRKME
VAFMVCAINPSIDLHTDSLELLQLQQKLLWLLYDLGHLERYPMALGNLADLEELEPTPGR
PDPLTLYHKGIASAKTYYRDEHIYPYMYLAGYHCRNRNVREALQAWADTATVIQDYNYCR
EDEEIYKEFFEVANDVIPNLLKEAASLLEAGEERPGEQSQGTQSQGSALQDPECFAHLLR
FYDGICKWEEGSPTPVLHVGWATFLVQSLGRFEGQVRQKVRIVSREAEAAEAEEPWGEEA
REGRRRGPRRESKPEEPPPPKKPALDKGLGTGQGAVSGPPRKPPGTVAGTARGPEGGSTA
QVPAPTASPPPEGPVLTFQSEKMKGMKELLVATKINSSAIKLQLTAQSQVQMKKQKVSTP
SDYTLSFLKRQRKGL
```

FIG. 2

Amino acid sequence of human menin, isoform 2 (SEQ ID NO: 2):

```
MGLKAAQKTLFPLRSIDDVVRLFAAELGREEPDLVLLSLVLGFVEHFLAVNRVIPTNVPE
LTFQPSPAPDPPGGLTYFPVADLSIIAALYARFTAQIRGAVDLSLYPREGGVSSRELVKK
VSDVIWNSLSRSYFKDRAHIQSLFSFITGTKLDSSGVAFAVVGACQALGLRDVHLALSED
HAWVVFGPNGEQTAEVTWHGKGNEDRRGQTVNAGVAERSWLYLKGSYMRCDRKMEVAFMV
CAINPSIDLHTDSLELLQLQQKLLWLLYDLGHLERYPMALGNLADLEELEPTPGRPDPLT
LYHKGIASAKTYYRDEHIYPYMYLAGYHCRNRNVREALQAWADTATVIQDYNYCREDEEI
YKEFFEVANDVIPNLLKEAASLLEAGEERPGEQSQGTQSQGSALQDPECFAHLLRFYDGI
CKWEEGSPTPVLHVGWATFLVQSLGRFEGQVRQKVRIVSREAEAAEAEEPWGEEAREGRR
RGPRRESKPEEPPPPKKPALDKGLGTGQGAVSGPPRKPPGTVAGTARGPEGGSTAQVPAP
TASPPPEGPVLTFQSEKMKGMKELLVATKINSSAIKLQLTAQSQVQMKKQKVSTPSDYTL
SFLKRQRKGL
```

FIG. 3

Amino acid sequence of human menin, isoform 3 (SEQ ID NO: 3):

MGLKAAQKTLFPLRSIDDVVRLFAAELGREEPDLVLLSLVLGFVEHFLAVNRVIPTNVPE
LTFQPSPAPDPPGGLTYFPVADLSIIAALYARFTAQIRGAVDLSLYPREGGVSSRELVKK
VSDVIWNSLSRSYFKDRAHIQSLFSFITGTKLDSSGVAFAVVGACQALGLRDVHLALSED
HAWSWLYLKGSYMRCDRKMEVAFMVCAINPSIDLHTDSLELLQLQQKLLWLLYDLGHLER
YPMALGNLADLEELEPTPGRPDPLTLYHKGIASAKTYYRDEHIYPYMYLAGYHCRNRNVR
EALQAWADTATVIQDYNYCREDEEIYKEFFEVANDVIPNLLKEAASLLEAGEERPGEQSQ
GTQSQGSALQDPECFAHLLRFYDGICKWEEGSPTPVLHVGWATFLVQSLGRFEGQVRQKV
RIVSREAEAAEAEEPWGEEAREGRRRGPRRESKPEEPPPPKKPALDKGLGTGQGAVSGPP
RKPPGTVAGTARGPEGGSTAQVPAPTASPPPEGPVLTFQSEKMKGMKELLVATKINSSAI
KLQLTAQSQVQMKKQKVSTPSDYTLSFLKRQRKGL

SEQUENCE LISTING

<160> NUMBER OF SEQ ID NOS: 3

<210> SEQ ID NO 1
<211> LENGTH: 615
<212> TYPE: PRT
<213> ORGANISM: Homo sapiens

<400> SEQUENCE: 1

```
Met Gly Leu Lys Ala Ala Gln Lys Thr Leu Phe Pro Leu Arg Ser Ile
1               5                   10                  15

Asp Asp Val Val Arg Leu Phe Ala Ala Glu Leu Gly Arg Glu Glu Pro
            20                  25                  30

Asp Leu Val Leu Leu Ser Leu Val Leu Gly Phe Val Glu His Phe Leu
        35                  40                  45

Ala Val Asn Arg Val Ile Pro Thr Asn Val Pro Glu Leu Thr Phe Gln
    50                  55                  60

Pro Ser Pro Ala Pro Asp Pro Pro Gly Gly Leu Thr Tyr Phe Pro Val
65                  70                  75                  80

Ala Asp Leu Ser Ile Ile Ala Ala Leu Tyr Ala Arg Phe Thr Ala Gln
                85                  90                  95

Ile Arg Gly Ala Val Asp Leu Ser Leu Tyr Pro Arg Glu Gly Gly Val
            100                 105                 110

Ser Ser Arg Glu Leu Val Lys Lys Val Ser Asp Val Ile Trp Asn Ser
        115                 120                 125

Leu Ser Arg Ser Tyr Phe Lys Asp Arg Ala His Ile Gln Ser Leu Phe
    130                 135                 140

Ser Phe Ile Thr Gly Trp Ser Pro Val Gly Thr Lys Leu Asp Ser Ser
145                 150                 155                 160
```

-continued

```
Gly Val Ala Phe Ala Val Gly Ala Cys Gln Ala Leu Gly Leu Arg
            165                 170                 175

Asp Val His Leu Ala Leu Ser Glu Asp His Ala Trp Val Val Phe Gly
        180                 185                 190

Pro Asn Gly Glu Gln Thr Ala Glu Val Thr Trp His Gly Lys Gly Asn
        195                 200                 205

Glu Asp Arg Arg Gly Gln Thr Val Asn Ala Gly Val Ala Glu Arg Ser
        210                 215                 220

Trp Leu Tyr Leu Lys Gly Ser Tyr Met Arg Cys Asp Arg Lys Met Glu
225                 230                 235                 240

Val Ala Phe Met Val Cys Ala Ile Asn Pro Ser Ile Asp Leu His Thr
                245                 250                 255

Asp Ser Leu Glu Leu Leu Gln Leu Gln Gln Lys Leu Leu Trp Leu Leu
            260                 265                 270

Tyr Asp Leu Gly His Leu Glu Arg Tyr Pro Met Ala Leu Gly Asn Leu
        275                 280                 285

Ala Asp Leu Glu Glu Leu Glu Pro Thr Pro Gly Arg Pro Asp Pro Leu
        290                 295                 300

Thr Leu Tyr His Lys Gly Ile Ala Ser Ala Lys Thr Tyr Tyr Arg Asp
305                 310                 315                 320

Glu His Ile Tyr Pro Tyr Met Tyr Leu Ala Gly Tyr His Cys Arg Asn
                325                 330                 335

Arg Asn Val Arg Glu Ala Leu Gln Ala Trp Ala Asp Thr Ala Thr Val
            340                 345                 350

Ile Gln Asp Tyr Asn Tyr Cys Arg Glu Asp Glu Ile Tyr Lys Glu
        355                 360                 365

Phe Phe Glu Val Ala Asn Asp Val Ile Pro Asn Leu Leu Lys Glu Ala
    370                 375                 380

Ala Ser Leu Leu Glu Ala Gly Glu Arg Pro Gly Glu Gln Ser Gln
385                 390                 395                 400

Gly Thr Gln Ser Gln Gly Ser Ala Leu Gln Asp Pro Glu Cys Phe Ala
                405                 410                 415

His Leu Leu Arg Phe Tyr Asp Gly Ile Cys Lys Trp Glu Glu Gly Ser
            420                 425                 430

Pro Thr Pro Val Leu His Val Gly Trp Ala Thr Phe Leu Val Gln Ser
        435                 440                 445

Leu Gly Arg Phe Glu Gly Gln Val Arg Gln Lys Val Arg Ile Val Ser
    450                 455                 460

Arg Glu Ala Glu Ala Ala Glu Ala Glu Pro Trp Gly Glu Ala
465                 470                 475                 480

Arg Glu Gly Arg Arg Gly Pro Arg Arg Glu Ser Lys Pro Glu Glu
                485                 490                 495

Pro Pro Pro Pro Lys Lys Pro Ala Leu Asp Lys Gly Leu Gly Thr Gly
            500                 505                 510

Gln Gly Ala Val Ser Gly Pro Arg Lys Pro Pro Gly Thr Val Ala
        515                 520                 525

Gly Thr Ala Arg Gly Pro Glu Gly Gly Ser Thr Ala Gln Val Pro Ala
    530                 535                 540

Pro Thr Ala Ser Pro Pro Glu Gly Pro Val Leu Thr Phe Gln Ser
545                 550                 555                 560

Glu Lys Met Lys Gly Met Lys Glu Leu Leu Val Ala Thr Lys Ile Asn
                565                 570                 575

Ser Ser Ala Ile Lys Leu Gln Leu Thr Ala Gln Ser Gln Val Gln Met
```

```
            580                 585                 590
Lys Lys Gln Lys Val Ser Thr Pro Ser Asp Tyr Thr Leu Ser Phe Leu
            595                 600                 605

Lys Arg Gln Arg Lys Gly Leu
            610                 615

<210> SEQ ID NO 2
<211> LENGTH: 610
<212> TYPE: PRT
<213> ORGANISM: Homo sapiens

<400> SEQUENCE: 2

Met Gly Leu Lys Ala Ala Gln Lys Thr Leu Phe Pro Leu Arg Ser Ile
1               5                   10                  15

Asp Asp Val Val Arg Leu Phe Ala Ala Glu Leu Gly Arg Glu Glu Pro
            20                  25                  30

Asp Leu Val Leu Leu Ser Leu Val Leu Gly Phe Val Glu His Phe Leu
        35                  40                  45

Ala Val Asn Arg Val Ile Pro Thr Asn Val Pro Glu Leu Thr Phe Gln
    50                  55                  60

Pro Ser Pro Ala Pro Asp Pro Pro Gly Gly Leu Thr Tyr Phe Pro Val
65                  70                  75                  80

Ala Asp Leu Ser Ile Ile Ala Ala Leu Tyr Ala Arg Phe Thr Ala Gln
                85                  90                  95

Ile Arg Gly Ala Val Asp Leu Ser Leu Tyr Pro Arg Glu Gly Gly Val
            100                 105                 110

Ser Ser Arg Glu Leu Val Lys Lys Val Ser Asp Val Ile Trp Asn Ser
        115                 120                 125

Leu Ser Arg Ser Tyr Phe Lys Asp Arg Ala His Ile Gln Ser Leu Phe
    130                 135                 140

Ser Phe Ile Thr Gly Thr Lys Leu Asp Ser Ser Gly Val Ala Phe Ala
145                 150                 155                 160

Val Val Gly Ala Cys Gln Ala Leu Gly Leu Arg Asp Val His Leu Ala
                165                 170                 175

Leu Ser Glu Asp His Ala Trp Val Val Phe Gly Pro Asn Gly Glu Gln
            180                 185                 190

Thr Ala Glu Val Thr Trp His Gly Lys Gly Asn Glu Asp Arg Arg Gly
        195                 200                 205

Gln Thr Val Asn Ala Gly Val Ala Glu Arg Ser Trp Leu Tyr Leu Lys
    210                 215                 220

Gly Ser Tyr Met Arg Cys Asp Arg Lys Met Glu Val Ala Phe Met Val
225                 230                 235                 240

Cys Ala Ile Asn Pro Ser Ile Asp Leu His Thr Asp Ser Leu Glu Leu
                245                 250                 255

Leu Gln Leu Gln Gln Lys Leu Leu Trp Leu Leu Tyr Asp Leu Gly His
            260                 265                 270

Leu Glu Arg Tyr Pro Met Ala Leu Gly Asn Leu Ala Asp Leu Glu Glu
        275                 280                 285

Leu Glu Pro Thr Pro Gly Arg Pro Asp Pro Leu Thr Leu Tyr His Lys
    290                 295                 300

Gly Ile Ala Ser Ala Lys Thr Tyr Tyr Arg Asp Glu His Ile Tyr Pro
305                 310                 315                 320

Tyr Met Tyr Leu Ala Gly Tyr His Cys Arg Asn Arg Asn Val Arg Glu
                325                 330                 335
```

```
Ala Leu Gln Ala Trp Ala Asp Thr Ala Thr Val Ile Gln Asp Tyr Asn
            340                 345                 350

Tyr Cys Arg Glu Asp Glu Ile Tyr Lys Glu Phe Phe Glu Val Ala
        355                 360                 365

Asn Asp Val Ile Pro Asn Leu Leu Lys Glu Ala Ala Ser Leu Leu Glu
    370                 375                 380

Ala Gly Glu Glu Arg Pro Gly Glu Gln Ser Gln Gly Thr Gln Ser Gln
385                 390                 395                 400

Gly Ser Ala Leu Gln Asp Pro Glu Cys Phe Ala His Leu Leu Arg Phe
                405                 410                 415

Tyr Asp Gly Ile Cys Lys Trp Glu Glu Gly Ser Pro Thr Pro Val Leu
            420                 425                 430

His Val Gly Trp Ala Thr Phe Leu Val Gln Ser Leu Gly Arg Phe Glu
            435                 440                 445

Gly Gln Val Arg Gln Lys Val Arg Ile Val Ser Arg Glu Ala Glu Ala
        450                 455                 460

Ala Glu Ala Glu Pro Trp Gly Glu Ala Arg Glu Gly Arg Arg
465                 470                 475                 480

Arg Gly Pro Arg Arg Glu Ser Lys Pro Glu Glu Pro Pro Pro Lys
            485                 490                 495

Lys Pro Ala Leu Asp Lys Gly Leu Gly Thr Gly Gln Gly Ala Val Ser
            500                 505                 510

Gly Pro Pro Arg Lys Pro Pro Gly Thr Val Ala Gly Thr Ala Arg Gly
            515                 520                 525

Pro Glu Gly Gly Ser Thr Ala Gln Val Pro Ala Pro Thr Ala Ser Pro
530                 535                 540

Pro Pro Glu Gly Pro Val Leu Thr Phe Gln Ser Glu Lys Met Lys Gly
545                 550                 555                 560

Met Lys Glu Leu Leu Val Ala Thr Lys Ile Asn Ser Ser Ala Ile Lys
            565                 570                 575

Leu Gln Leu Thr Ala Gln Ser Gln Val Gln Met Lys Lys Gln Lys Val
            580                 585                 590

Ser Thr Pro Ser Asp Tyr Thr Leu Ser Phe Leu Lys Arg Gln Arg Lys
            595                 600                 605

Gly Leu
    610

<210> SEQ ID NO 3
<211> LENGTH: 575
<212> TYPE: PRT
<213> ORGANISM: Homo sapiens

<400> SEQUENCE: 3

Met Gly Leu Lys Ala Ala Gln Lys Thr Leu Phe Pro Leu Arg Ser Ile
1               5                   10                  15

Asp Asp Val Val Arg Leu Phe Ala Ala Glu Leu Gly Arg Glu Glu Pro
            20                  25                  30

Asp Leu Val Leu Leu Ser Leu Val Leu Gly Phe Val Glu His Phe Leu
        35                  40                  45

Ala Val Asn Arg Val Ile Pro Thr Asn Val Pro Glu Leu Thr Phe Gln
    50                  55                  60

Pro Ser Pro Ala Pro Asp Pro Pro Gly Gly Leu Thr Tyr Phe Pro Val
65                  70                  75                  80

Ala Asp Leu Ser Ile Ile Ala Ala Leu Tyr Ala Arg Phe Thr Ala Gln
            85                  90                  95
```

```
Ile Arg Gly Ala Val Asp Leu Ser Leu Tyr Pro Arg Glu Gly Val
            100                 105                 110

Ser Ser Arg Glu Leu Val Lys Lys Val Ser Asp Val Ile Trp Asn Ser
        115                 120                 125

Leu Ser Arg Ser Tyr Phe Lys Asp Arg Ala His Ile Gln Ser Leu Phe
        130                 135                 140

Ser Phe Ile Thr Gly Thr Lys Leu Asp Ser Ser Gly Val Ala Phe Ala
145                 150                 155                 160

Val Val Gly Ala Cys Gln Ala Leu Gly Leu Arg Asp Val His Leu Ala
                165                 170                 175

Leu Ser Glu Asp His Ala Trp Ser Trp Leu Tyr Leu Lys Gly Ser Tyr
            180                 185                 190

Met Arg Cys Asp Arg Lys Met Glu Val Ala Phe Met Val Cys Ala Ile
        195                 200                 205

Asn Pro Ser Ile Asp Leu His Thr Asp Ser Leu Glu Leu Leu Gln Leu
        210                 215                 220

Gln Gln Lys Leu Leu Trp Leu Leu Tyr Asp Leu Gly His Leu Glu Arg
225                 230                 235                 240

Tyr Pro Met Ala Leu Gly Asn Leu Ala Asp Leu Glu Glu Leu Glu Pro
                245                 250                 255

Thr Pro Gly Arg Pro Asp Pro Leu Thr Leu Tyr His Lys Gly Ile Ala
            260                 265                 270

Ser Ala Lys Thr Tyr Tyr Arg Asp Glu His Ile Tyr Pro Tyr Met Tyr
        275                 280                 285

Leu Ala Gly Tyr His Cys Arg Asn Arg Asn Val Arg Glu Ala Leu Gln
        290                 295                 300

Ala Trp Ala Asp Thr Ala Thr Val Ile Gln Asp Tyr Asn Tyr Cys Arg
305                 310                 315                 320

Glu Asp Glu Glu Ile Tyr Lys Glu Phe Phe Glu Val Ala Asn Asp Val
                325                 330                 335

Ile Pro Asn Leu Leu Lys Glu Ala Ala Ser Leu Leu Glu Ala Gly Glu
            340                 345                 350

Glu Arg Pro Gly Glu Gln Ser Gln Gly Thr Gln Ser Gln Gly Ser Ala
        355                 360                 365

Leu Gln Asp Pro Glu Cys Phe Ala His Leu Leu Arg Phe Tyr Asp Gly
        370                 375                 380

Ile Cys Lys Trp Glu Glu Gly Ser Pro Thr Pro Val Leu His Val Gly
385                 390                 395                 400

Trp Ala Thr Phe Leu Val Gln Ser Leu Gly Arg Phe Glu Gly Gln Val
                405                 410                 415

Arg Gln Lys Val Arg Ile Val Ser Arg Glu Ala Glu Ala Ala Glu Ala
            420                 425                 430

Glu Glu Pro Trp Gly Glu Glu Ala Arg Glu Gly Arg Arg Gly Pro
        435                 440                 445

Arg Arg Glu Ser Lys Pro Glu Glu Pro Pro Pro Lys Lys Pro Ala
450                 455                 460

Leu Asp Lys Gly Leu Gly Thr Gly Gln Gly Ala Val Ser Gly Pro Pro
465                 470                 475                 480

Arg Lys Pro Pro Gly Thr Val Ala Gly Thr Ala Arg Gly Pro Glu Gly
                485                 490                 495

Gly Ser Thr Ala Gln Val Pro Ala Pro Thr Ala Ser Pro Pro Pro Glu
            500                 505                 510
```

METHODS AND COMPOSITIONS FOR INHIBITING THE INTERACTION OF MENIN WITH MLL PROTEINS

CROSS-REFERENCE

This application is a National Stage Entry of PCT/US2016/035869, filed Jun. 3, 2016, which claims the benefit of U.S. Provisional Application No. 62/171,111, filed Jun. 4, 2015, each incorporated herein by reference.

BACKGROUND OF THE INVENTION

The mixed-lineage leukemia (MLL) protein is a histone methyltransferase critical for the epigenetic regulation of gene transcription. Many acute leukemias, including acute myeloblastic leukemia (AML), acute lymphoblastic leukemia (ALL) and mixed-lineage leukemia (MLL), are characterized by the presence of chimeric MLL fusion proteins that result from chromosomal translocations of the MLL gene located at chromosome 11, band q23 (11q23). Chimeric MLL fusion proteins retain approximately 1,400 amino acids of the N-terminus of MLL, but are fused with one of approximately 80 partner proteins (e.g., AF4, AF9, ENL, AF10, ELL, AF6, AF1p, GAS7). MLL fusion proteins lack the original histone methyltransferase activity of the C-terminus of MLL and gain the ability to regulate transcription of numerous oncogenes, including HOX and MEIS1, resulting in increased cell proliferation and decreased cell differentiation, ultimately leading to leukemogenesis.

The menin protein, which is encoded by the Multiple Endocrine Neoplasia (MEN) gene, is a ubiquitously expressed nuclear protein that engages in interactions with DNA processing and repair proteins, chromatin modifying proteins and numerous transcription factors (Agarwal, et al.; Horm Metab Res, 2005, 37(6): 369-374). The association of menin with the N-terminus of MLL fusion proteins is necessary for the observed oncogenic activity of MLL fusion proteins. This association has been shown to constitutively up-regulate the expression of HOX and MEIS1 oncogenes and impairs proliferation and differentiation of hematopoietic cells leading to leukemia development. Since menin has been shown to function as a general oncogenic cofactor in MLL-related leukemias, the interaction between menin and MLL fusion proteins and MLL represents a potential chemotherapeutic target.

Patients, especially infants, with leukemias harboring chromosomal translocations of the MLL gene have a dismal prognosis, with less than a 40% five year survival rate (Slany; *Haematologica*, 2009, 94(7): 984-993). A novel therapeutic strategy is urgently needed to treat these leukemias. Small molecule inhibitors that block the menin-MLL interaction are thus valuable targets for treating diseases involving the MLL fusion proteins.

SUMMARY OF THE INVENTION

The present disclosure addresses a need in the art by providing compositions and methods for inhibiting the protein-protein interaction of menin with MLL1, MLL2 and MLL-fusion oncoproteins. The compositions and methods herein may be useful for treating diseases dependent on the activity of MLL1, MLL2, MLL fusion proteins, and/or menin such as leukemia, solid cancers, and diabetes. In certain embodiments, a compound of the disclosure interacts non-covalently with menin and inhibits the interaction of menin with MLL. In certain embodiments, a compound of the disclosure covalently binds menin and inhibits the interaction of menin with MLL.

In some embodiments of a compound provided herein, the compound non-covalently or covalently binds to any one or more isoforms of menin, for example, isoform 1 (SEQ ID NO: 1), isoform 2 (SEQ ID NO: 2) or isoform 3 (SEQ ID NO: 3) of menin. In certain embodiments, the menin protein shares 60% or more, 70% or more, 75% or more, 80% or more, 85% or more, 90% or more, 95% or more, or 99% or more sequence identity with isoform 1 (SEQ ID NO: 1), isoform 2 (SEQ ID NO: 2) or isoform 3 (SEQ ID NO: 3).

In one aspect, the present disclosure provides a compound of Formula VII:

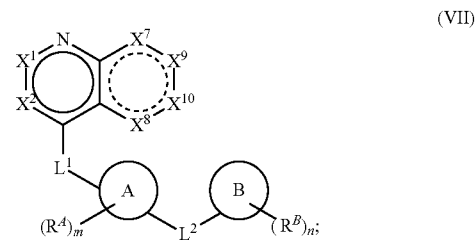

(VII)

or a pharmaceutically acceptable salt thereof, wherein:
each of $X^1$ and $X^2$ is independently $CR^2$ or N;
each of $X^7$, $X^8$, $X^9$, and $X^{10}$ is independently $CR^{16}$, $CR^{17}R^{18}$, N, $NR^{19}$, O, or S;
each of $L^1$ and $L^2$ is independently a bond, carbonyl, O, S, —$NR^5$—, —$NR^6CH_2$—, —$NR^6C(=O)$—, —$NR^6SO_2$—, alkylene, alkenylene, heteroalkylene, alkylenecarbonyl, alkenylenecarbonyl, or heteroalkylenecarbonyl;
A is a bond, a 3-7 membered saturated ring, or a 3-7 membered unsaturated ring;
m is an integer from 0 to 12;
B is selected from B-I, B-II, B-III, and B-IV;
wherein B is connected at any ring atom to $L^2$;
B-I is

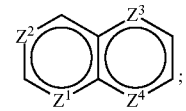

B-II is

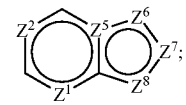

B-III is

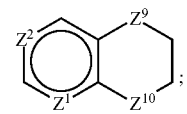

B-IV is

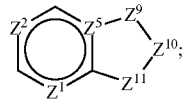

each of $Z^1$, $Z^2$, $Z^3$, and $Z^4$ is independently $CR^7$, N, or $NR^9$; $Z^5$ is C or N;
each of $Z^6$, $Z^7$, and $Z^8$ is independently $CR^8$, N, $NR^9$, O, or S;
each of $Z^9$, $Z^{10}$, and $Z^{11}$ is independently $CR^1$, $CR^{11}R^{12}$, $NR^{13}$, O, or S; n is an integer from 0 to 6;
each of $R^2$, $R^5$, $R^6$, $R^7$, $R^8$, $R^9$, $R^{10}$, $R^{11}$, $R^{12}$, $R^{13}$, $R^{16}$, $R^{17}$, $R^{18}$, and $R^{19}$ is, at each occurrence, independently selected from H, halo, hydroxyl, amino, cyano, dialkylphosphine oxide, oxo, carboxyl, amido, acyl, alkyl, cycloalkyl, heteroalkyl, haloalkyl, aminoalkyl, hydroxyalkyl, alkoxy, alkylamino, cycloalkylalkyl, cycloalkyloxy, cycloalkylalkyloxy, cycloalkylamino, cycloalkylalkylamino, heterocyclyl, heterocyclylalkyl, heterocyclyloxy, heterocyclylalkyloxy, heterocyclylamino, heterocyclylalkylamino, aryl, aralkyl, aryloxy, aralkyloxy, arylamino, aralkylamino, heteroaryl, heteroarylalkyl, heteroaryloxy, heteroarylalkyloxy, heteroarylamino, and heteroarylalkylamino; and
each of $R^A$ and $R^B$ is, at each occurrence, independently selected from halo, hydroxyl, amino, cyano, dialkylphosphine oxide, oxo, carboxyl, amido, acyl, alkyl, cycloalkyl, heteroalkyl, haloalkyl, aminoalkyl, hydroxyalkyl, alkoxy, alkylamino, cycloalkylalkyl, cycloalkyloxy, cycloalkylalkyloxy, cycloalkylamino, cycloalkylalkylamino, heterocyclyl, heterocyclylalkyl, heterocyclyloxy, heterocyclylalkyloxy, heterocyclylamino, heterocyclylalkylamino, aryl, aralkyl, aryloxy, aralkyloxy, arylamino, aralkylamino, heteroaryl, heteroarylalkyl, heteroaryloxy, heteroarylalkyloxy, heteroarylamino, and heteroarylalkylamino,
wherein two $R^A$ groups or two $R^B$ groups attached to the same atom or different atoms can together optionally form a bridge or ring.

In some embodiments of a compound provided herein, A is cycloalkyl, heterocyclic ring, aryl or heteroaryl. In some embodiments of a compound provided herein, A has one of the following structures:

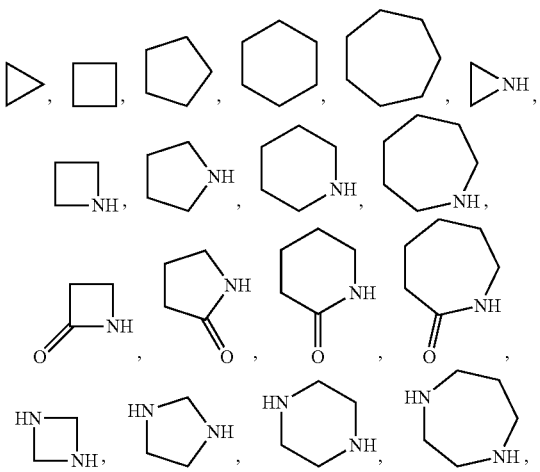

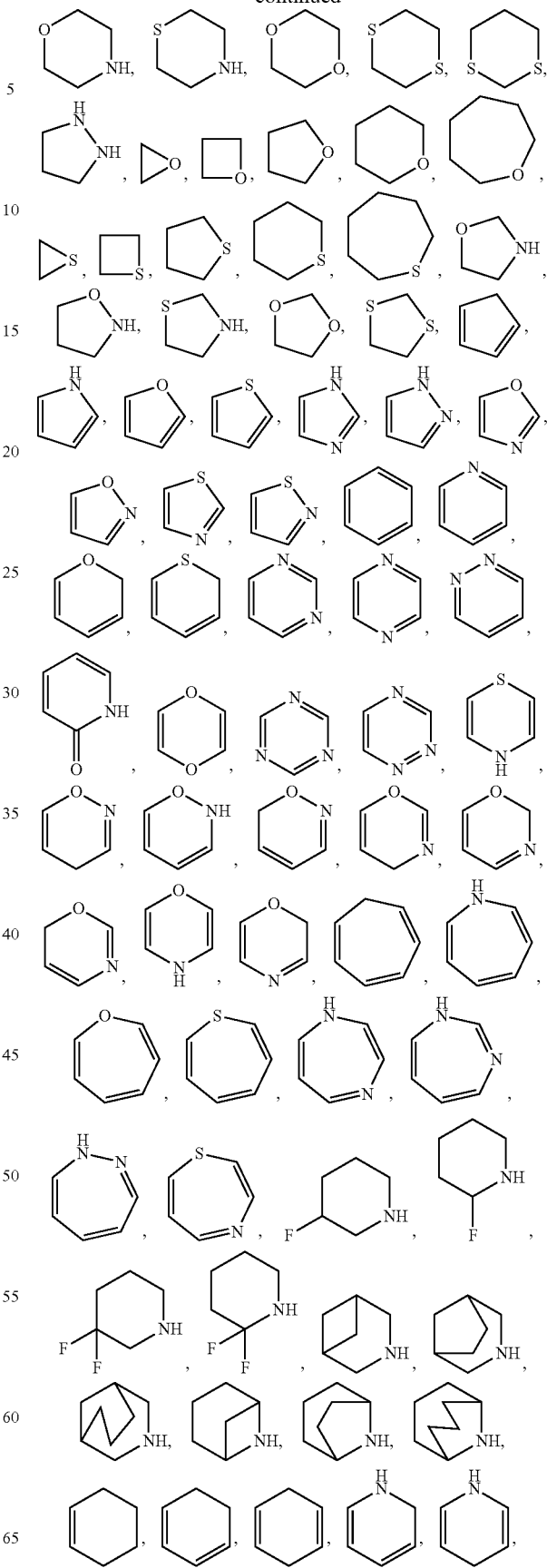

-continued

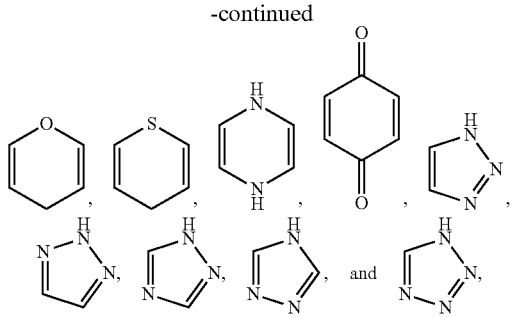

wherein the H of any CH or NH may be replaced with a bond to $L^1$, $L^2$ or $R^A$. In some embodiments of a compound provided herein, A, when present, is a 5-membered cycloalkyl, 6-membered cycloalkyl, 5-membered heterocyclic ring, 6-membered heterocyclic ring, 6-membered aryl, 5-membered heteroaryl, or 6-membered heteroaryl.

In some embodiments, the compound has the structure of Formula VII-A:

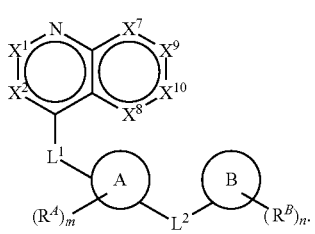

(VII-A)

In some embodiments, the compound has the structure of Formula VII-B:

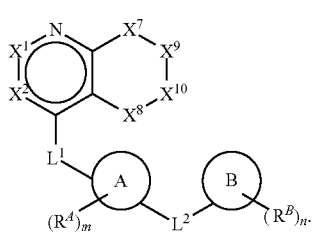

(VII-B)

In some embodiments, the compound has the structure of Formula VII-C:

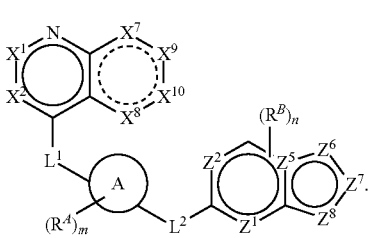

(VII-C)

In some embodiments, the compound has the structure of Formula VII-D:

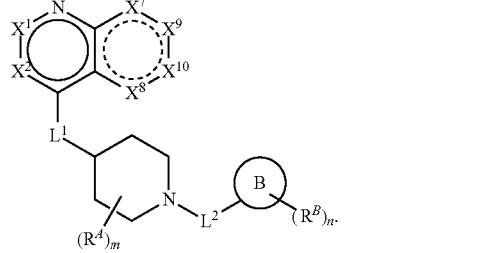

(VII-D)

In some embodiments, the compound has the structure of Formula VII-E:

(VII-E)

In some embodiments, the compound has the structure of Formula VII-F:

(VII-F)

In some embodiments, the compound has the structure of Formula VII-G:

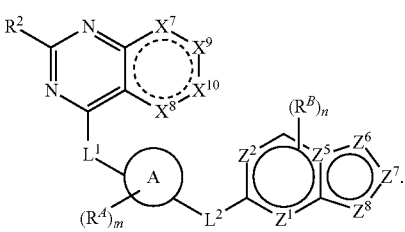

(VII-G)

In some embodiments, the compound has the structure of Formula VII-H:

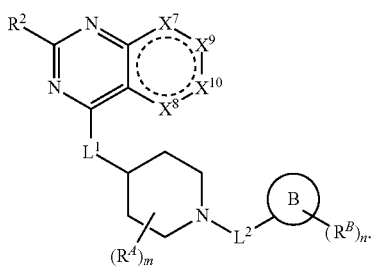

(VII-H)

In some embodiments, the compound has the structure of Formula VII-I:

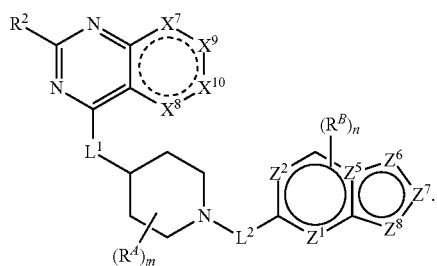

(VII-I)

In some embodiments, the compound has the structure of Formula VII-J:

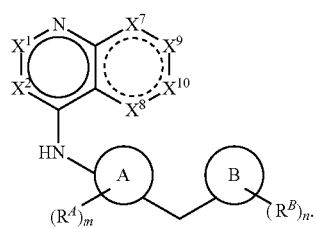

(VII-J)

In some embodiments, the compound has the structure of Formula VII-K:

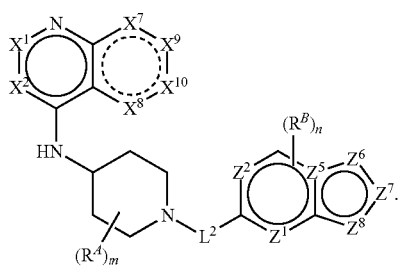

(VII-K)

In some embodiments of a compound provided herein, $L^2$, when present, is —CH$_2$—, NR$^5$, —NR$^6$CH$_2$—, —NR$^6$C(=O)—, or —NR$^6$SO$_2$—.

In some embodiments of a compound provided herein, $X^1$, when present, is CR$^2$.

In some embodiments of a compound of Formula VII, Formula VII-A, Formula VII-B, Formula VII-C, Formula VII-D, Formula VII-E, Formula VII-J, or Formula VII-K, $R^2$ in $X^1$ is halo, hydroxyl, alkoxy, alkylamino, amino, cyano, amido, alkyl, heteroalkyl, or haloalkyl. In some embodiments of a compound of Formula VII, Formula VII-A, Formula VII-B, Formula VII-C, Formula VII-D, Formula VII-E, Formula VII-J, or Formula VII-K, $R^2$ in $X^1$ is amino. In some embodiments of a compound of Formula VII, Formula VII-A, Formula VII-B, Formula VII-C, Formula VII-D, Formula VII-E, Formula VII-J, or Formula VII-K, $R^2$ in $X^1$ is alkyl, such as $C_1$-$C_3$ alkyl or methyl.

In some embodiments of a compound of Formula VII-F, Formula VII-G, Formula VII-H, or Formula VII-I, $R^2$ is halo, hydroxyl, alkoxy, alkylamino, amino, cyano, amido, alkyl, heteroalkyl, or haloalkyl. In some embodiments of a compound of Formula VII-F, Formula VII-G, Formula VII-H, or Formula VII-I, $R^2$ is amino. In some embodiments of a compound of Formula VII-F, Formula VII-G, Formula VII-H, or Formula VII-I, $R^2$ is alkyl, such as $C_1$-$C_3$ alkyl or methyl.

In some embodiments of a compound provided herein, $X^2$, when present, is N. In some embodiments of the compounds provided herein, $X^2$, when present, is CR$^2$.

In some embodiments of a compound provided herein, $X^7$, when present, is N or NR$^{19}$.

In some embodiments of a compound provided herein, $X^9$, when present, is NR$^{19}$. In some embodiments of a compound provided herein, $X^9$, when present, is CR$^{16}$. In some embodiments of a compound provided herein, $X^9$, when present, is N(CH$_2$)$_{n'}$CF$_3$, N(CH$_2$)$_{n'}$CHF$_2$ or N(CH$_2$)$_{n'}$CH$_2$F, wherein n' is 1, 2 or 3. In some embodiments of a compound provided herein, $X^9$, when present, is C(CH$_2$)$_{n'}$CF$_3$, C(CH$_2$)$_{n'}$CHF$_2$, C(CH$_2$)$_{n'}$CH$_2$F, CR$^{17}$(CH$_2$)$_{n'}$CF$_3$, CR$^{17}$(CH$_2$)$_{n'}$CHF$_2$, or CR$^{17}$(CH$_2$)$_{n'}$CH$_2$F, wherein n' is 1, 2 or 3.

In some embodiments of a compound provided herein, $X^{10}$, when present, is N(CH$_2$)$_{n'}$CF$_3$, N(CH$_2$)$_{n'}$CHF$_2$ or N(CH$_2$)$_{n'}$CH$_2$F, wherein n' is 1, 2 or 3. In some embodiments of a compound provided herein, $X^{10}$, when present, is C(CH$_2$)$_{n'}$CF$_3$, C(CH$_2$)$_{n'}$CHF$_2$, C(CH$_2$)$_{n'}$CH$_2$F, CR$^{17}$(CH$_2$)$_{n'}$CF$_3$, CR$^{17}$(CH$_2$)$_{n'}$CHF$_2$, or CR$^{17}$(CH$_2$)$_{n'}$CH$_2$F, wherein n' is 1, 2 or 3.

In some embodiments of a compound provided herein, m is 0. In some embodiments of a compound provided herein, m is 1, 2 or 3.

In some embodiments of a compound provided herein, $R^4$, when present, is, at each occurrence, independently selected from H, halo, oxo, alkyl, haloalkyl, cycloalkyl, aryl, heteroaryl, heterocyclyl, aralkyl, heteroarylalkyl, heterocyclylalkyl, and cycloalkylalkyl.

In some embodiments of a compound provided herein, n is 0. In some embodiments of a compound provided herein, n is 1 or 2.

In some embodiments of a compound provided herein, $R^5$, when present, is H or alkyl.

In some embodiments of a compound provided herein, $R^2$, $R^{16}$, $R^{17}$ and $R^{19}$, when present, are each independently H or haloalkyl. In some embodiments of a compound provided herein, $R^2$, $R^{16}$, $R^{17}$ and $R^{19}$, when present, are each independently H, (CH$_2$)$_{n'}$CF$_3$, (CH$_2$)$_{n'}$CHF$_2$ or (CH$_2$)$_{n'}$CH$_2$F, wherein n' is 1, 2 or 3.

In some embodiments of a compound provided herein, each $R^7$, when present, is independently H, halo, hydroxyl, $C_1$-$C_4$ alkyl or $C_1$-$C_4$ alkoxy.

In some embodiments of a compound provided herein, each $R^8$, when present, is independently H, $C_1$-$C_4$ alkyl or cyano.

In some embodiments of a compound provided herein, each $R^9$, when present, is independently H, $C_1$-$C_4$ alkyl, aralkyl, heteroarylalkyl, heterocyclylalkyl, or cycloalkylalkyl. In some embodiments of a compound provided herein, each $R^9$, when present, is independently H, $C_1$-$C_4$ alkyl or

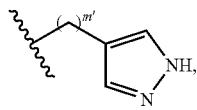

wherein m' is 1, 2 or 3.

In some embodiments of a compound provided herein comprising B-II, $Z^1$ and $Z^2$ are $CR^7$; $Z^5$ is C; $Z^6$ is $NR^9$; and $Z^7$ and $Z^8$ are $CR^8$. In some embodiments of a compound provided herein comprising B-II, $Z^1$ is $CCH_3$; $Z^2$ and $Z^8$ are CH; $Z^5$ is C; $Z^6$ is $NR^9$; and $Z^7$ is CCN.

In some embodiments of a compound provided herein, B, when present, is B-I. In some embodiments, B-I is connected to $L^2$ at a ring carbon. In some embodiments, B-I is connected to $L^2$ at a position selected from

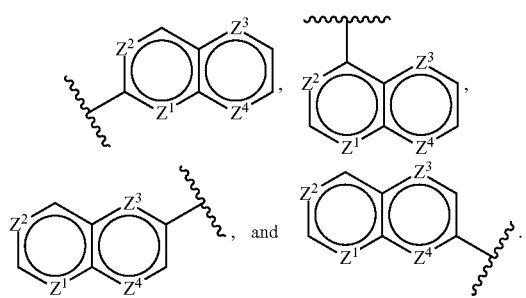

In some embodiments of a compound provided herein, B, when present, is B-II. In some embodiments, B-II is connected to $L^2$ at a ring carbon. In some embodiments, B-II is connected to $L^2$ at a position selected from

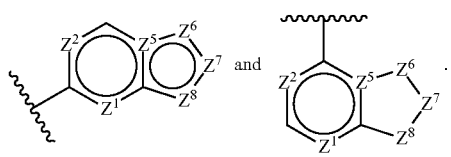

In some embodiments of a compound provided herein, B, when present, is B-III. In some embodiments, B-III is connected to $L^2$ at a ring carbon. In some embodiments, B-III is connected to $L^2$ at a position selected from

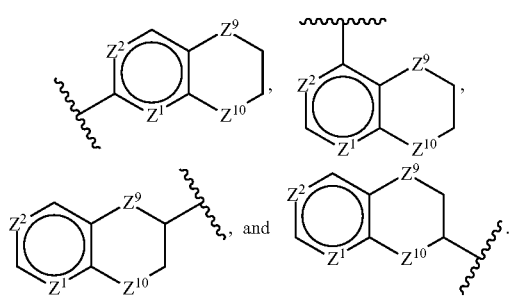

In some embodiments of a compound provided herein, B, when present, is B-IV. In some embodiments, B-IV is connected to $L^2$, when present, or $L^4$, when present, at a ring carbon. In some embodiments, B-IV is connected to $L^2$, when present, or $L^4$, when present, at a position selected from

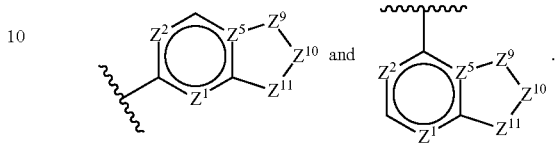

In some embodiments of a compound provided herein, the compound does not comprise a functional group that covalently reacts with one or more residues on menin.

In some embodiments of a compound provided herein, the compound is capable of (a) binding non-covalently to menin and (b) inhibiting the iteration of menin and MLL.

In some embodiments of a compound provided herein, one or more of $R^2$, $R^5$, $R^6$, $R^7$, $R^8$, $R^9$, $R^{10}$, $R^{11}$, $R^{12}$, $R^{13}$, $R^{16}$, $R^{17}$, $R^{18}$, $R^{19}$, $R^A$, and $R^B$, when present, comprises a functional group that covalently reacts with one or more residues on menin. In some embodiments of a compound provided herein, the functional group covalently reacts with one or more cysteine residues on menin. In some embodiments of a compound provided herein, the functional group covalently reacts with a cysteine on menin at position 329 relative to SEQ ID NO: 2 when optimally aligned or position 334 relative to SEQ ID NO: 1 when optimally aligned.

In some embodiments of a compound provided herein, the compound is capable of (a) binding covalently to menin and (b) inhibiting the iteration of menin and MLL.

In some embodiments of a compound provided herein, the compound comprises an $R^B$ selected from:

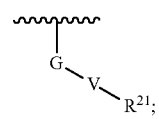

wherein:
G is selected from a bond, alkylene, heteroalkylene, $C_{3-12}$ carbocycle, 3- to 12-membered heterocycle, and combinations thereof, wherein G is optionally substituted with one or more $R^{32}$ groups;
V is absent or selected from a $C_{3-12}$ carbocycle, and 3- to 12-membered heterocycle; wherein V is optionally substituted with one or more $R^{32}$ groups;
each of $R^{21}$ and $R^{32}$ is, at each occurrence, independently selected from:
H, halogen, —$OR^{20}$, —$SR^{20}$, —$N(R^{20})_2$, —$N(R^{20})C(O)R^{20}$, —$C(O)R^{20}$, —$C(O)OR^{20}$, —$C(O)N(R^{20})_2$, —$OC(O)R^{20}$, —$S(O)_2R^{20}$, —$S(O)_2N(R^{20})_2$, —$N(R^{20})S(O)_2R^{20}$, —$NO_2$, =O, =S, =$N(R^{20})$, —$P(O)(OR^{20})_2$, —$P(O)(R^{20})_2$, —$OP(O)(OR^{20})_2$, and —CN;
$C_{1-6}$ alkyl, $C_{2-6}$ alkenyl, and $C_{2-6}$ alkynyl, each of which is independently optionally substituted at each occurrence with one or more substituents selected from halogen, —$OR^{20}$, —$SR^{20}$, —$N(R^{20})_2$, —$N(R^{20})C(O)R^{20}$, —$C(O)R^{20}$, —$C(O)OR^{20}$, —$C(O)N(R^{20})_2$, —$OC(O)R^{20}$, —$S(O)_2R^{20}$, —$S(O)_2$ N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, —CN, C$_{3-10}$ carbocycle, and 3- to 10-membered heterocycle; and C$_{3-10}$ carbocycle and 3- to 10-membered heterocycle; wherein two R$^{32}$ on the same carbon atom can come together to form a C$_{3-10}$ carbocycle or 3- to 10-membered heterocycle;

wherein each C$_{3-10}$ carbocycle and 3- to 10-membered heterocycle of R$^{32}$ is independently optionally substituted with one or more substituents selected from halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, —CN, C$_{1-6}$ alkyl, C$_{2-6}$ alkenyl, and C$_{2-6}$ alkynyl;

R$^{20}$ at each occurrence is independently selected from: hydrogen;

C$_{1-6}$ alkyl, C$_{2-6}$ alkenyl, and C$_{2-6}$ alkynyl, each of which is independently optionally substituted at each occurrence with one or more substituents selected from halogen, —OR$^{30}$, —SR$^{30}$, —N(R$^{30}$)$_2$, —N(R$^{30}$)C(O)R$^{30}$, —C(O)R$^{30}$, —C(O)OR$^{30}$, —C(O)N(R$^{30}$)$_2$, —OC(O)R$^{30}$, —S(O)$_2$R$^{30}$, —S(O)$_2$N(R$^{30}$)$_2$, —N(R$^{30}$)S(O)$_2$R$^{30}$, —NO$_2$, —P(O)(OR$^{30}$)$_2$, —P(O)(R$^{30}$)$_2$, —OP(O)(OR$^{30}$)$_2$, and —CN; and 3- to 10-membered heterocycle and C$_{3-10}$ carbocycle; and R$^{30}$ at each occurrence is independently selected from hydrogen, C$_{1-6}$ alkyl, C$_{2-6}$ alkenyl, and C$_{2-6}$ alkynyl.

In some embodiments of a compound provided herein, R$^{21}$ comprises a functional group that covalently reacts with one or more residues on menin. In some embodiments of a compound provided herein, the functional group covalently reacts with one or more cysteine residues on menin. In some embodiments of a compound provided herein, the functional group covalently reacts with a cysteine on menin at position 329 relative to SEQ ID NO: 2 when optimally aligned or position 334 relative to SEQ ID NO: 1 when optimally aligned.

In some embodiments of a compound provided herein, R$^{21}$ is a moiety comprising an alpha, beta-unsaturated carbonyl; an alpha, beta-unsaturated sulfonyl; an epoxide; an aldehyde; sulfonyl fluoride; a halomethylcarbonyl; a dihalomethylcarbonyl; or a trihalomethylcarbonyl.

In some embodiments of a compound provided herein, R$^{21}$ is selected from:

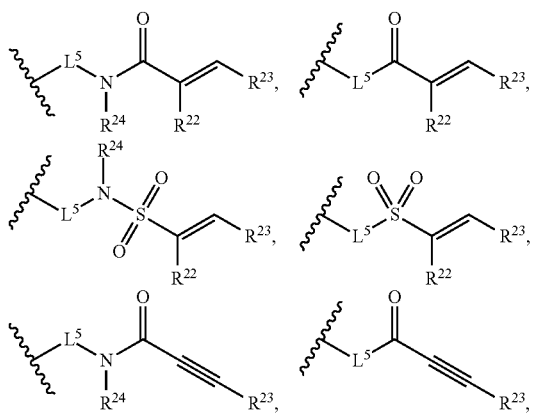

-continued

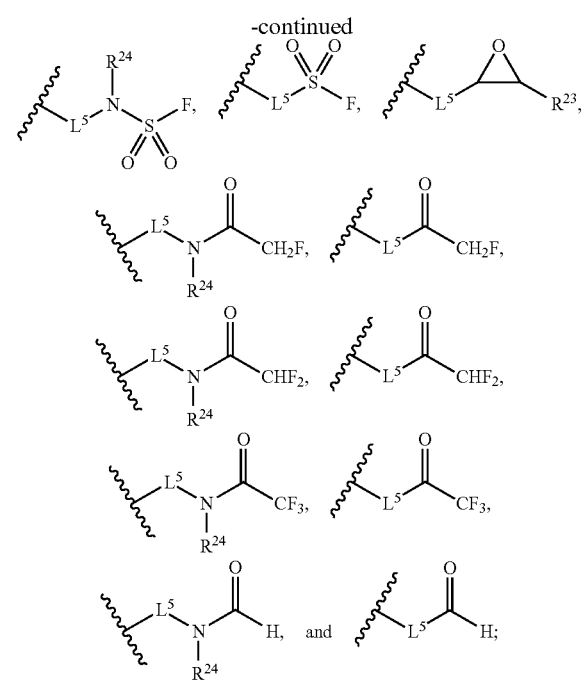

wherein:

L$^5$ is selected from a bond; and C$_{1-6}$ alkylene, C$_{1-6}$ heteroalkylene, C$_{2-6}$ alkenylene, and C$_{2-6}$ alkynylene, each of which is independently optionally substituted with one or more R$^{32}$ groups;

R$^{22}$ and R$^{23}$ are selected from hydrogen, halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, and —CN;

C$_{1-6}$ alkyl, C$_{2-6}$ alkenyl, and C$_{2-6}$ alkynyl, each of which is independently optionally substituted at each occurrence with one or more substituents selected from halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, —CN, C$_{3-10}$ carbocycle, and 3- to 10-membered heterocycle; and C$_{3-10}$ carbocycle and 3- to 10-membered heterocycle, wherein each C$_{3-10}$ carbocycle and 3- to 10-membered heterocycle of R$^{22}$ and R$^{23}$ is independently optionally substituted with one or more substituents selected from halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, —CN, C$_{1-6}$ alkyl, C$_{2-6}$ alkenyl, and C$_{2-6}$ alkynyl; or R$^{22}$ and R$^{23}$, together with the carbon atoms to which they are attached, form a carbocyclic ring;

R$^{24}$ is selected from:

hydrogen, —C(O)R$^{20}$, —C(O)OR$^{20}$, —C(O)N(R$^{20}$)$_2$, —OC(O)R$^{20}$, —S(O)$_2$R$^{20}$, and —S(O)$_2$N(R$^{20}$)$_2$;

C$_{1-6}$ alkyl, C$_{2-6}$ alkenyl, and C$_{2-6}$ alkynyl, each of which is independently optionally substituted at each occurrence with one or more substituents selected from halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, —CN, C$_{3-10}$ carbocycle, and 3- to 10-membered heterocycle; and C$_{3-10}$ carbocycle and 3- to 10-membered heterocycle, wherein each C$_{3-10}$ carbocycle and 3- to 10-membered heterocycle of R$^{24}$ is independently optionally substituted with one or more substituents selected from halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, —CN, C$_{1-6}$ alkyl, C$_{2-6}$ alkenyl, and C$_{2-6}$ alkynyl.

In some embodiments of a compound provided herein, L$^5$ is a bond. In some embodiments of a compound provided herein, L$^5$ is optionally substituted C$_{1-6}$ alkylene. In some embodiments of a compound provided herein, L$^5$ is selected from methylene, ethylene or propylene. In some embodiments of a compound provided herein, L$^5$ is substituted with one or more substituents selected from halogen, —NO$_2$, =O, =S, —OR$^{20}$, —SR$^{20}$, and —N(R$^{20}$)$_2$.

In some embodiments of a compound provided herein, R$^{23}$ is selected from:
hydrogen;
C$_{1-6}$ alkyl, C$_{2-6}$ alkenyl, and C$_{2-6}$ alkynyl, each of which is independently optionally substituted at each occurrence with one or more substituents selected from halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, —CN, C$_{3-10}$ carbocycle and 3- to 10-membered heterocycle; and
C$_{3-10}$ carbocycle, and 3- to 10-membered heterocycle,
wherein each C$_{3-10}$ carbocycle and 3- to 10-membered heterocycle is independently optionally substituted with one or more substituents selected from halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, —CN, C$_{1-6}$ alkyl, C$_{2-6}$ alkenyl, and C$_{2-6}$ alkynyl.

In some embodiments of a compound provided herein, R$^{23}$ is selected from:
hydrogen;
C$_{1-6}$ alkyl optionally substituted with one or more substituents selected from halogen, —OR$^{20}$, —SR$^{20}$, —N(R$^{20}$)$_2$, =O, =S, =N(R$^{20}$), and —CN; and 3- to 10-membered heterocycle optionally substituted with one or more substituents selected from halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, —CN, C$_{1-6}$ alkyl, C$_{2-6}$ alkenyl, and C$_{2-6}$ alkynyl.

In some embodiments of a compound provided herein, R$^{23}$ is selected from hydrogen and C$_{1-6}$ alkyl optionally substituted with one or more substituents selected from halogen, —OR$^{20}$, —SR$^{20}$, —N(R$^{20}$)$_2$, =O, =S, =N(R$^{20}$), and —CN.

In some embodiments of a compound provided herein, R$^{22}$ is selected from:
hydrogen and —CN;
C$_{1-6}$ alkyl, C$_{2-6}$ alkenyl, and C$_{2-6}$ alkynyl, each of which is independently optionally substituted at each occurrence with one or more substituents selected from halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, —S(O)$_2$N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, —CN, C$_{3-10}$ carbocycle and 3- to 10-membered heterocycle; and C$_{3-10}$ carbocycle and 3- to 10-membered heterocycle,
wherein each C$_{3-10}$ carbocycle and 3- to 10-membered heterocycle is independently optionally substituted with one or more substituents selected from halogen, —OR$^{20}$, —SR$^{20}$, —N(R$^{20}$)$_2$, —N(R$^{20}$)C(O)R$^{20}$, —C(O)R$^{20}$, —C(O)OR$^{20}$, —C(O)N(R$^{20}$)$_2$, —OC(O)R$^{20}$, —S(O)$_2$R$^{20}$, S(O)$_2$N(R$^{20}$)$_2$, —N(R$^{20}$)S(O)$_2$R$^{20}$, —NO$_2$, =O, =S, =N(R$^{20}$), —P(O)(OR$^{20}$)$_2$, —P(O)(R$^{20}$)$_2$, —OP(O)(OR$^{20}$)$_2$, —CN, C$_{1-6}$ alkyl, C$_{2-6}$ alkenyl, and C$_{2-6}$ alkynyl.

In some embodiments of a compound provided herein, R$^{22}$ is selected from hydrogen; —CN; and C$_{1-6}$ alkyl optionally substituted with one or more substituents selected from halogen, —OR$^{20}$, —SR$^{20}$, and —N(R$^{20}$)$_2$.

In some embodiments of a compound provided herein, R$^{22}$ and R$^{23}$, together with the carbon atoms to which they are attached, form a 5-, 6-, or 7-membered carbocyclic ring.

In some embodiments of a compound provided herein, R$^{24}$ is selected from hydrogen and C$_{1-6}$ alkyl optionally substituted with one or more substituents selected from halogen, —OR$^{20}$, —SR$^{20}$, —N(R$^{20}$)$_2$, —NO$_2$, =O, and —CN.

In some embodiments of a compound provided herein, R$^{21}$ is selected from:

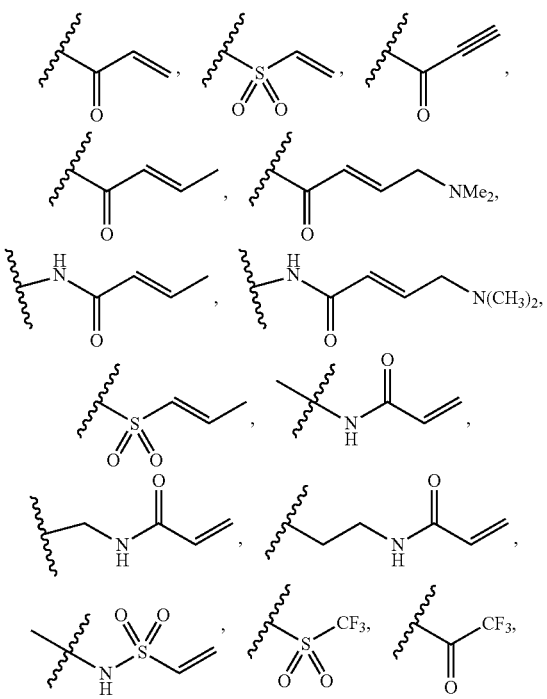

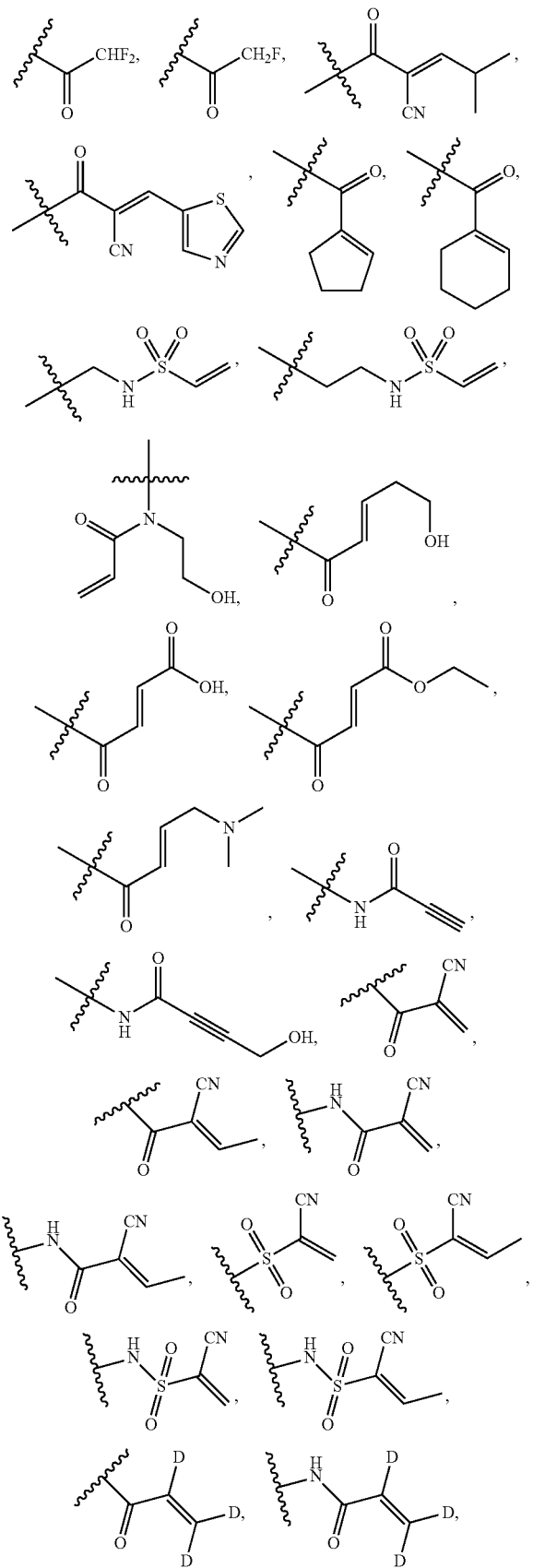

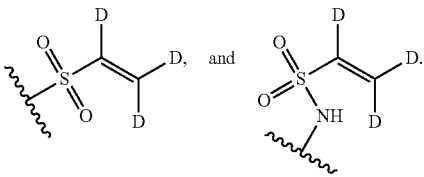

In some embodiments of a compound provided herein, $R^{21}$ is a moiety with 5 to 50 atoms.

In some embodiments of a compound provided herein, $R^{21}$ is a moiety with 5 to 40 atoms.

In some embodiments, V is selected from a 3-8 membered saturated ring, 3-8 membered unsaturated ring, 4-10 membered fused bicyclic ring, and 5-11 membered spiro bicyclic ring. V may be optionally substituted with one or more $R^{32}$ groups, such as with 1, 2, 3, 4, or 5 $R^{32}$ groups. In some embodiments, V is a 3-7 membered saturated ring, such as a 3-7 membered cycloalkyl or 3-7 membered aromatic or non-aromatic heterocycle. In some embodiments, V is a 3-7 membered unsaturated ring, such as a 6 membered aryl, 5-6 membered heteroaryl, or 3-7 membered cycloalkenyl.

In some embodiments of a compound provided herein, V is selected from a 3-8 membered saturated ring optionally substituted with one or more $R^{32}$ groups. In some embodiments of a compound provided herein, V is a 3-, 4-, 5-, 6- or 7-membered saturated carbocycle, any one of which is optionally substituted with one or more $R^{32}$ groups. In some embodiments of a compound provided herein, V is selected from:

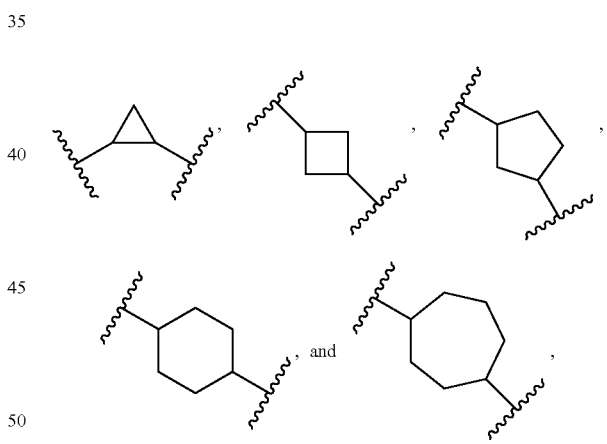

any one of which is optionally substituted with one or more $R^{32}$ groups.

In some embodiments of a compound provided herein, V is a 4-, 5-, 6-, 7- or 8-membered saturated heterocycle, any one of which is optionally substituted with one or more $R^{32}$ groups. In some embodiments of a compound provided herein, V is selected from azetidine, oxetane, piperidine, oxane, piperazine, pyrrolidine, tetrahydrofuran, thiolane, imidazolidine, morpholine, thiomorpholine, azepane, and homopiperazine, any one of which is optionally substituted with one or more $R^{32}$ groups. In some embodiments of a compound provided herein, V is selected from:

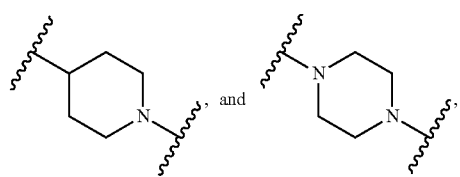

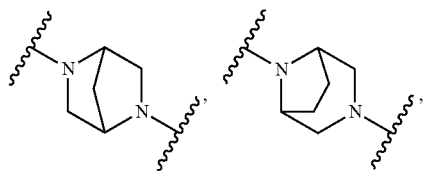

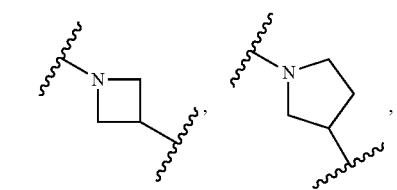

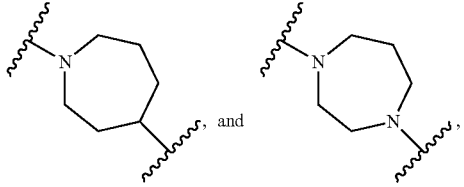

any one of which is optionally substituted with one or more $R^{32}$ groups.

In some embodiments of a compound provided herein, V is a bicyclic heterocycle, optionally substituted with one or more $R^{32}$ groups. In some embodiments of a compound provided herein, V is selected from

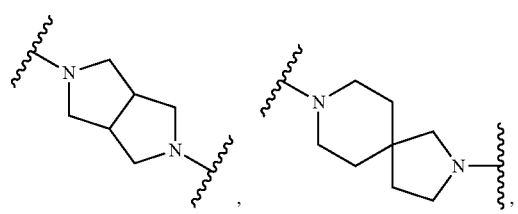

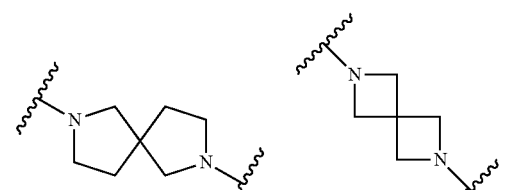

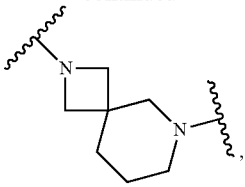

any one of which is optionally substituted with one or more $R^{32}$ groups.

In certain embodiments, V is a 4-10 membered fused bicyclic ring, such as a 8-10 membered fused bicyclic ring. In certain embodiments, the fused bicyclic ring includes one or more heteroatoms such as one or more atoms selected from N, O, and S. In certain embodiments, the fused bicyclic ring includes two heteroatoms such as two nitrogen atoms. Each of the rings of the fused bicyclic ring may be saturated or unsaturated. In particular embodiments, both rings of the fused bicyclic ring are saturated. Non-limiting examples of V comprising a fused bicyclic ring include

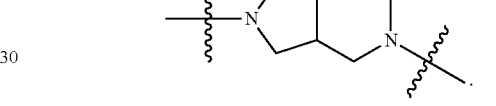

and

In some embodiments, V is a 5-11 membered spiro bicyclic ring, such as a 7-11 membered spiro bicyclic ring. In certain embodiments, the fused bicyclic ring includes one or more heteroatoms such as one or more atoms selected from N, O, and S. In particular embodiments, the fused bicyclic ring includes two heteroatoms such as two nitrogen atoms. Non-limiting examples of V comprising a spiro bicyclic ring include

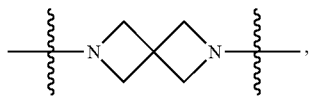

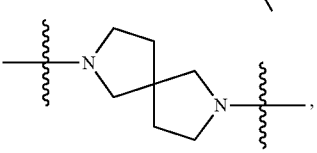

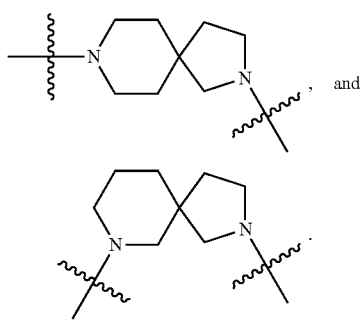, and

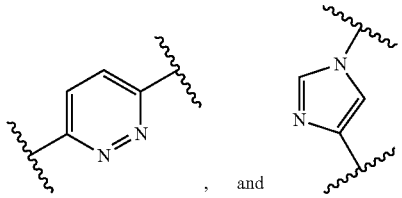, and

In some embodiments of a compound provided herein, V is selected from an unsaturated, aromatic, or heteroaromatic ring, any one of which is optionally substituted with one or more $R^{32}$ groups. In some embodiments of a compound provided herein, V is selected from phenyl, pyridine, pyrazine, pyrimidine, pyridazine, naphthalene, anthracene, quinoline, isoquinoline, quinoxaline, acridine, quinazoline, cinnoline, phthalazine, furan, dihydrofuran, thiophene, dihydrothiophene, imidazole, imidazoline, oxazole, oxazoline, pyrrole, dihydropyrrole, thiazole, dihydrothiazole, pyrazole, dihydropyrazole, isoxazole, dihydroisoxazole, isothiazole, dihydroisothiazole, benzofuran, isobenzofuran, indole, isoindole, benzothiophene, benzimidazole, purine, indazole, benzoxazole, benzisoxazole, and benzothiazole, any one of which is optionally substituted with one or more $R^{32}$ groups. In some embodiments of a compound provided herein, V is phenyl, optionally substituted with one or more $R^{32}$ groups. In some embodiments of a compound provided herein, V is a heteroaromatic ring optionally substituted with one or more $R^{32}$ groups. In some embodiments of a compound provided herein, V is selected from pyridine, pyrazine, pyrimidine, pyridazine, naphthalene, anthracene, quinoline, isoquinoline, quinoxaline, acridine, quinazoline, cinnoline, phthalazine, furan, thiophene, imidazole, oxazole, pyrrole, thiazole, pyrazole, isoxazole, isothiazole, benzofuran, isobenzofuran, indole, isoindole, benzothiophene, benzimidazole, purine, indazole, benzoxazole, benzisoxazole, and benzothiazole, any one of which is optionally substituted with one or more $R^{32}$ groups. In some embodiments of a compound provided herein, V is selected from

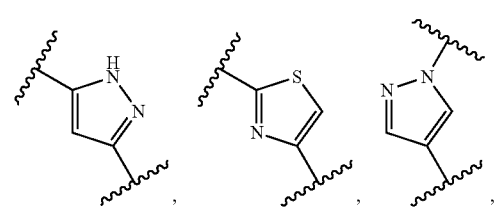

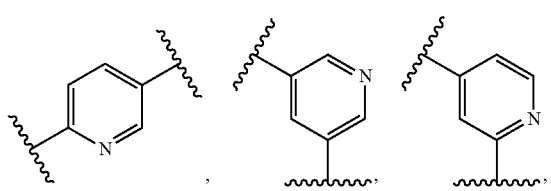

wherein any one of which is optionally substituted with one or more $R^{32}$ groups.

In some embodiments of a compound provided herein, V is absent.

In some embodiments of a compound provided herein, G is a bond.

In some embodiments of a compound provided herein, G is alkylene optionally substituted with one or more $R^{32}$ groups.

In some embodiments of a compound provided herein, G is selected from methylene, ethylene, propylene, and butylene, any one of which is optionally substituted with one or more $R^{32}$ groups. In some embodiments of a compound provided herein, G is selected from:

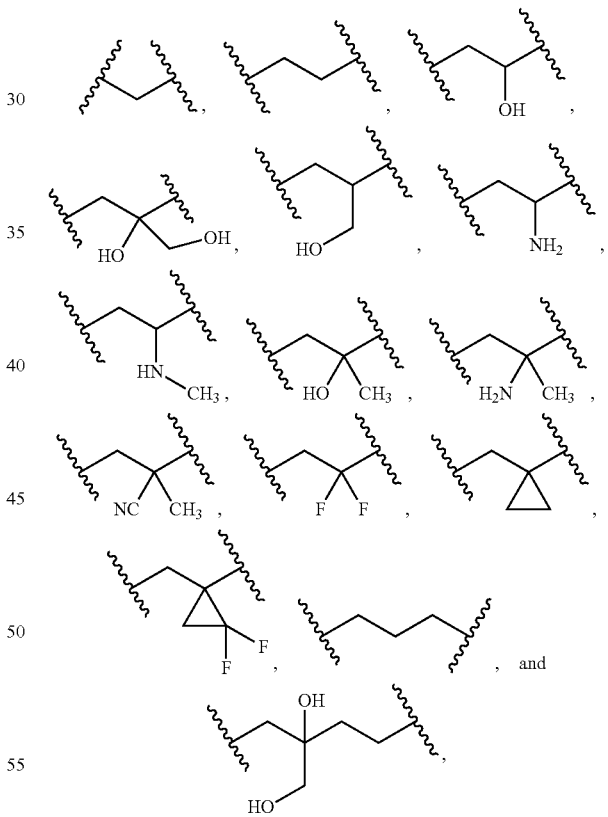

wherein any one of which is optionally substituted with one or more $R^{32}$ groups.

In some embodiments of a compound provided herein, G is a heteroalkylene optionally substituted with one or more $R^{32}$ groups.

In some embodiments of a compound provided herein, G is a $C_{3-10}$ carbocycle or 3- to 10-membered heterocycle, any one of which is optionally substituted with one or more $R^{32}$ groups.

In some embodiments of a compound provided herein, G is a saturated $C_{3-10}$ carbocycle or saturated 3- to 10-membered heterocycle, any one of which is optionally substituted with one or more $R^{32}$ groups.

In some embodiments of a compound provided herein, G is selected from:

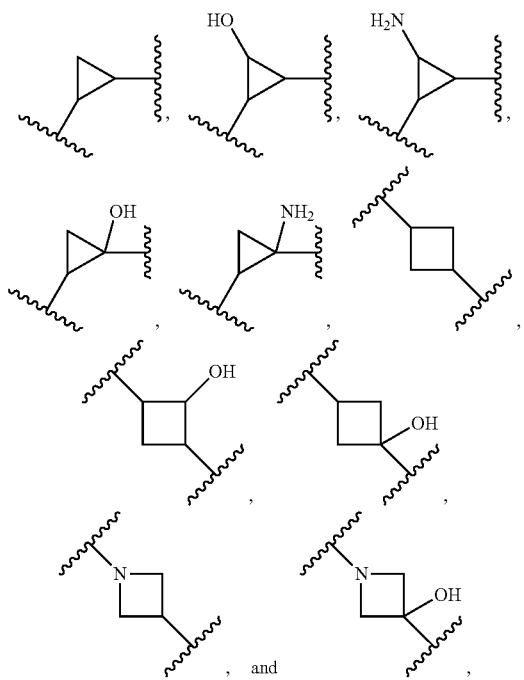

wherein any one of which is optionally substituted with one or more $R^{32}$ groups.

In some embodiments, the compound is selected from Table 4g.

In another aspect, the present disclosure provides a pharmaceutical composition comprising a compound disclosed herein and a pharmaceutically acceptable carrier. In some embodiments, the pharmaceutical composition is formulated for oral administration. In some embodiments, the pharmaceutical composition is formulated for injection.

In yet another aspect, the present disclosure provides a method of inhibiting the interaction of menin and one or more of MLL1, MLL2, a MLL fusion protein, and a MLL Partial Tandem Duplication, comprising contacting menin with an effective amount of a compound disclosed herein.

In another aspect, the present disclosure provides a method of inhibiting the menin-MLL interaction, comprising contacting menin with an effective amount of a compound disclosed herein, wherein inhibition of the interaction is evidenced by a reduction in the expression of a MLL fusion protein target gene, such as HOXA9, DLX2, or MEIS1.

In another aspect, the present disclosure provides a method of stabilizing menin, comprising contacting menin with a compound disclosed herein. In some embodiments, the contacting step comprises contacting menin with an amount of the compound sufficient to stabilize menin. In some embodiments, the contacting step takes place in a cell.

In some embodiments of a method disclosed herein, the step of contacting comprises contacting a cell that expresses menin. In some embodiments of a method disclosed herein, the method comprises administering a second therapeutic agent to the cell. In some embodiments of a method disclosed herein, the contacting step takes place in vivo. In some embodiments of a method disclosed herein, the contacting step takes place in vitro.

In another aspect, the present disclosure provides a method of treating a disease or condition associated with MLL fusion proteins, comprising administering to a subject in need thereof an effective amount of a compound disclosed herein.

In yet another aspect, the present disclosure provides a method of treating a disease or condition in a subject, comprising administering to the subject a therapeutically effective amount of a pharmaceutical composition of a compound disclosed herein.

In some embodiments of a method disclosed herein, the disease or condition comprises a leukemia, hematologic malignancies, solid tumor cancer, prostate cancer, breast cancer, liver cancer, brain tumor, or diabetes. In some embodiments, the leukemia comprises AML, ALL, Mixed Lineage Leukemia or leukemias with Partial Tandem Duplications of MLL.

In another aspect, the present disclosure provides a method of treating a disorder mediated by chromosomal rearrangement on chromosome 11q23 in a subject in need thereof, the method comprising: administering to the subject a therapeutically effective amount of a compound disclosed herein.

In yet another aspect, the present disclosure provides a method of treating a disorder mediated by an interaction between menin and another protein, comprising administering to a subject in need thereof a therapeutically effective amount of a compound disclosed herein.

In some embodiments of a method disclosed herein, the subject is a human.

In another aspect, the present disclosure provides a kit comprising a pharmaceutical composition disclosed herein and instructions for using the composition to treat a subject suffering from a disease or condition mediated by an interaction between menin and another protein.

The novel features of the invention are set forth with particularity in the appended claims. A better understanding of the features and advantages of the present invention will be obtained by reference to the following detailed description that sets forth illustrative embodiments, in which the principles of the invention are utilized.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIG. 1 is an amino acid sequence of human menin, isoform 1 (SEQ ID NO: 1).

FIG. 2 is an amino acid sequence of human menin, isoform 2 (SEQ ID NO: 2).

FIG. 3 is an amino acid sequence of human menin, isoform 3 (SEQ ID NO: 3).

DETAILED DESCRIPTION OF THE INVENTION

Definitions

Unless defined otherwise, all technical and scientific terms used herein have the same meaning as is commonly understood by one of skill in the art to which this invention belongs.

"MLL fusion protein" refers to a protein with an N-terminal fragment of MLL fused with a partner protein. Non-limiting examples of a partner protein include 11q23, 11q23.3, 11q24, 1p13.1, 1p32 (EPS15), 21q22, 9p13.3, 9p22 (MLLT3/AF9), ABI1, ABI2, ACACA, ACTN4, AF1p, AFF1/AF4, AFF3/LAF4, AFF4/AF5, AKAP13, AP2A2, ARHGEF12, ARHGEF17, BCL9L, BTBD18, BUD13, C2CD3, CASC5, CASP8AP2, CBL, CBP, CEP164, CEP170B, CREBBP, DCP1A, DCPS, EEFSEC/SELB, ELL, EPS15, FLNA, FNBP1, FOXO3, GAS7, GMPS, KIAA1524, LAMC3, LOC100131626, MAML2, ME2, MLLT1/ENL, MLLT10/AF10, MLLT11/AF1Q, MLLT3/AF9, MLLT4/AF6, MLLT6/AF17, MYH11, MYO1F, NA, NEBL, NRIP3, PDS5A, PICALM, PRPF19, PTD, RUNDC3B, SEPT11, SEPT2, SEPT5, SEPT6, SEPT9, SMAP1, TET1, TNRC18, TOP3A, VAV1, and Xq26.3 (CT45A2). MLL fusion proteins may be created through the joining of a gene that codes for an MLL protein and a gene that codes for a partner protein creating a fusion gene. Translation of this fusion gene may result in a single or multiple polypeptides with functional properties derived from each of the original proteins.

"Amino" refers to the —$NH_2$ moiety.

"Carbonyl" refers to a moiety of the formula —C(=O)—.

"Carboxy" or "carboxyl" refers to the —$CO_2H$ moiety.

"Cyano" refers to the —CN moiety.

"Hydroxy" or "hydroxyl" refers to the —OH moiety.

"Imino" refers to the =NH moiety. Unless stated otherwise specifically in the specification, an imino group is optionally substituted.

"Nitro" refers to the —$NO_2$ moiety.

"Oxo" refers to the =O moiety.

"Thioxo" refers to the =S moiety.

"Acyl" refers to the group —C(=O)$R_a$, where $R_a$ is selected from the group consisting of alkyl, cycloalkyl, aryl, heteroaryl (bonded through a ring carbon), heteroalkyl, and heterocyclylalkyl. Unless stated otherwise specifically in the specification, an acyl group is optionally substituted.

"Alkyl" refers to a straight or branched hydrocarbon chain moiety consisting solely of carbon and hydrogen atoms, which is saturated or unsaturated (i.e., contains one or more double and/or triple bonds), having from one to twelve carbon atoms ($C_1$-$C_{12}$ alkyl), preferably one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Alkyl includes alkenyls (one or more carbon-carbon double bonds) and alkynyls (one or more carbon-carbon triple bonds). Unless stated otherwise specifically in the specification, an alkyl group is optionally substituted.

"Alkoxy" refers to a moiety of the formula —$OR_a$ where $R_a$ is an alkyl group as defined herein containing one to twelve carbon atoms. Unless stated otherwise specifically in the specification, an alkoxy group is optionally substituted.

"Alkylamino" refers to a moiety of the formula —$NHR_a$ or —$NR_aR_b$ where $R_a$ and $R_b$ are each independently an alkyl group as defined herein containing one to twelve carbon atoms. Unless stated otherwise specifically in the specification, an alkylamino group is optionally substituted.

"Alkylaminoalkyl" refers to an alkyl moiety comprising at least one alkylamino substituent. The alkylamino substituent can be on a tertiary, secondary or primary carbon. Unless stated otherwise specifically in the specification, an alkylaminoalkyl group is optionally substituted.

"Amide" or "amido" refers to a moiety with formula —C(=O)$NR_aR_b$ or —$NR_aC$(=O) $R_b$, where $R_a$ and $R_b$ are each independently selected from the group consisting of hydrogen, alkyl, cycloalkyl, aryl, heteroaryl (bonded through a ring carbon), heteroalkyl, and heterocyclylalkyl, each of which moiety may itself be optionally substituted. In some embodiments, it is a $C_1$-$C_4$ amido or amide group, which includes the amide carbonyl in the total number of carbons in the group. The $R_aR_b$ of —$NR_aR_b$ of the amide may optionally be taken together with the nitrogen to which it is attached to form a 4-, 5-, 6-, or 7-membered ring. Unless stated otherwise specifically in the specification, an amido group is optionally substituted.

"Aminoalkyl" refers to an alkyl moiety comprising at least one amino substituent. The amino substituent can be on a tertiary, secondary or primary carbon. Unless stated otherwise specifically in the specification, an aminoalkyl group is optionally substituted.

"Aminocarbonyl" refers to an amide moiety of the formula —C(=O)$NR_aR_b$, where $R_a$ and $R_b$ are each independently H or alkyl. Unless stated otherwise specifically in the specification, an aminocarbonyl group is optionally substituted.

"Aryl" refers to a hydrocarbon ring system moiety comprising 6 to 18 carbon atoms and at least one aromatic ring. For purposes of this invention, the aryl moiety is a monocyclic, bicyclic, tricyclic, or tetracyclic ring system, which may include fused or bridged ring systems. Aryl moieties include, but are not limited to, aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl groups that are optionally substituted.

"Aralkyl" refers to a moiety of the formula —$R_b$—$R_c$ where $R_b$ is an alkylene chain as defined herein and $R_c$ is one or more aryl moieties as defined herein, for example, benzyl, diphenylmethyl, and the like. Unless stated otherwise specifically in the specification, an aralkyl group is optionally substituted.

"Aralkylamino" refers to a aralkyl-$NR_a$— moiety, where $R_a$ is H or alkyl. Unless stated otherwise specifically in the specification, an aralkylamino is optionally substituted.

"Aralkyloxy" refers to an aralkyl-O— moiety. Unless stated otherwise specifically in the specification, an aralkyloxy is optionally substituted.

"Arylamino" refers to a —$NR_a$-aryl moiety, where $R_a$ is H or alkyl. Unless stated otherwise specifically in the specification, an arylamino is optionally substituted.

"Aryloxy" refers to an —O-aryl moiety. Unless stated otherwise specifically in the specification, an aryloxy is optionally substituted.

"Bicycloalkyl" refers to a moiety with two cycloalkyl moieties, that have one or more atoms in common. If the cycloalkyl moieties have exactly one atom in common they are said to be "spiro". Examples include, but are not limited to, spiro[2.2]pentane, spiro[5.5]undecane, spiro[4.5]decane, spiro[3.6]decane, and the like. If the cycloalkyl moieties have exactly two adjacent atoms in common they are said to be "fused". Examples include, but are not limited to, bicyclo[3.1.0]hexyl, perhydronaphthyl, and the like. If the cycloalkyl moieties have more than two atoms in common they are said to be "bridged". Examples include, but are not limited to, tricyclo[3.3.1.1]decyl ("adamantyl"), bicyclo[1.1.1]pentyl, bicyclo[2.2.1]heptyl ("norbornyl"), bicyclo[2.2.2]octyl, and the like. Unless stated otherwise specifically in the specification, a bicycloalkyl is optionally substituted.

"Carboxyalkyl" refers to a moiety of the formula —$R_b$—$R_c$ where $R_b$ is an alkylene chain as defined herein and $R_c$ is a carboxy group as defined herein. Unless stated otherwise specifically in the specification, carboxyalkyl group is optionally substituted.

"Cyanoalkyl" refers to a moiety of the formula —$R_b$—$R_c$ where $R_b$ is an alkylene chain as defined herein and $R_c$ is a cyano group as defined herein. Unless stated otherwise specifically in the specification, a cyanoalkyl group is optionally substituted.

"Cycloalkyl" or "carbocyclic ring" refers to a non-aromatic monocyclic or polycyclic hydrocarbon moiety, which may include fused, spiro, or bridged ring systems, having from three to fifteen carbon atoms, preferably having from three to ten carbon atoms, and which is saturated or unsaturated and attached to the rest of the molecule by a single bond. Monocyclic cycloalkyl moieties include, for example, cyclopropyl, cyclobutyl, cyclopentyl, cyclopentenyl, cyclohexyl, cyclohexenyl, cycloheptyl, and cyclooctyl. Polycyclic cycloalkyl moieties include, for example, adamantyl, norbornyl, decalinyl, 7,7-dimethyl-bicyclo[2.2.1]heptanyl, and the like. A "cycloalkenyl" is a cycloalkyl comprising one or more carbon-carbon double bonds within the ring, such as cyclopentenyl and cyclohexenyl. Unless otherwise stated specifically in the specification, a cycloalkyl group is optionally substituted.

"Carbocycle" refers to a saturated, unsaturated or aromatic ring in which each atom of the ring is a carbon atom. Carbocycle may include 3- to 10-membered monocyclic rings, 6- to 12-membered bicyclic rings, and 6- to 12-membered bridged rings. Each ring of a bicyclic carbocycle may be selected from saturated, unsaturated, and aromatic rings. In some embodiments, the carbocycle is an aryl. In some embodiments, the carbocycle is a cycloalkyl. In some embodiments, the carbocycle is a cycloalkenyl. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, are included in the definition of carbocyclic. Exemplary carbocycles include cyclopentyl, cyclohexyl, cyclohexenyl, adamantyl, phenyl, indanyl, and naphthyl. Unless stated otherwise specifically in the specification, a carbocycle is optionally substituted by one or more substituents such as those substituents described herein.

"Cycloalkylalkyl" refers to a moiety of the formula —$R_b R_d$ where $R_b$ is an alkylene chain as defined herein and $R_d$ is a cycloalkyl moiety as defined herein. Unless stated otherwise specifically in the specification, a cycloalkylalkyl group is optionally substituted.

"Cycloalkylalkylamino" refers to a cycloalkylalkyl-$NR_a$— moiety, where $R_a$ is H or alkyl and where the cycloalkylalkyl moiety is attached via a carbon atom to nitrogen, wherein the nitrogen functions as a linker to attach the moiety to the remainder of the molecule. Unless stated otherwise specifically in the specification, a cycloalkylalkylamino is optionally substituted.

"Cycloalkylalkyloxy" refers to a —O-cycloalkylalkyl moiety, where the cycloalkylalkyl moiety is attached via a carbon atom to oxygen, wherein the oxygen functions as a linker to attach the moiety to the remainder of the molecule. Unless stated otherwise specifically in the specification, a cycloalkylalkyloxy is optionally substituted.

"Cycloalkylamino" refers to a —$NR_a$-cycloalkyl moiety, where $R_a$ is H or alkyl. Unless stated otherwise specifically in the specification, a cycloalkylamino is optionally substituted.

"Cycloalkyloxy" refers to an —O-cycloalkyl moiety. Unless stated otherwise specifically in the specification, a cycloalkyloxy is optionally substituted.

"Halo" or "halogen" refers to fluoro, chloro, bromo, or iodo.

"Haloalkyl" refers to an alkyl group, as defined herein, that is substituted by one or more halo atoms, as defined herein, e.g., trifluoromethyl, difluoromethyl, fluoromethyl, trichloromethyl, —$CH_2CF_3$, —$CH_2CHF_2$, —$CH_2CH_2F$, —$CHFCF_3$, —$CHFCHF_2$, —$CHFCH_2F$, —$CHFCH_3$, —$CF_2CF_3$, —$CF_2CHF_2$, —$CF_2CH_2F$, —$CF_2CH_3$, —$CH_2CF_2CH_3$, —$CH_2CHFCH_3$, 3-bromo-2-fluoropropyl, 1,2-dibromoethyl, and the like. Unless stated otherwise specifically in the specification, a haloalkyl group is optionally substituted.

As used herein, the term "heteroatom" or "ring heteroatom" is meant to include any element other than carbon or hydrogen. Preferred heteroatoms are oxygen (O), nitrogen (N), sulfur (S), and phosphorus (P).

"Heteroalkyl," by itself or in combination with another term, means, unless otherwise stated, a straight or branched chain; monocyclic or polycyclic moiety, which may include fused or bridged ring systems; or any combination thereof, comprising at least one carbon atom and at least one heteroatom, such as O, N, P, Si and S, wherein one or more heteroatoms may be oxidized. Heteroatom(s) may be positioned within the alkyl moiety, e.g., —$CH_2$—O—$CH_2$—; at a point of connectivity with the remainder of the molecule, e.g., —$SO_2CH(CH_3)CH_2$—; or a combination thereof, e.g., —$NH_2CH_2CH_2SO_2CH_2$—. Unless stated otherwise specifically in the specification, a heteroalkyl group is optionally substituted.

"Heteroaryl" refers to a 5- to 14-membered ring system moiety comprising one to thirteen carbon atoms; one to six heteroatoms such as nitrogen, oxygen, and sulfur; and one or multiple rings wherein at least one ring is aromatic. For purposes of this invention, the heteroaryl group may be a monocyclic, bicyclic, tricyclic, or tetracyclic ring system, which may include fused or bridged ring systems and one or more heteroatoms may be oxidized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group is optionally substituted.

"Heteroarylalkyl" refers to a moiety of the formula —$R_bR_f$ where $R_b$ is an alkylene chain as defined herein and $R_f$ is a heteroaryl group as defined herein. Unless stated otherwise specifically in the specification, a heteroarylalkyl group is optionally substituted.

"Heteroarylalkylamino" refers to a heteroarylalkyl-$NR_a$— moiety, where $R_a$ is H or alkyl. Unless stated otherwise specifically in the specification, an heteroarylalkylamino is optionally substituted.

"Heteroarylalkyloxy" refers to an heteroarylalkyl-O— moiety. Unless stated otherwise specifically in the specification, a heteroarylalkyloxy is optionally substituted.

"Heteroarylamino" refers to a —$NR_a$-heteroaryl moiety, where $R_a$ is H or alkyl. Unless stated otherwise specifically in the specification, a heteroarylamino is optionally substituted.

"Heteroaryloxy" refers to an —O-heteroaryl moiety. Unless stated otherwise specifically in the specification, an heteroaryloxy is optionally substituted.

"Heterobicycloalkyl" refers to a bicycloalkyl structure in which at least one carbon ring atom is replaced with a heteroatom such as oxygen, nitrogen, and sulfur. Unless stated otherwise specifically in the specification, a heterobicycloalkyl is optionally substituted.

"Heterocyclyl" or "heterocyclic ring" refers to a 3- to 18-membered non-aromatic ring which consists of two to twelve carbon atoms and from one to six heteroatoms such as nitrogen, oxygen, and sulfur. Unless stated otherwise specifically in the specification, the heterocyclyl group is a monocyclic, bicyclic, tricyclic, or tetracyclic ring system, which may include fused or bridged ring systems; the heteroatoms may be optionally oxidized; and the heterocyclyl may be unsaturated or saturated. Examples of such heterocyclyl moieties include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclyl group is optionally substituted.

"Heterocycle" refers to a saturated, unsaturated or aromatic ring comprising one or more heteroatoms. Exemplary heteroatoms include N, O, Si, P, B, and S atoms. Heterocycles include 3- to 10-membered monocyclic rings, 6- to 12-membered bicyclic rings, and 6- to 12-membered bridged rings. Each ring of a bicyclic heterocycle may be selected from saturated, unsaturated, and aromatic rings. The heterocycle may be attached to the rest of the molecule through any atom of the heterocycle, valence permitting, such as a carbon or nitrogen atom of the heterocycle. In some embodiments, the heterocycle is a heteroaryl. In some embodiments, the heterocycle is a heterocycloalkyl. In an exemplary embodiment, a heterocycle, e.g., pyridyl, may be fused to a saturated or unsaturated ring, e.g., cyclohexane, cyclopentane, or cyclohexene.

"Heterocyclylalkyl" or "heterocycloalkyl" refers to a moiety of the formula —$R_bR_c$ where $R_b$ is an alkylene chain as defined herein and $R_e$ is a heterocyclyl moiety as defined herein, and if the heterocyclyl is a nitrogen-containing heterocyclyl, the heterocyclyl is optionally attached to the alkyl moiety at the nitrogen atom. Unless stated otherwise specifically in the specification, a heterocyclylalkyl group is optionally substituted.

"Heterocyclylalkylamino" refers to a heterocyclylalkyl-$NR_a$— moiety, where $R_a$ is H or alkyl and where the heterocyclylalkyl moiety is attached via a carbon atom to nitrogen, wherein the nitrogen functions as a linker to attach the moiety to the remainder of the molecule. Unless stated otherwise specifically in the specification, a heterocyclylalkylamino is optionally substituted.

"Heterocyclylalkyloxy" refers to a —O-heterocycloalkyl moiety, where the heterocyclylalkyl moiety is attached via a carbon atom to oxygen, wherein the oxygen functions as a linker to attach the moiety to the remainder of the molecule. Unless stated otherwise specifically in the specification, a heterocyclylalkyloxy is optionally substituted.

"Heterocyclylamino" refers to a —$NR_a$-heterocyclyl moiety, where $R_a$ is H or alkyl and where the heterocyclyl moiety is attached via a carbon atom to nitrogen, wherein the nitrogen functions as a linker to attach the moiety to the remainder of the molecule. Unless stated otherwise specifically in the specification, a heterocyclylamino is optionally substituted.

"Heterocyclyloxy" refers to an —O-heterocyclyl moiety, where the heterocyclyl moiety is attached via a carbon atom to oxygen, wherein the oxygen functions as a linker to attach the moiety to the remainder of the molecule. Unless stated otherwise specifically in the specification, a heterocyclyloxy is optionally substituted.

"Hydroxyalkyl" or "hydroxylalkyl" refers to an alkyl group comprising at least one hydroxyl substituent. The —OH substituent may be on a primary, secondary, or tertiary carbon. Unless stated otherwise specifically in the specification, a hydroxylalkyl group is optionally substituted.

"N-heteroaryl" refers to a heteroaryl moiety as defined herein containing at least one nitrogen and where the point of attachment of the heteroaryl moiety to the rest of the molecule is through a nitrogen atom in the heteroaryl ring. Unless stated otherwise specifically in the specification, an N-heteroaryl group is optionally substituted.

"N-heterocyclyl" refers to a heterocyclyl moiety as defined herein containing at least one nitrogen and where the point of attachment of the heterocyclyl moiety to the rest of the molecule is through a nitrogen atom in the heterocyclyl ring. Unless stated otherwise specifically in the specification, a N-heterocyclyl group is optionally substituted.

"Thioalkyl" refers to a moiety of the formula —$SR_a$ where $R_a$ is an alkyl moiety as defined herein containing one to twelve carbon atoms. Unless stated otherwise specifically in the specification, a thioalkyl group is optionally substituted.

"Alkylene" or "alkylene chain" refers to a straight or branched divalent hydrocarbon chain linking two groups in a molecule, which may be saturated or unsaturated (i.e., contains one or more double and/or triple bonds), and have from one to twelve carbon atoms, preferably one to eight carbon atoms ($C_1$-$C_8$ alkylene) or one to six carbon atoms ($C_1$-$C_6$ alkylene), e.g., methylene, ethylene, propylene, n-butylene, ethenylene, propenylene, n-butenylene, propynylene, n-butynylene, and the like. The alkylene chain is attached to the rest of the molecule through a single or double bond. The points of attachment of the alkylene chain to the rest of the molecule may be through one carbon, e.g., methylene, or any two carbons within the chain, e.g., —$CH_2CH(CH_3)CH_2CH_2$—. Unless stated otherwise specifically in the specification, an alkylene chain is optionally substituted.

"Alkylenecarbonyl" refers to a moiety of the formula —C(=O)$R_a$—, where $R_a$ is an alkylene chain as defined herein. Unless stated otherwise specifically in the specification, an alkylenecarbonyl is optionally substituted.

"Alkenylene" is an unsaturated alkylene, as defined herein, which comprises one or more carbon-carbon double bonds. Unless stated otherwise specifically in the specification, an alkenylene is optionally substituted.

"Alkenylenecarbonyl" refers to an unsaturated alkylenecarbonyl, as defined herein, which comprises one or more carbon-carbon double bonds. Unless stated otherwise specifically in the specification, an alkenylenecarbonyl is optionally substituted.

"Arylene" refers to a divalent aryl group which links one part of the molecule to another part of the molecule. Unless stated specifically otherwise, an arylene is optionally substituted.

"Heteroalkylene" refers to an alkylene group comprising at least one heteroatom (e.g., N, O or S). In some embodiments, the heteroatom is within the alkylene chain (i.e., the heteroalkylene comprises at least one carbon-heteroatom-carbon bond). In other embodiments, the heteroatom is at a terminus of the alkylene and joins the alkylene to the remainder of the molecule (e.g., M1-H-A-M2, where M1 and M2 are portions of a molecule, H is a heteroatom and A is an alkylene). A heteroalkylene may have both internal and terminal heteroatoms, e.g., —$OCH_2CH_2OCH_2CH_2O$—. Unless stated otherwise specifically in the specification, a heteroalkylene is optionally substituted.

"Heteroalkylenecarbonyl" refers to a moiety of the formula —C(=O)$R_a$—, where $R_a$ is a heteroalkylene chain as defined herein. Unless stated otherwise specifically in the specification, a heteroalkylenecarbonyl is optionally substituted.

"Heteroarylene" refers to a divalent heteroaryl group which links one part of the molecule to another part of the molecule. Unless stated specifically otherwise, a heteroarylene is optionally substituted.

"Heteroarylenecarbonyl" refers to a moiety of the formula —C(=O)$R_a$—, wherein $R_a$ is a heteroarylene as defined herein. Unless stated specifically otherwise, a heteroarylenecarbonyl is optionally substituted.

"Heterocyclylalkylene" refers to a divalent heterocyclyl group which links one part of the molecule to another part of the molecule. Unless stated specifically otherwise, a heterocycloalkylene is optionally substituted.

"Heterocyclylalkylenecarbonyl" refers to a moiety of the formula —C(=O)$R_a$—, wherein $R_a$ is a heterocycloalkylene as defined herein. Unless stated specifically otherwise, a heterocycloalkylenecarbonyl is optionally substituted.

The term "substituted" used herein means any of the above groups (e.g., amino, carboxy, hydroxyl, imino, acyl, alkyl, alkoxy, alkylamino, alkylaminoalkyl, amide, aminoalkyl, aminocarbonyl, aryl, aralkyl, aralkylamino, aralkyloxy, arylamino, aryloxy, bicycloalkyl, carboxyalkyl, cyanoalkyl, cycloalkyl, cycloalkylalkyl, cycloalkylalkylamino, cycloalkylalkyloxy, cycloalkylamino, cycloalkyloxy, halo, haloalkyl, heteroatom, heteroalkyl, heteroaryl, heteroarylalkyl, heteroarylalkylamino, heteroarylalkyloxy, heteroarylamino, heteroaryloxy, heterobicycloalkyl, heterocyclyl, heterocyclylalkyl, heterocyclyl alkylamino, heterocyclylalkyloxy, heterocyclylamino, heterocyclyloxy, hydroxyalkyl, N-heteroaryl, N-heterocyclyl, thioalkyl, alkylene, alkylenecarbonyl, alkenylene, alkenylenecarbonyl, arylene, heteroalkylene, heteroalkylenecarbonyl, heteroarylene, heteroarylenecarbonyl, heterocyclylalkylene, and/or heterocyclylalkylenecarbonyl), wherein at least one hydrogen atom is replaced by a bond to a non-hydrogen atom such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, thiourea groups, sulfone groups such as alkyl sulfone groups, sulfonyl groups such as sulfonamide groups and sulfonylalkyl groups such as sulfonylmethane, and sulfoxide groups such as alkyl sulfoxide groups; a nitrogen atom in groups such as amino, amines, amides, alkylamines, dialkylamines, arylamines, alkylarylamines, diarylamines, N-oxides, imides, urea, and enamines; a silicon atom in groups such as trialkylsilyl groups, dialkylarylsilyl groups, alkyldiarylsilyl groups, and triarylsilyl groups; a phosphorus atom in groups such as dialkylphosphine oxide groups, phosphine oxide groups, phosphine groups, phosphate groups, phosphonate groups, and phosphinate groups; and other heteroatoms in various other groups. "Substituted" also means any of the above groups in which one or more hydrogen atoms are replaced by a higher-order bond (e.g., a double- or triple-bond) to a carbon atom or a heteroatom such as oxygen in oxo, carbonyl, carboxyl, and ester groups; and nitrogen in groups such as imines, oximes, hydrazones, and nitriles. "Substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, —$SO_2NR_gR_h$, —C(=O)$R_g$, —C(=O)O$R_g$, —C(=O)$NR_gR_h$, —$CH_2SO_2R_g$, or —$CH_2SO_2NR_gR_h$, where $R_g$ and $R_h$ are independently hydrogen, alkyl, alkoxy, alkylamino, thioalkyl, aryl, aralkyl, cycloalkyl, cycloalkylalkyl, haloalkyl, heteroalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, carbonyl, carboxy, cyano, hydroxyl, imino, nitro, oxo, thioxo, acyl, alkyl, alkoxy, alkylamino, alkylaminoalkyl, amide, aminoalkyl, aminocarbonyl, aryl, aralkyl, aralkylamino, aralkyloxy, arylamino, aryloxy, bicycloalkyl, carboxyalkyl, cyanoalkyl, cycloalkyl, cycloalkylalkyl, cycloalkylalkylamino, cycloalkylalkyloxy, cycloalkylamino, cycloalkyloxy, halo, haloalkyl, heteroatom, heteroalkyl, heteroaryl, heteroarylalkyl, heteroarylalkylamino, heteroarylalkyloxy, heteroarylamino, heteroaryloxy, heterobicycloalkyl, heterocyclyl, heterocyclylalkyl, heterocyclylalkylamino, heterocyclylalkyloxy, heterocyclylamino, heterocyclyloxy, hydroxyalkyl, N-heteroaryl, N-heterocyclyl, thioalkyl, alkylene, alkylenecarbonyl, alkenylene, alkenylenecarbonyl, arylene, heteroalkylene, heteroalkylenecarbonyl, heteroarylene, heteroarylenecarbonyl, heterocyclylalkylene, heterocyclylalkylenecarbonyl, trimethylsilanyl, dialkylphosphine oxide, —$OR^a$, —$SR^a$, —OC(O)—$R^a$, —$N(R^a)_2$, —C(O)$R^a$, —C(O)O$R^a$, —C(O)$N(R^a)_2$, —$N(R^a)$C(O)O$R^a$, —$N(R^a)$C(O)$R^a$, —$N(R^a)$S(O)$_tR^a$ (where t is 1 or 2), —S(O)$_t$O$R^a$ (where t is 1 or 2), —S(O)$_tN(R^a)_2$ (where t is 1 or 2), —PO($R^a$)$_2$, or —PO(O$R^a$)$_2$ group, where each $R^a$ is independently hydrogen, alkyl, haloalkyl, cycloalkyl, cycloalkylalkyl, aryl, aralkyl, heterocyclyl, heterocyclylalkyl, heteroaryl or heteroarylalkyl group. In addition, each of the foregoing substituents is optionally substituted with one or more of the above substituents.

The term "effective amount" or "therapeutically effective amount" refers to that amount of a compound described herein that is sufficient to affect the intended application, including but not limited to disease treatment, as defined below. The therapeutically effective amount may vary depending upon the intended treatment application (in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

As used herein, "treatment" or "treating" refers to an approach for obtaining beneficial or desired results with respect to a disease, disorder, or medical condition including but not limited to a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. In certain embodiments, for prophylactic benefit, the compositions are administered to a subject at risk of developing a particular disease, or to a subject reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "co-administration," "administered in combination with," and their grammatical equivalents, as used herein, encompass administration of two or more agents to an animal, including humans, so that both agents and/or their metabolites are present in the subject at the same time. Co-administration includes simultaneous administration in separate compositions, administration at different times in separate compositions, or administration in a composition in which both agents are present.

"Pharmaceutically acceptable salt" includes both pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise desirable, and which are formed with inorganic acids such as, but are not limited to, hydrochloric acid, hydrobromic acid, sulfuric acid, nitric acid, phosphoric acid and the like, or organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise desirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethyl aminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

The terms "antagonist" and "inhibitor" are used interchangeably, and they refer to a compound having the ability to inhibit a biological function (e.g., activity, expression, binding, protein-protein interaction) of a target protein (e.g., menin, MLL1, MLL2, and/or a MLL fusion protein). Accordingly, the terms "antagonist" and "inhibitor" are defined in the context of the biological role of the target protein. While preferred antagonists herein specifically interact with (e.g., bind to) the target, compounds that inhibit a biological activity of the target protein by interacting with other members of the signal transduction pathway of which the target protein is a member are also specifically included within this definition. A preferred biological activity inhibited by an antagonist is associated with the development, growth, or spread of a tumor.

The term "agonist" as used herein refers to a compound having the ability to initiate or enhance a biological function of a target protein, whether by inhibiting the activity or expression of the target protein. Accordingly, the term "agonist" is defined in the context of the biological role of the target polypeptide. While preferred agonists herein specifically interact with (e.g., bind to) the target, compounds that initiate or enhance a biological activity of the target polypeptide by interacting with other members of the signal transduction pathway of which the target polypeptide is a member are also specifically included within this definition.

As used herein, "agent" or "biologically active agent" refers to a biological, pharmaceutical, or chemical compound. Non-limiting examples include a simple or complex organic or inorganic molecule, a peptide, a protein, an oligonucleotide, an antibody, an antibody derivative, antibody fragment, a vitamin derivative, a carbohydrate, a toxin, and a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like.

"Signal transduction" is a process during which stimulatory or inhibitory signals are transmitted into and within a cell to elicit an intracellular response. A modulator of a signal transduction pathway refers to a compound which modulates the activity of one or more cellular proteins mapped to the same specific signal transduction pathway. A modulator may augment (agonist) or suppress (antagonist) the activity of a signaling molecule.

An "anti-cancer agent", "anti-tumor agent" or "chemotherapeutic agent" refers to any agent useful in the treatment of a neoplastic condition. One class of anti-cancer agents comprises chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

The term "cell proliferation" refers to a phenomenon by which the cell number has changed as a result of division. This term also encompasses cell growth by which the cell morphology has changed (e.g., increased in size) consistent with a proliferative signal.

"Subject" refers to an animal, such as a mammal, for example a human. The methods described herein can be useful in both human therapeutics and veterinary applications. In some embodiments, the subject is a mammal, and in some embodiments, the subject is human.

"Mammal" includes humans and both domestic animals such as laboratory animals and household pets (e.g., cats, dogs, swine, cattle, sheep, goats, horses, rabbits), and non-domestic animals such as wildlife and the like.

"Prodrug" is meant to indicate a compound that may be converted under physiological conditions or by solvolysis to a biologically active compound described herein (e.g., compound of Formula VII). Thus, the term "prodrug" refers to a precursor of a biologically active compound that is pharmaceutically acceptable. In some aspects, a prodrug is inactive when administered to a subject but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam); Higuchi, T., et al., "Pro-drugs as Novel Delivery Systems," (1987) A.C.S. Symposium Series, Vol. 14; and Bioreversible Carriers in Drug Design, ed. Edward B. Roche, American Pharmaceutical Association and Pergamon Press) each of which is incorporated in full by reference herein. The term "prodrug" is also meant to include any covalently bonded carriers, which release the active compound in vivo when such prodrug is administered to a mammalian subject. Prodrugs of an active compound, as described herein, are typically prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of a hydroxy functional group, or acetamide, formamide and benzamide derivatives of an amine functional group in the active compound and the like.

The term "in vivo" refers to an event that takes place in a subject's body.

The term "in vitro" refers to an event that takes places outside of a subject's body. For example, an in vitro assay encompasses any assay run outside of a subject. In vitro assays encompass cell-based assays in which cells alive or dead are employed. In vitro assays also encompass a cell-free assay in which no intact cells are employed.

In certain embodiments, the compounds disclosed herein are isotopically labeled. Isotopically-labeled compounds (e.g., an isotopologue) may have one or more atoms replaced by an atom having a different atomic mass or mass number. Non-limiting examples of isotopes that can be incorporated into the disclosed compounds include isotopes of hydrogen, carbon, nitrogen, oxygen, phosphorous, sulfur, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. Certain isotopically-labeled compounds, for example, those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection. These radiolabeled compounds could be useful to help determine or measure the effectiveness of the compounds, by characterizing, for example, the site or mode of action, or binding affinity to a pharmacologically important site of action. Substitution with heavier isotopes such as deuterium, i.e. $^{2}H$, may afford certain therapeutic advantages resulting from greater metabolic stability, for example, increased in vivo half-life or reduced dosage requirements, and hence are preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds can generally be prepared by conventional techniques known to those skilled in the art or by processes analogous to those described in the Preparations and Examples as set out below using an appropriate isotopically-labeled reagent in place of the non-labeled reagent.

"Optional" or "optionally" means that the subsequently described event of circumstances may or may not occur, and that the description includes instances where the event or circumstance occurs and instances in which it does not. For example, "optionally substituted aryl" means that the aryl group may or may not be substituted and that the description includes both substituted aryl groups and aryl groups having no substitution.

"Pharmaceutically acceptable carrier, diluent or excipient" includes without limitation any adjuvant, carrier, excipient, glidant, sweetening agent, diluent, preservative, dye, colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

The compounds of the invention, or their pharmaceutically acceptable salts may contain one or more asymmetric centers and may thus give rise to enantiomers, diastereomers, and other stereoisomeric forms that are defined, in terms of absolute stereochemistry, as (R)- or (S)- or, as (D)- or (L)- for amino acids. The present invention is meant to include all such possible isomers, as well as their racemic and optically pure forms. A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers.

A "tautomer" refers to a proton shift from one atom of a molecule to another atom of the same molecule. The present invention includes tautomers of any the compounds and all tautomeric forms are also intended to be included.

Compounds

The present disclosure provides compounds for modulating the interaction of menin with proteins such as MLL1, MLL2 and MLL-fusion oncoproteins. In certain embodiments, the disclosure provides compounds and methods for inhibiting the interaction of menin with its upstream or downstream signaling molecules including but not limited to MLL1, MLL2 and MLL-fusion oncoproteins. Compounds of the disclosure may be used in methods for the treatment of a wide variety of cancers and other diseases associated with one or more of MLL1, MLL2, MLL fusion proteins, and menin. In certain embodiments, a compound of the disclosure covalently binds menin and inhibits the interaction of menin with MLL. In certain embodiments, a compound of the disclosure interacts non-covalently with menin and inhibits the interaction of menin with MLL.

Compounds of the disclosure may be used in methods for treating a wide variety of diseases associated with MLL1, MLL2, MLL fusion proteins, and menin. In certain embodiments, a compound of the disclosure interacts non-covalently with menin and inhibits the interaction of menin with MLL. In certain embodiments, a compound of the disclosure covalently binds menin and inhibits the interaction of menin with MLL.

In an aspect, the invention provides compounds which are capable of selectively binding to the menin protein and/or modulating menin's interaction with an MLL protein (e.g., MLL1, MLL2, MLL fusion protein). In some embodiments, the compounds modulate the menin protein by binding to or interacting with one or more amino acids and/or one or more metal ions. Some compounds may occupy the F9 and/or P13 pocket on menin. The binding of these compounds may disrupt menin or MLL (non-limiting examples include MLL1, MLL2, and MLL fusion proteins) downstream signaling.

In some embodiments, provided herein is a compound having the structure of Formula VII:

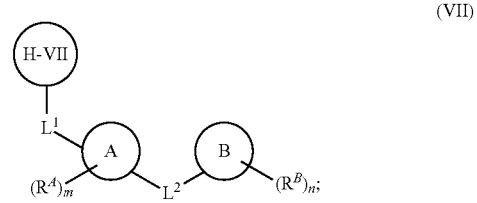

(VII)

or a pharmaceutically acceptable salt thereof, wherein:
H-VII is

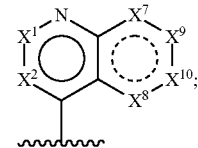

each of $X^1$ and $X^2$ is independently $CR^2$ or N;
each of $X^7$, $X^8$, $X^9$, and $X^{10}$ is independently $CR^{16}$, $CR^{17}R^{18}$, N, $NR^{19}$, O, or S;
each of $L^1$ and $L^2$ is independently a bond, carbonyl, O, S, $-NR^5-$, $-NR^6CH_2-$, $-NR^6C(=O)-$, $-NR^6SO_2-$, alkylene, alkenylene, heteroalkylene, alkylenecarbonyl, alkenylenecarbonyl, or heteroalkylenecarbonyl;
A is a bond, a 3-7 membered saturated ring, or a 3-7 membered unsaturated ring;
m is an integer from 0 to 12;
B is selected from B-I, B-II, B-III, and B-IV;
wherein B is connected at any ring atom to $L^2$;
B-I

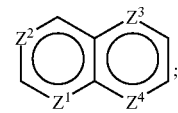

B-II is

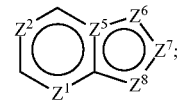

B-III is

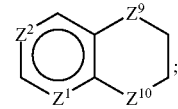

B-IV is

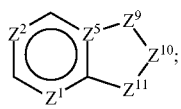

each of $Z^1$, $Z^2$, $Z^3$, and $Z^4$ is independently $CR^7$, N, or $NR^9$; $Z^5$ is C or N;

each of $Z^6$, $Z^7$, and $Z^8$ is independently $CR^8$, N, $NR^9$, O, or S;

each of $Z^9$, $Z^{10}$, and $Z^{11}$ is independently $CR^{10}$, $CR^{11}R^{12}$, $NR^{13}$, O, or S; n is an integer from 0 to 6;

each of $R^2$, $R^5$, $R^6$, $R^7$, $R^8$, $R^9$, $R^{10}$, $R^{11}$, $R^{12}$, $R^{13}$, $R^{16}$, $R^{17}$, $R^{18}$, and $R^{19}$ is, at each occurrence, independently selected from H, halo, hydroxyl, amino, cyano, dialkylphosphine oxide, oxo, carboxyl, amido, acyl, alkyl, cycloalkyl, heteroalkyl, haloalkyl, aminoalkyl, hydroxyalkyl, alkoxy, alkylamino, cycloalkylalkyl, cycloalkyloxy, cycloalkylalkyloxy, cycloalkylamino, cycloalkylalkylamino, heterocyclyl, heterocyclylalkyl, heterocyclyloxy, heterocyclylalkyloxy, heterocyclylamino, heterocyclylalkylamino, aryl, aralkyl, aryloxy, aralkyloxy, arylamino, aralkylamino, heteroaryl, heteroarylalkyl, heteroaryloxy, heteroarylalkyloxy, heteroarylamino, and heteroarylalkylamino; and each of $R^A$ and $R^B$ is, at each occurrence, independently selected from halo, hydroxyl, amino, cyano, dialkylphosphine oxide, oxo, carboxyl, amido, acyl, alkyl, cycloalkyl, heteroalkyl, haloalkyl, aminoalkyl, hydroxyalkyl, alkoxy, alkylamino, cycloalkylalkyl, cycloalkyloxy, cycloalkylalkyloxy, cycloalkylamino, cycloalkylalkylamino, heterocyclyl, heterocyclylalkyl, heterocyclyloxy, heterocyclylalkyloxy, heterocyclylamino, heterocyclylalkylamino, aryl, aralkyl, aryloxy, aralkyloxy, arylamino, aralkylamino, heteroaryl, heteroarylalkyl, heteroaryloxy, heteroarylalkyloxy, heteroarylamino, and heteroarylalkylamino, wherein two $R^A$ groups or two $R^B$ groups attached to the same atom or different atoms can together optionally form a bridge or ring.

In various different embodiments, the compound has one of the structures set forth in one of the following tables. In various different embodiments, the compound comprises one or more of the structures set forth in one or more of the following tables.

Ring H-VII

In some cases, for a compound of Formula VII, H-VII is an optionally substituted 10-membered bicyclic heteroaryl. In some cases, H-VII has the structure:

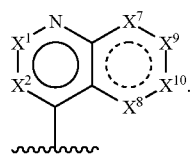

In some cases, each of $X^1$ and $X^2$ is independently $CR^2$ or N. In some cases, each of $X^7$, $X^8$, $X^9$, and $X^{10}$ is independently $CR^{16}$, $CR^{17}R^{18}$, N, $NR^{19}$, O, or S. In some cases, H-VII does not contain three or more adjacent ring N atoms. In some cases, the dashed circle indicates an aromatic, nonaromatic, unsaturated, or saturated ring. In some cases, the dashed circle indicates the presence of 0, 1, 2, or 3 double bonds in the ring. In some cases, the dashed circle indicates the presence of at least 1, 2, or 3 double bonds in the ring. In some cases, the dashed circle indicates the presence of up to 1, 2, or 3 double bonds in the ring. In some cases, H-VII is selected from a structure listed in Table Id. In some cases, H-VII is not one or more structures listed in Table Id.

In a compound of Formula VII, H-VII may contain one or more heteroatoms. In some cases, H-VII contains 0, 1, 2, 3, 4, 5, or 6 ring heteroatoms. In some cases, H-VII contains at least 1, 2, 3, 4, 5, or 6 ring heteroatoms. In some cases, H-VII contains up to 1, 2, 3, 4, 5, or 6 ring heteroatoms. In some cases, H-VII contains 0, 1, 2, 3, 4, or 5 ring N atoms. In some cases, H-VII contains at least 1, 2, 3, 4, or 5 ring N atoms. In some cases, H-VII contains up to 1, 2, 3, 4, or 5 ring N atoms. In some cases, H-VII contains 0, 1, or 2 ring O atoms. In some cases, H-VII contains at least 1 or 2 ring O atoms. In some cases, H-VII contains up to 1 or 2 ring O atoms. In some cases, H-VII contains 0, 1, or 2 ring S atoms. In some cases, H—VII contains at least 1 or 2 ring S atoms. In some cases, H-VII contains up to 1 or 2 ring S atoms. In some cases, H-VII contains 3, 4, 5, 6, 7, 8, or 9 ring carbon atoms. In some cases, H-VII contains at least 3, 4, 5, 6, 7, 8, or 9 ring carbon atoms. In some cases, H-VII contains up to 3, 4, 5, 6, 7, 8, or 9 ring carbon atoms.

TABLE 1d

Non-limiting examples of H-VII structures

| H-VII Number | H-VII Structure |
|---|---|
| H-VII | |
| H-VII-2 | |
| H-VII-3 | |
| H-VII-4 | |
| H-VII-5 | |

TABLE 1d-continued

Non-limiting examples of H-VII structures

| H-VII Number | H-VII Structure |
|---|---|
| H-VII-6 | |
| H-VII-7 | |
| H-VII-8 | |
| H-VII-9 | |
| H-VII-10 | |
| H-VII-11 | |
| H-VII-12 | |
| H-VII-13 | |
| H-VII-14 | |
| H-VII-15 | |
| H-VII-16 | |
| H-VII-17 | |
| H-VII-18 | |
| H-VII-19 | |
| H-VII-20 | |
| H-VII-21 | |
| H-VII-22 | |
| H-VII-23 | |

TABLE 1d-continued

Non-limiting examples of H-VII structures

| H-VII Number | H-VII Structure |
|---|---|
| H-VII-24 | 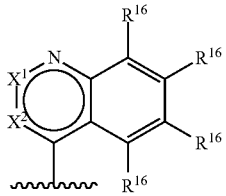 |
| H-VII-25 | 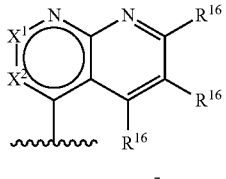 |
| H-VII-26 | 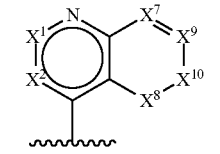 |
| H-VII-27 | 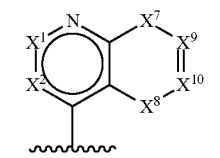 |
| H-VII-28 | 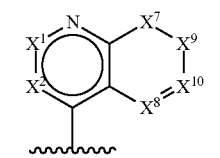 |

Ring A

In a compound of Formula VII, A may be a bond, a 3-7 membered saturated ring, or a 3-7 membered unsaturated ring. In some cases, A is aromatic, non-aromatic, saturated, or unsaturated. In some cases, A is an aryl, arylene, cycloalkyl, heterocyclyl, N-heterocyclyl, heterocyclylalkylene, heteroaryl, heteroarylene, or N-heteroaryl. In some cases, A is a 3, 4, 5, 6, or 7-membered ring. In some cases, A is at least a 3, 4, 5, 6, or 7-membered ring. In some cases, A is up to a 3, 4, 5, 6, or 7-membered ring. In some cases, A is a bond.

In a compound of Formula VII, A may contain one or more heteroatoms. In some cases, A contains 0, 1, 2, 3, or 4 ring heteroatoms. In some cases, A contains at least 1, 2, 3, or 4 ring heteroatoms. In some cases, A contains up to 1, 2, 3, or 4 ring heteroatoms. In some cases, A contains 0, 1, 2, 3, or 4 ring N atoms. In some cases, A contains at least 1, 2, 3, or 4 ring N atoms. In some cases, A contains up to 1, 2, 3, or 4 ring N atoms. In some cases, A contains 0, 1, 2, or 3 ring O atoms. In some cases, A contains at least 1, 2, or 3 ring O atoms. In some cases, A contains up to 1, 2, or 3 ring 0 atoms. In some cases, A contains 0, 1, or 2 ring S atoms. In some cases, A contains at least 1 or 2 ring S atoms. In some cases, A contains up to 1 or 2 ring S atoms. In some cases, A contains 2, 3, 4, 5, 6, or 7 ring carbon atoms. In some cases, A contains at least 2, 3, 4, 5, 6, or 7 ring carbon atoms. In some cases, A contains up to 2, 3, 4, 5, 6, or 7 ring carbon atoms.

In a compound of Formula VII, A may be connected at any ring atom to $L^1$ or $L^2$ (e.g., by replacing a hydrogen connected to a ring atom with a bond to $L^1$ or $L^2$). In some cases, A is connected at the same ring atom to $L^1$ and $L^2$. In some cases, A is connected at different ring atoms to $L^1$ and $L^2$. In some cases, A is connected at a ring heteroatom to $L^1$ and/or $L^2$. In some cases, the ring heteroatom is a N. In some cases, A is connected at a ring carbon to $L^1$ and/or $L^2$. In some cases, A is connected at a ring heteroatom to one of $L^1$ and $L^2$ and at a ring carbon to the other of $L^1$ or $L^2$. In some cases, A is connected at the ring atom in position 1, 2, 3, 4, 5, 6, or 7 to $L^1$. In some cases, A is connected at the ring atom in position 1, 2, 3, 4, 5, 6, or 7 to $L^2$.

In a compound of Formula VII, A may be optionally substituted with one or more $R^A$ groups (e.g., by replacing a hydrogen connected to a ring atom with a bond to $R^A$). A may be optionally substituted with 0, 1, 2, 3, 4, 5, 6, 7, 8, 9, 10, 11, or 12 $R^A$ groups. A may be optionally substituted with at least 1, 2, 3, 4, 5, 6, 7, 8, 9, 10, 11, or 12 $R^A$ groups. A may be optionally substituted with up to 1, 2, 3, 4, 5, 6, 7, 8, 9, 10, 11, or 12 $R^A$ groups. In some cases, A is not substituted. In some cases, A is optionally substituted with m $R^A$ groups. In some cases, m is an integer from 0 to 12. In some cases, m is 0, 1, 2, 3, 4, 5, 6, 7, 8, 9, 10, 11, or 12. In some cases, m at least 0, 1, 2, 3, 4, 5, 6, 7, 8, 9, 10, 11, or 12. In some cases, m is up to 0, 1, 2, 3, 4, 5, 6, 7, 8, 9, 10, 11, or 12. In some cases, A is optionally substituted with p $R^A$ groups. In some cases, p is an integer from 1 to 9. In some cases, p is 1, 2, 3, 4, 5, 6, 7, 8, or 9. In some cases, p is at least 1, 2, 3, 4, 5, 6, 7, 8, or 9. In some cases, p is up to 1, 2, 3, 4, 5, 6, 7, 8, or 9. In some cases, $R^A$ is, at each occurrence, independently selected from halo, hydroxyl, amino, cyano, dialkylphosphine oxide, oxo, carboxyl, amido, acyl, alkyl, cycloalkyl, heteroalkyl, haloalkyl, aminoalkyl, hydroxyalkyl, alkoxy, alkylamino, cycloalkylalkyl, cycloalkyloxy, cycloalkylalkyloxy, cycloalkylamino, cycl oalkylalkylamino, heterocyclyl, heterocyclylalkyl, heterocyclyloxy, heterocyclylalkyloxy, heterocyclylamino, heterocyclylalkylamino, aryl, aralkyl, aryloxy, aralkyloxy, arylamino, aralkylamino, heteroaryl, heteroarylalkyl, heteroaryloxy, heteroarylalkyloxy, heteroarylamino, and heteroarylalkylamino. An $R^A$ group may be connected to any ring atom of A. In some cases, an $R^A$ group is connected to a ring carbon of A. In some cases, an $R^A$ group is connected to a ring heteroatom of A. In some cases, an $R^A$ group is connected to the ring atom in position 1, 2, 3, 4, 5, 6, or 7 of A. In some cases, two $R^A$ groups may be connected to the same ring atom of A. In some cases, only one $R^A$ group may be connected to each ring atom of A. In some cases, two $R^A$ groups attached to the same atom or different atoms can together optionally form a bridge or ring. In some cases, two $R^A$ groups attached to the same atom or different atoms can together optionally be an alkylene, alkylenecarbonyl, alkenylene, alkenylenecarbonyl, arylene, heteroalkylene, heteroalkylenecarbonyl, heteroarylene, heteroarylenecarbonyl, heterocyclylalkylene, or heterocyclylalkylenecarbonyl.

In some cases, for a compound of Formula VII, A is selected from a ring A structure listed in Table 2. In some cases, A is selected from A-1 to A-101 and any combination thereof. In some cases, A is selected from A-1 to A-18, A-40 to A-42, A-44, A-50 to A-57, A-78 to A-87, A-90, A-92, A-95 to A-101, and any combination thereof. In some cases, A is not one or more ring A structures listed in Table 2. In some cases, A is not 1, 2, 3, 4, 5, 6, or 7 ring A structures selected from the group consisting of ring A structures A-7, A-8, A-9, A-10, A-16, A-17, and A-18. In some cases, a ring A structure in Table 2 may contain one or more R$^A$ groups and may be optionally substituted with one or more additional R$^A$ groups.
TABLE 2
Non-limiting examples of Ring A structures
| Ring A Number | Ring A Structure |
|---|---|
| A-1 |  |
| A-2 |  |
| A-3 |  |
| A-4 | 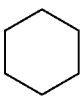 |
| A-5 | 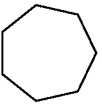 |
| A-6 |  |
| A-7 |  |
| A-8 |  |
| A-9 |  |
| A-10 | 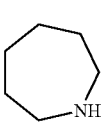 |
| A-11 | 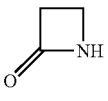 |
| A-12 | 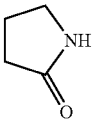 |
| A-13 | 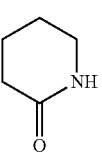 |
| A-14 | 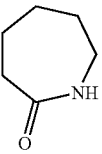 |
| A-15 |  |
| A-16 | 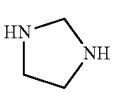 |
| A-17 | 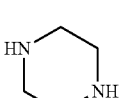 |
| A-18 | 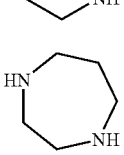 |
| A-19 | 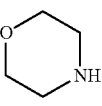 |
| A-20 | 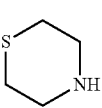 |
| A-21 | 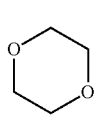 |
| A-22 | 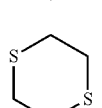 |
| A-23 | 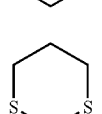 |
| A-24 | 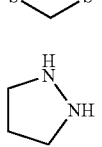 |
| A-25 |  |
| A-26 |  |
| A-27 |  |

TABLE 2-continued
Non-limiting examples of Ring A structures
| Ring A Number | Ring A Structure |
|---|---|
| A-28 |  |
| A-29 |  |
| A-30 |  |
| A-31 |  |
| A-32 |  |
| A-33 |  |
| A-34 |  |
| A-35 |  |
| A-36 |  |
| A-37 |  |
| A-38 |  |
| A-39 |  |
| A-40 |  |
| A-41 |  |
| A-42 |  |
| A-43 |  |
| A-44 |  |
| A-45 |  |
| A-46 |  |
| A-47 |  |
| A-48 |  |
| A-49 |  |
| A-50 |  |
| A-51 |  |
| A-52 |  |
| A-53 |  |
| A-54 |  |
| A-55 |  |
| A-56 | |

TABLE 2-continued
Non-limiting examples of Ring A structures
| Ring A Number | Ring A Structure |
|---|---|
| A-57 | 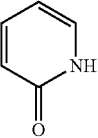 |
| A-58 |  |
| A-59 |  |
| A-60 |  |
| A-61 | 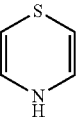 |
| A-62 |  |
| A-63 |  |
| A-64 |  |
| A-65 |  |
| A-66 |  |
| A-67 |  |
| A-68 |  |
| A-69 |  |
| A-70 |  |
| A-71 | 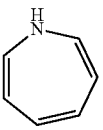 |
| A-72 |  |
| A-73 |  |
| A-74 | 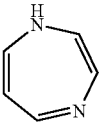 |
| A-75 | 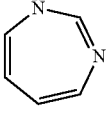 |
| A-76 | 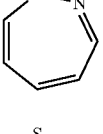 |
| A-77 | 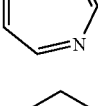 |
| A-78 | 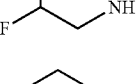 |
| A-79 | 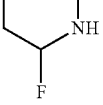 |

TABLE 2-continued

Non-limiting examples of Ring A structures

| Ring A Number | Ring A Structure |
|---|---|
| A-80 | 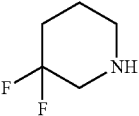 |
| A-81 | 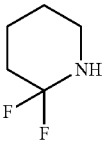 |
| A-82 |  |
| A-83 |  |
| A-84 |  |
| A-85 |  |
| A-86 |  |
| A-87 |  |
| A-88 |  |
| A-89 |  |
| A-90 |  |
| A-91 |  |
| A-92 |  |
| A-93 |  |
| A-94 |  |
| A-95 | 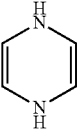 |
| A-96 | 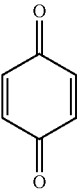 |
| A-97 |  |
| A-98 |  |
| A-99 |  |
| A-100 |  |
| A-101 |  |

$L^1$ and $L^2$

In some cases, for a compound of Formula VII, each of $L^1$ and $L^2$ is independently a bond, carbonyl, O, S, —$NR^5$—, —$NR^6CH_2$—, —$NR^6C(=O)$—, —$NR^6SO_2$—, alkylene, alkenylene, heteroalkylene, alkylenecarbonyl, alkenylenecarbonyl, or heteroalkylenecarbonyl. In some cases, an alkylene is a $C_1$, $C_2$, $C_3$, $C_4$, $C_5$, $C_6$, $C_7$, $C_8$, $C_9$, $C_{10}$, $C_{11}$, or $C_{12}$ alkylene. In some cases, an alkylene is up to a $C_1$, $C_2$, $C_3$, $C_4$, $C_5$, $C_6$, $C_7$, $C_8$, $C_9$, $C_{10}$, $C_{11}$, or $C_{12}$ alkylene. In some cases, an alkylene is at least a $C_1$, $C_2$, $C_3$, $C_4$, $C_5$, $C_6$, $C_7$, $C_8$, $C_9$, $C_{10}$, $C_{11}$, or $C_{12}$ alkylene. In some cases, an alkylene contains 1, 2, 3, 4, 5, 6, 7, 8, 9, 10, 11, or 12 chain carbons. In some cases, an alkylene contains up to 1, 2, 3, 4, 5, 6, 7, 8, 9, 10, 11, or 12 chain carbons. In some cases, an alkylene contains at least 1, 2, 3, 4, 5, 6, 7, 8, 9, 10, 11, or 12 chain carbons. In some cases, an alkylene contains 0, 1, 2, 3, 4, 5, 6, or 7 double and/or triple bonds. In some cases, an alkylene contains up to 1, 2, 3, 4, 5, 6, or 7 double and/or triple bonds. In some cases, an alkylene contains at least 1, 2, 3, 4, 5, 6, or 7 double and/or triple bonds. In some cases, an alkylene chain is attached to the rest of the molecule through a single or double bond and to the radical group through a single or double bond. In some cases, an alkylene chain is attached to the rest of the molecule through a single bond and to the radical group through a single bond. In some cases, the points of attachment of the alkylene chain to the rest of the molecule and to the radical group are through one carbon or any two carbons within the chain. In some cases, the points of attachment of the alkylene chain to the rest of the molecule and to the radical group can be through one carbon within the chain. In some cases, the points of attachment of the alkylene chain to the rest of the molecule and to the radical group can be through any two carbons within the chain. In some cases, an alkenylene contains 1, 2, 3, 4, 5, 6, or 7 double bonds. In some cases, an alkenylene contains up to 1, 2, 3, 4, 5, 6, or 7 double bonds. In some cases, an alkenylene contains at least 1, 2, 3, 4, 5, 6, or 7 double bonds. In some cases, a heteroalkylene contains 1, 2, 3, 4, 5, 6, 7, 8, 9, or 10 chain heteroatoms. In some cases, a heteroalkylene contains up to 1, 2, 3, 4, 5, 6, 7, 8, 9, or 10 chain heteroatoms. In some cases, a heteroalkylene contains at least 1, 2, 3, 4, 5, 6, 7, 8, 9, or 10 chain heteroatoms. In some cases, the heteroatom or heteroatoms are within the alkylene chain. In some cases, the heteroatom or heteroatoms are one or two termini of the alkylene and join the alkylene to the remainder of the molecule and/or to the radical group.

In some cases, for a compound of Formula VII, $L^1$ and $L^2$, when present, are each independently selected from bond, —O—, —S—, —N($R^{51}$)—, —N($R^{51}$)CH$_2$—, —C(O)—, —C(O)O—, —OC(O)—, —OC(O)O—, —C(O)N($R^{51}$)—, —C(O)N($R^{51}$)C(O)—, —C(O)N($R^{51}$)C(O)N($R^{51}$)—, —N($R^{51}$)C(O)—, —N($R^{51}$)C(O)N($R^{51}$)—, —N($R^{51}$)C(O)O—, —OC(O)N($R^{51}$)—, —C(N$R^{51}$)—, —N($R^{51}$)C(N$R^{51}$)—, —C(N$R^{51}$)N($R^{51}$)—, —N($R^{51}$)C(N$R^{51}$)N($R^{51}$)—, —S(O)$_2$—, —OS(O)—, —S(O)O—, —S(O)—, —OS(O)$_2$—, —S(O)$_2$O—, —N($R^{51}$)S(O)$_2$—, —S(O)$_2$N($R^{51}$)—, —N($R^{51}$)S(O)—, —S(O)N($R^{51}$)—, —N($R^{51}$)S(O)$_2$N($R^{51}$)—, —N($R^{51}$)S(O)N($R^{51}$)—; alkylene, alkenylene, alkynylene, heteroalkylene, heteroalkenylene, and heteroalkynylene, each of which is optionally substituted with one or more $R^{50}$, wherein two $R^{50}$ groups attached to the same atom or different atoms of any one of $L^1$ and $L^2$ can together optionally form a bridge or ring;

$R^{50}$ is independently selected at each occurrence from:
halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$);

$C_{1-10}$ alkyl, $C_{2-10}$ alkenyl, and $C_{2-10}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in $R^{50}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), $C_{1-6}$ alkyl, $C_{1-6}$ haloalkyl, $C_{2-6}$ alkenyl, and $C_{2-6}$ alkynyl;

$R^{51}$ is independently selected at each occurrence from: hydrogen, —C(O)R$^{52}$, —C(O)OR$^{52}$, and —C(O)N(R$^{52}$)$_2$, —C(O)NR$^{53}$R$^{54}$;

$C_{1-6}$ alkyl, $C_{2-6}$ alkenyl, and $C_{2-6}$ alkynyl, each of which is independently optionally substituted at each occurrence with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), $C_{3-12}$ carbocycle and 3- to 12-membered heterocycle; and $C_{3-12}$ carbocycle and 3- to 12-membered heterocycle, wherein each $C_{3-12}$ carbocycle and 3- to 12-membered heterocycle in $R^{51}$ is independently optionally substituted with one or more substituents selected from halogen, —NO$_2$, —CN, —OR$^{52}$, —SR$^{52}$, —N(R$^{52}$)$_2$, —NR$^{53}$R$^{54}$, —S(=O)R$^{52}$, —S(=O)$_2$R$^{52}$, —S(=O)$_2$N(R$^{52}$)$_2$, —S(=O)$_2$NR$^{53}$R$^{54}$, —NR$^{52}$S(=O)$_2$R$^{52}$, —NR$^{52}$S(=O)$_2$N(R$^{52}$)$_2$, —NR$^{52}$S(=O)$_2$NR$^{53}$R$^{54}$, —C(O)R$^{52}$, —C(O)OR$^{52}$, —OC(O)R$^{52}$, —OC(O)OR$^{52}$, —OC(O)N(R$^{52}$)$_2$, —OC(O)NR$^{53}$R$^{54}$, —NR$^{52}$C(O)R$^{52}$, —NR$^{52}$C(O)OR$^{52}$, —NR$^{52}$C(O)N(R$^{52}$)$_2$, —NR$^{52}$C(O)NR$^{53}$R$^{54}$, —C(O)N(R$^{52}$)$_2$, —C(O)NR$^{53}$R$^{54}$, —P(O)(OR$^{52}$)$_2$, —P(O)(R$^{52}$)$_2$, =O, =S, =N(R$^{52}$), $C_{1-6}$ alkyl, $C_{1-6}$ haloalkyl, $C_{2-6}$ alkenyl, and $C_{2-6}$ alkynyl;

$R^{52}$ is independently selected at each occurrence from hydrogen; and $C_{1-20}$ alkyl, $C_{2-20}$ alkenyl, $C_{2-20}$ alkynyl, 1- to 6-membered heteroalkyl, $C_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, $C_{3-12}$ carbocycle, and 3- to 6-membered heterocycle; and $R^{53}$ and $R^{54}$ are taken together with the nitrogen atom to which they are attached to form a heterocycle, optionally substituted with one or more $R^{50}$.

Ring B

In some cases, for a compound of Formula VII, B is monocyclic or bicyclic (e.g., two fused rings). In some cases, B is a bicyclic ring system comprising a 6-membered ring. In some cases, B is a bicyclic ring system comprising a 6-membered ring fused to a 5-membered ring. In some cases, B is a bicyclic ring system comprising a 6-membered ring fused to a 6-membered ring. In some cases, one or two rings of B are aromatic, non-aromatic, saturated, or unsaturated. In some cases, one or two rings of B are an aryl, arylene, cycloalkyl, heterocyclyl, N-heterocyclyl, heteroaryl, heteroarylene, or N-heteroaryl. In some cases, B is selected from B-I, B-II, B-III, B-IV, and any combination thereof, where B-I is

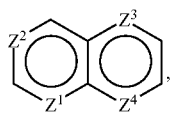

B-II is

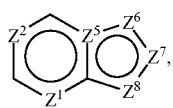

B-III is

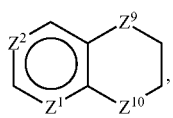

and B-IV is

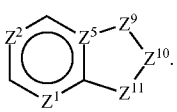

In some cases, each of $Z^1$, $Z^2$, $Z^3$, and $Z^4$ is independently $CR^7$, N, or $NR^9$. In some cases, $Z^5$ is C or N. In some cases, each of $Z^6$, $Z^7$, and $Z^8$ is independently $CR^8$, N, $NR^9$, O, or S. In some cases, each of $Z^9$, $Z^{10}$, and $Z^{11}$ is independently $CR^{10}$, $CR^{11}R^{12}$, $NR^{13}$, O, or S.

In a compound of Formula VII, B or any one of B-I, B-II, B-III, or B-IV may contain one or more heteroatoms. In some cases, B or any one of B-I, B-II, B-III, or B-IV contains 0, 1, 2, 3, 4, or 5 ring heteroatoms. In some cases, B or any one of B-I, B-II, B-III, or B-IV contains at least 1, 2, 3, 4, or 5 ring heteroatoms. In some cases, B or any one of B-I, B-II, B-III, or B-IV contains up to 1, 2, 3, 4, or 5 ring heteroatoms. In some cases, B or any one of B-I, B-II, B-III, or B-IV contains 0, 1, 2, 3, or 4 ring N atoms. In some cases, B or any one of B-I, B-II, B-III, or B-IV contains at least 1, 2, 3, or 4 ring N atoms. In some cases, B or any one of B-I, B-II, B-III, or B-IV contains up to 1, 2, 3, or 4 ring N atoms. In some cases, B or any one of B-I, B-II, B-III, or B-IV contains 0, 1, or 2 ring O atoms. In some cases, B or any one of B-I, B-II, B-III, or B-IV contains at least 1 or 2 ring O atoms. In some cases, B or any one of B-I, B-II, B-III, or B-IV contains up to 1 or 2 ring O atoms. In some cases, B or any one of B-I, B-II, B-III, or B-IV contains 0, 1, or 2 ring S atoms. In some cases, B or any one of B-I, B-II, B-III, or B-IV contains at least 1 or 2 ring S atoms. In some cases, B or any one of B-I, B-II, B-III, or B-IV contains up to 1 or 2 ring S atoms. In some cases, B or any one of B-I, B-II, B-III, or B-IV contains 3, 4, 5, 6, 7, 8, 9, or 10 ring carbon atoms. In some cases, B or any one of B-I, B-II, B-III, or B-IV contains at least 3, 4, 5, 6, 7, 8, 9, or 10 ring carbon atoms. In some cases, B or any one of B-I, B-II, B-III, or B-IV contains up to 3, 4, 5, 6, 7, 8, 9, or 10 ring carbon atoms.

In a compound of Formula VII, B or any one of B-I, B-II, B-III, or B-IV may be connected at any ring atom to $L^2$ (e.g., by replacing a hydrogen connected to a ring atom with a bond to $L^2$). In some cases, B or any one of B-I, B-II, B-III, or B-IV is connected at a ring heteroatom to $L^2$. In some cases, the ring heteroatom is a N. In some cases, B or any one of B-I, B-II, B-III, or B-IV is connected at a ring carbon to $L^2$. In some cases, B or any one of B-I, B-II, B-III, or B-IV is connected at a ring atom of an aromatic ring to $L^2$. In some cases, B or any one of B-I, B-II, B-III, or B-IV is connected at a ring atom of a non-aromatic ring to $L^2$. In some cases, B or any one of B-I, B-II, B-III, or B-IV is connected at a ring atom of a 6-membered ring to $L^2$. In some cases, B or any one of B-I, B-II, B-III, or B-IV is connected at a ring atom of a 5-membered ring to $L^2$. In some cases, B or any one of B-I, B-II, B-III, or B—IV is connected at a ring atom of a benzene ring. In some cases, B or any one of B-I, B-II, B-III, or B-IV is connected at a ring atom of a non-benzene ring. In some cases, B or any one of B-I, B-II, B-III, or B-IV is connected at the ring atom in position 1, 2, 3, 4, 5, 6, 7, or 8 to $L^2$.

In some cases, for a compound of Formula VII, B-I or any one of B-I-2 to B-I-20 is connected to $L^2$ at a position selected from

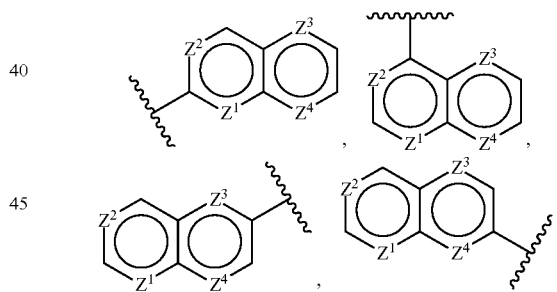

and any combination thereof. In some cases, B-I or any one of B-I-2 to B-I-24 is connected to $L^2$ at a position selected from

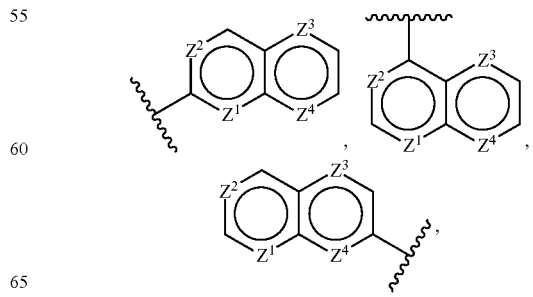

and any combination thereof. In some cases, B-II or any one of B-II-2 to B-II-52 is connected to $L^2$ at a position selected from

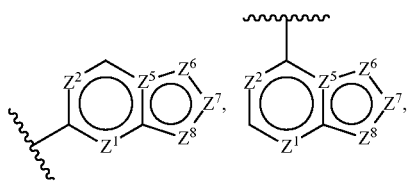

and any combination thereof. In some cases, B-III or any one of B-III-2 to B-III-12 is connected to $L^2$ at a position selected from

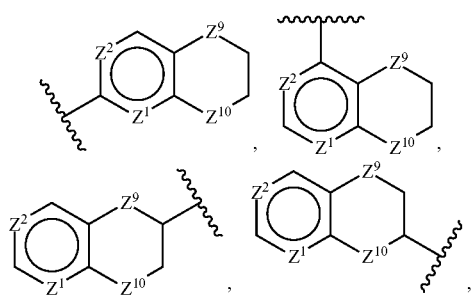

and any combination thereof. In some cases, B-III or any one of B-III-2 to B-III-13 is connected to $L^2$ at a position selected from

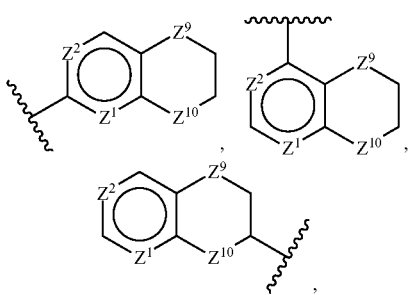

and any combination thereof. In some cases, B-IV or any one of B-IV-2 to B-IV-27 is connected to $L^2$ at a position selected from

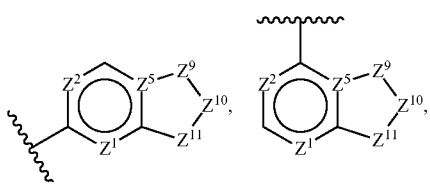

and any combination thereof.

In a compound of Formula VII, B may be optionally substituted with one or more $R^B$ groups (e.g., by replacing a hydrogen connected to a ring atom with a bond to $R^B$). B may be optionally substituted with 0, 1, 2, 3, 4, 5, or 6 $R^B$ groups. B may be optionally substituted with at least 1, 2, 3, 4, 5, or 6 $R^B$ groups. B may be optionally substituted with up to 1, 2, 3, 4, 5, or 6 $R^B$ groups. In some cases, B is not substituted. In some cases, B is optionally substituted with n $R^B$ groups. In some cases, n is an integer from 0 to 6. In some cases, n is 0, 1, 2, 3, 4, 5, or 6. In some cases, n is at least 0, 1, 2, 3, 4, 5, or 6. In some cases, n is up to 0, 1, 2, 3, 4, 5, or 6. In some cases, $R^B$ is, at each occurrence, independently selected from halo, hydroxyl, amino, cyano, dialkylphosphine oxide, oxo, carboxyl, amido, acyl, alkyl, cycloalkyl, heteroalkyl, haloalkyl, aminoalkyl, hydroxyalkyl, alkoxy, alkylamino, cycloalkylalkyl, cycloalkyloxy, cycloalkylalkyloxy, cycloalkylamino, cycl oalkylalkylamino, heterocyclyl, heterocyclylalkyl, heterocyclyloxy, heterocyclylalkyloxy, heterocyclylamino, heterocyclylalkylamino, aryl, aralkyl, aryloxy, aralkyloxy, arylamino, aralkylamino, heteroaryl, heteroarylalkyl, heteroaryloxy, heteroarylalkyloxy, heteroarylamino, and heteroarylalkylamino. An $R^B$ group may be connected to any ring atom of B. In some cases, an $R^B$ group is connected to a ring carbon of B. In some cases, an $R^B$ group is connected to a ring heteroatom of B. In some cases, an $R^B$ group is connected to the ring atom in position 1, 2, 3, 4, 5, 6, 7, or 8 of B. In some cases, two $R^B$ groups may be connected to the same ring atom of B. In some cases, only one $R^B$ group may be connected to each ring atom of B. In some cases, two $R^B$ groups attached to the same atom or different atoms can together optionally form a bridge or ring. In some cases, two $R^B$ groups attached to the same atom or different atoms can together optionally be an alkylene, alkylenecarbonyl, alkenylene, alkenylenecarbonyl, arylene, heteroalkylene, heteroalkylenecarbonyl, heteroarylene, heteroarylenecarbonyl, heterocyclylalkylene, or heterocyclylalkylenecarbonyl.

In some cases, for a compound of Formula VII, B is selected from a ring B structure listed in Table 3. In some cases, B is selected from B-I, B-I-2 to B-I-24, B-II, B-II-2 to B-II-52, B-III, B-III-2 to B-III-13, B-IV, B-IV-2 to B-IV-27, and any combination thereof. In some cases, B is not one or more ring B structures listed in Table 3. In some cases, B is not 1, 2, 3, 4, 5, 6, 7, or 8 ring B structures selected from B-II-20, B-II-27, B-II-28, B-II-29, B-II-30, B-II-38, B-II-52, B-III-13. In some cases, a ring B structure in Table 3 may contain one or more $R^B$ groups and may be optionally substituted with one or more additional $R^B$ groups.

TABLE 3

Non-limiting examples of Ring B structures

| Ring B Number | Ring B Structure |
|---|---|
| B-I | |
| B-I-2 | |
| B-I-3 | |

TABLE 3-continued

Non-limiting examples of Ring B structures

| Ring B Number | Ring B Structure |
|---|---|
| B-I-4 | |
| B-I-5 | |
| B-I-6 | |
| B-I-7 | |
| B-I-8 | |
| B-I-9 | |
| B-I-10 | |
| B-I-11 | |
| B-I-12 | |
| B-I-13 | |
| B-I-14 | |
| B-I-15 | |
| B-I-16 | |
| B-I-17 | |
| B-I-18 | |
| B-I-19 | |
| B-I-20 | |
| B-I-21 | |
| B-I-22 | |
| B-I-23 | |
| B-I-24 | |
| B-II | |
| B-II-2 | |

TABLE 3-continued

Non-limiting examples of Ring B structures

| Ring B Number | Ring B Structure |
|---|---|
| B-II-3 | |
| B-II-4 | |
| B-II-5 | |
| B-II-6 | |
| B-II-7 | |
| B-II-8 | |
| B-II-9 | |
| B-II-10 | |
| B-II-11 | |
| B-II-12 | |
| B-II-13 | |
| B-II-14 | |
| B-II-15 | |
| B-II-16 | |
| B-II-17 | |
| B-II-18 | |
| B-II-19 | |
| B-II-20 | |
| B-II-21 | |
| B-II-22 | |
| B-II-23 | |
| B-II-24 | |
| B-II-25 | |
| B-II-26 | |

TABLE 3-continued
Non-limiting examples of Ring B structures
| Ring B Number | Ring B Structure |
|---|---|
| B-II-27 | 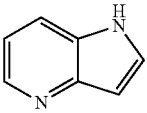 |
| B-II-28 | 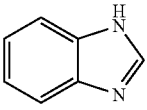 |
| B-II-29 | 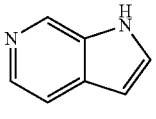 |
| B-II-30 | 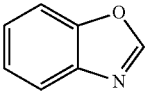 |
| B-II-31 | 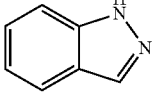 |
| B-II-32 | 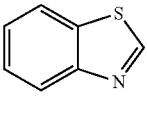 |
| B-II-33 | 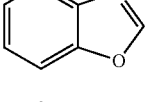 |
| B-II-34 | 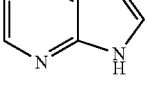 |
| B-II-35 | 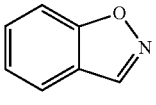 |
| B-II-36 | 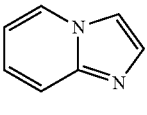 |
| B-II-37 | 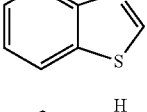 |
| B-II-38 | 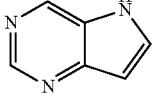 |
| B-II-39 | 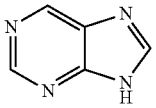 |
| B-II-40 | 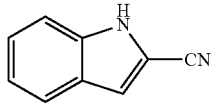 |
| B-II-41 | 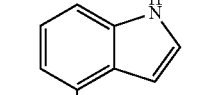 |
| B-II-42 | 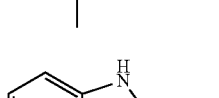 |
| B-II-43 | 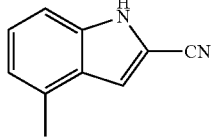 |
| B-II-44 | 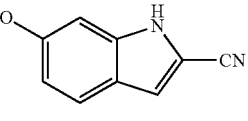 |
| B-II-45 | 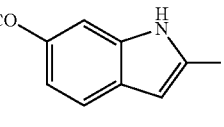 |
| B-II-46 | 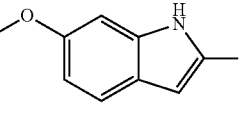 |
| B-II-47 | 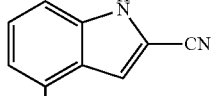 |
| B-II-48 | 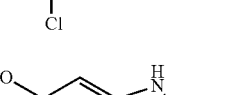 |
| B-II-49 | 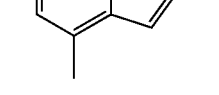 |

TABLE 3-continued

Non-limiting examples of Ring B structures

| Ring B Number | Ring B Structure |
|---|---|
| B-II-50 | |
| B-II-51 | |
| B-II-52 | |
| B-III | |
| B-III-2 | |
| B-III-3 | |
| B-III-4 | |
| B-III-5 | |
| B-III-6 | |
| B-III-7 | |
| B-III-8 | |
| B-III-9 | |
| B-III-10 | |
| B-III-11 | |
| B-III-12 | |
| B-III-13 | |
| B-IV | |
| B-IV-2 | |
| B-IV-3 | |
| B-IV-4 | |
| B-IV-5 | |
| B-IV-6 | |

TABLE 3-continued

Non-limiting examples of Ring B structures

| Ring B Number | Ring B Structure |
|---|---|
| B-IV-7 | (structure with $R^7$, $Z^5$, $Z^9$, $Z^{10}$, $Z^1$, $Z^{11}$) |
| B-IV-8 | (structure with $Z^2$, N, $Z^9$, $Z^{10}$, $Z^{11}$, N) |
| B-IV-9 | (structure with N, N, $Z^9$, $Z^{10}$, $Z^1$, $Z^{11}$) |
| B-IV-10 | (structure with N, $Z^5$, $Z^9$, $Z^{10}$, N, $Z^{11}$) |
| B-IV-11 | (structure with $Z^2$, $Z^9$, $Z^{10}$, $Z^{11}$, $R^7$) |
| B-IV-12 | (structure with $R^7$, $Z^9$, $Z^{10}$, $Z^1$, $Z^{11}$) |
| B-IV-13 | (structure with $R^7$, $Z^5$, $Z^9$, $Z^{10}$, $Z^{11}$, $R^7$) |
| B-IV-14 | (structure with $R^7$, N, $Z^9$, $Z^{10}$, $Z^1$, $Z^{11}$) |
| B-IV-15 | (structure with $Z^2$, N, $Z^9$, $Z^{10}$, $Z^{11}$, $R^7$) |
| B-IV-16 | (structure with N, $Z^9$, $Z^{10}$, $Z^1$, $Z^{11}$) |
| B-IV-17 | (structure with $Z^2$, $Z^9$, $Z^{10}$, $Z^{11}$, N) |
| B-IV-18 | (structure with N, $Z^5$, $Z^9$, $Z^{10}$, $Z^{11}$, $R^7$) |
| B-IV-19 | (structure with $R^7$, $Z^5$, $Z^9$, $Z^{10}$, N, $Z^{11}$) |
| B-IV-20 | (indoline structure) |
| B-IV-21 | (benzimidazoline structure) |
| B-IV-22 | (2,3-dihydrobenzofuran structure) |
| B-IV-23 | (1,3-benzodioxole structure) |
| B-IV-24 | (oxindole structure) |
| B-IV-25 | (4-methyl oxindole structure) |
| B-IV-26 | (3,3-dimethyl oxindole structure) |
| B-IV-27 | (3,3,4-trimethyl oxindole structure) |

In certain embodiments, the compound of Formula VII has an H-VII selected from one of H-VII-2 to H-VII-28 in Table Id. In particular, H-VII may be selected from H-VII-2 and H-VII-4. In certain embodiments, H-VII of a compound of Formula VII is represented by the formula H-VII-2:

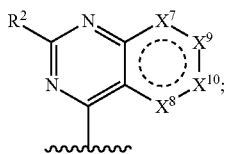

(H-VII-2)

wherein $R^2$ is selected from H, halo, hydroxyl, amino, cyano, dialkylphosphine oxide, oxo, carboxyl, amido, acyl, alkyl, cycloalkyl, heteroalkyl, haloalkyl, aminoalkyl, hydroxyalkyl, alkoxy, and alkylamino, such as from H, halo, hydroxyl, and amino; and each of $X^7$, $X^8$, $X^9$, and $X^{10}$ is independently selected from $CR^{16}$, $CR^{17}R^{18}$, N, $NR^{19}$, O, and S. In certain embodiments, 0, 1, or 2 of $X^7$, $X^8$, $X^9$, and $X^{10}$ are independently selected from N, $NR^{19}$, O, and S. In certain embodiments, when both rings of H-VII-2 are aromatic, each of $X^7$, $X^8$, $X^9$, and $X^{10}$ is independently selected from $CR^{16}$, $CR^{17}R^{18}$, N, and $NR^{19}$.

In certain embodiments, H-VII of a compound of Formula VII is represented by the formula H-VII-4:

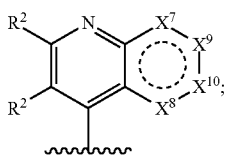

(H-VII-4)

wherein $R^2$, at each occurrence, is selected from H, halo, hydroxyl, amino, cyano, dialkylphosphine oxide, oxo, carboxyl, amido, acyl, alkyl, cycloalkyl, heteroalkyl, haloalkyl, aminoalkyl, hydroxyalkyl, alkoxy, and alkylamino, such as from H, halo, hydroxyl, and amino; and each of $X^7$, $X^8$, $X^9$, and $X^{10}$ is independently selected from $CR^{16}$, $CR^{17}R^{18}$, N, $NR^{19}$, O, and S. In certain embodiments, 0, 1, or 2 of $X^7$, $X^8$, $X^9$, and $X^{10}$ are independently selected from N, $NR^{19}$, O, and S. In certain embodiments, when both rings of H-VII-2 are aromatic, each of $X^7$, $X^8$, $X^9$, and $X^{10}$ is independently selected from $CR^{16}$, $CR^{17}R^{18}$, N, and $NR^{19}$.

In some cases, when H-VII of Formula VII is selected from one of H-VII-2 to H-VII-28, such as from H-VII-2 and H-VII-4, $R^2$ of a compound of Formula VII may be, at each occurrence, selected from H, halo, hydroxyl, amino, cyano, dialkylphosphine oxide, oxo, carboxyl, amido, acyl, alkyl, cycloalkyl, heteroalkyl, haloalkyl, aminoalkyl, hydroxyalkyl, alkoxy, and alkylamino, such as from H, halo, hydroxyl, and amino. In some cases, when H-VII of Formula VII is selected from one of H-VII-2 to H-VII-28, such as from H-VII-2 and H-VII-4, $R^{16}$, $R^{17}$, $R^{18}$, and $R^{19}$ of a compound of Formula VII may be, at each occurrence, selected from H, halo, hydroxyl, amino, cyano, dialkylphosphine oxide, oxo, carboxyl, amido, acyl, alkyl, cycloalkyl, heteroalkyl, haloalkyl, aminoalkyl, hydroxyalkyl, alkoxy, and alkylamino, such as from H, halo, hydroxyl, amino, alkyl, heteroalkyl, and haloalkyl.

In some cases, when H-VII of Formula VII is selected from one of H-VII-2 to H-VII-28, such as from H-VII-2 and H-VII-4, $L^1$ may be selected from a bond, carbonyl, O, S, $-NR^5-$, $-NR^6CH_2-$, $-NR^6C(=O)-$, $-NR^6SO_2-$, $C_1$-$C_4$ alkylene, $C_2$-$C_4$ alkenylene, $C_1$-$C_4$ heteroalkylene, $C_1$-$C_4$ alkylenecarbonyl, $C_2$-$C_4$ alkenylenecarbonyl, and $C_1$-$C_4$ heteroalkylenecarbonyl. In particular, $L^1$ may be selected from a carbonyl, O, $-NR^5-$, $-NR^6CH_2-$, $-NR^6C(=O)-$, $-NR^6SO_2-$, $C_1$-$C_4$ alkylene, $C_2$-$C_4$ alkenylene, and $C_1$-$C_4$ heteroalkylene, such as $-NR^5-$ wherein $R^5$ is selected from hydrogen and alkyl.

In some cases, when H-VII of Formula VII is selected from one of H-VII-2 to H-VII-28, such as from H-VII-2 and H-VII-4, Ring A may be selected from a 3-6 membered ring, such as from a 5-6 membered ring, such as from a 5-membered cycloalkyl, 6-membered cycloalkyl, 5-membered heterocyclic ring, 6-membered heterocyclic ring, 6-membered aryl, 5-membered heteroaryl, and 6-membered heteroaryl. In certain embodiments, A is a saturated 5- or 6-membered cycloalkyl or heterocyclic ring. In certain embodiments, A is selected from A-1 to A-101. In certain embodiments, A is selected from A-1 to A-18, A-40 to A-42, A-44, A-50 to A-57, A-78 to A-87, A-90, A-92, and A-95 to A-101. In certain embodiments, A is selected from A-1 to A-18, A-41, A-44, A-57, and A-78 to A-87. In certain embodiments, A is selected from A-1 to A-4, A-6 to A-9, A-11 to A-13, A-15 to A-17, A-41, A-44, A-57, and A-78 to A-87. In certain embodiments, A contains 0, 1, or 2 ring N atoms. In certain embodiments, A contains 0, 1, or 2 ring N atoms and no other ring heteroatoms. In certain embodiments, A is connected at the same ring atom to $L^1$ and $L^2$. In certain embodiments, A is connected at different ring atoms to $L^1$ and $L^2$. In certain embodiments, A is connected at a ring heteroatom to $L^1$ and/or $L^2$. In certain embodiments, A is connected at a ring carbon to $L^1$ and/or $L^2$. In certain embodiments, $R^A$, at each occurrence, may be selected from halo, hydroxyl, amino, cyano, dialkylphosphine oxide, oxo, carboxyl, amido, acyl, alkyl, cycloalkyl, heteroalkyl, haloalkyl, aminoalkyl, hydroxyalkyl, alkoxy, alkylamino, heterocyclylalkyl, and heteroarylalkyl. In certain embodiments, two $R^A$ groups attached to the same atom or different atoms may optionally form a bridge or ring. In certain embodiments, m is 0 to 3.

In some cases, when H-VII of Formula VII is selected from one of H-VII-2 to H-VII-28, such as from H-VII-2 and H-VII-4, $L^2$ may be selected from a bond, carbonyl, O, S, $-NR^5-$, $-NR^6CH_2-$, $-NR^6C(=O)-$, $-NR^6SO_2-$, $C_1$-$C_4$ alkylene, $C_2$-$C_4$ alkenylene, $C_1$-$C_4$ heteroalkylene, $C_1$-$C_4$ alkylenecarbonyl, $C_2$-$C_4$ alkenylenecarbonyl, and $C_1$-$C_4$ heteroalkylenecarbonyl, such as $C_1$-$C_4$ alkylene. In particular, $L^2$ may be selected from a carbonyl, O, $-NR^5-$, $-NR^6CH_2-$, $-NR^6C(=O)-$, $-NR^6SO_2-$, $C_1$-$C_4$ alkylene, and $C_1$-$C_4$ heteroalkylene.

In some cases, when H-VII of Formula VII is selected from one of H-VII-2 to H-VII-28, such as from H-VII-2 and H-VII-4, Ring B may be selected from B-I, B-I-2 to B-I-24, B-II, B-II-2 to B-II-52, B-III, B-III-2 to B-III-13, B-IV, and B-IV-2 to B-IV-27, such as from indole, benzimidazole, benzoxazole, and imidazopyridine. In certain embodiments, B contains 0, 1, 2, 3, or 4 ring heteroatoms, such as ring O and N atoms. In certain embodiments, B contains 0, 1, 2, 3, or 4 ring N atoms. In certain embodiments, B contains 0, 1, 2, 3, or 4 ring N atoms and no other ring heteroatoms. In certain embodiments, B is connected at a ring heteroatom to $L^2$, such as a ring N atom. In certain embodiments, B is connected at a ring carbon to $L^2$, such as a ring carbon on an aromatic ring. In certain embodiments, $R^B$, at each occurrence, may be selected from halo, hydroxyl, amino, cyano, dialkylphosphine oxide, oxo, carboxyl, amido, acyl, alkyl, cycloalkyl, heteroalkyl, haloalkyl, aminoalkyl, hydroxyalkyl, alkoxy, alkylamino, heterocyclylalkyl, and heteroarylalkyl. In certain embodiments, two $R^B$ groups attached to the same atom or different atoms may optionally form a bridge or ring. In certain embodiments, n is 0 to 4. In certain embodiments, n is 0 to 2.

In some cases, when H-VII of Formula VII is selected from one of H-VII-2 to H-VII-28, such as from H-VII-2 and H-VII-4, each of $R^2$, $R^7$, $R^8$, $R^{10}$, $R^{11}$, $R^{12}$, $R^{16}$, $R^{17}$, and $R^{18}$ is, at each occurrence, independently selected from H, halo, hydroxyl, amino, cyano, dialkylphosphine oxide, oxo, carboxyl, amido, acyl, alkyl, heteroalkyl, haloalkyl, aminoalkyl, hydroxyalkyl, alkoxy, alkylamino, cycloalkylalkyl, cycloalkyloxy, cycloalkylalkyloxy, cycloalkylamino, cycloalkylalkylamino, heterocyclylalkyl, heterocyclyloxy, heterocyclylalkyloxy, heterocyclylamino, heterocyclylalkylamino, aralkyl, aryloxy, aralkyloxy, arylamino, aralkylamino, heteroarylalkyl, heteroaryloxy, heteroarylalkyloxy, heteroarylamino, and heteroarylalkylamino, such as from H, halo, hydroxyl, amino, cyano, dialkylphosphine oxide, oxo, carboxyl, amido, acyl, alkyl, heteroalkyl, haloalkyl, aminoalkyl, hydroxyalkyl, alkoxy, alkylamino, cycloalkylalkyl, cycloalkylalkyloxy, cycloalkylalkylamino, heterocyclylalkyl, heterocyclylalkyloxy, heterocyclylalkylamino, aralkyl, aralkyloxy, aralkylamino, heteroarylalkyl, heteroarylalkyloxy, and heteroarylalkylamino.

In some cases, when H-VII of Formula VII is selected from one of H-VII-2 to H-VII-28, such as from H-VII-2 and H-VII-4, each of $R^5$, $R^6$, $R^9$, $R^{13}$, and $R^{19}$ is, at each occurrence, independently selected from H, acyl, alkyl, cycloalkyl, heteroalkyl, haloalkyl, aminoalkyl, hydroxyalkyl, cycloalkylalkyl, heterocyclyl, heterocyclylalkyl, aryl, aralkyl, heteroaryl, and heteroarylalkyl, such as from H, acyl, alkyl, heteroalkyl, haloalkyl, aminoalkyl, hydroxyalkyl, cycloalkylalkyl, heterocyclylalkyl, aralkyl, and heteroarylalkyl.

In particular embodiments, H-VII of Formula VII is selected from H-VII-2 and H-VII-4; $R^2$ is selected from H, halo, hydroxyl, or amino; $L^1$ is selected from O, —$NR^5$—, —$NR^6CH_2$—, —$NR^6C(=O)$—, and —$NR^6SO_2$—, such as from O and —$NR^5$—; A is selected from a 5- or 6-membered ring, such as from a cycloalkyl and heterocyclic ring; $L^2$ is selected from —$NR^5$—, —$NR^6CH_2$—, —$NR^6C(=O)$—, —$NR^6SO_2$—, $C_1$-$C_4$ alkylene, $C_2$-$C_4$ alkenylene, and $C_1$-$C_4$ heteroalkylene; and B is selected from B-I, B-I-2 to B-I-24, B-II, B-II-2 to B-II-52, B-III, B-III-2 to B-III-13, B-IV, and B-IV-2 to B-IV-27, such as from indole, benzimidazole, benzoxazole, and imidazopyridine.

In certain embodiments, a compound of Formula VII has the structure of Formula VII-A:

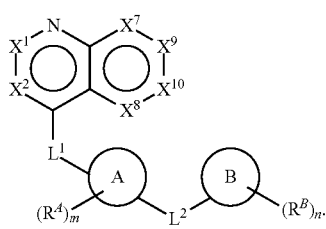

(VII-A)

In certain embodiments, a compound of Formula VII has the structure of Formula VII-B:

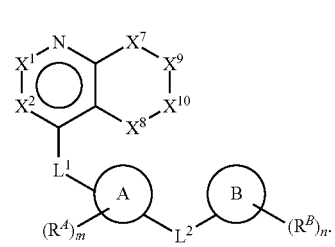

(VII-B)

In certain embodiments, a compound of Formula VII has the structure of Formula VII-C:

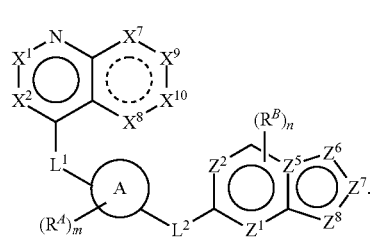

(VII-C)

In certain embodiments, a compound of Formula VII has the structure of Formula VII-D:

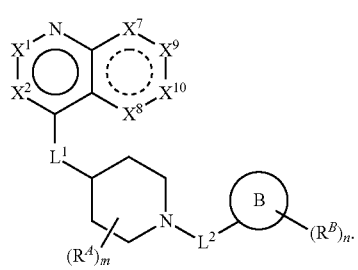

(VII-D)

In certain embodiments, a compound of Formula VII has the structure of Formula VII-E:

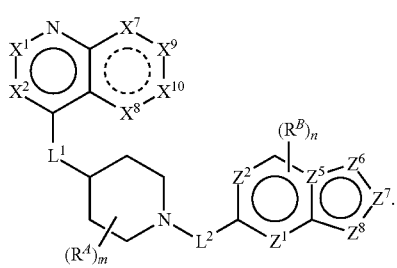

(VII-E)

In certain embodiments, a compound of Formula VII has the structure of Formula VII-F:

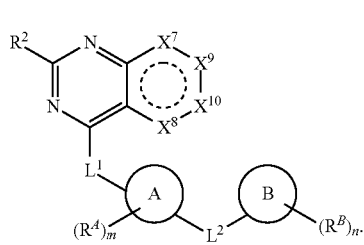

(VII-F)

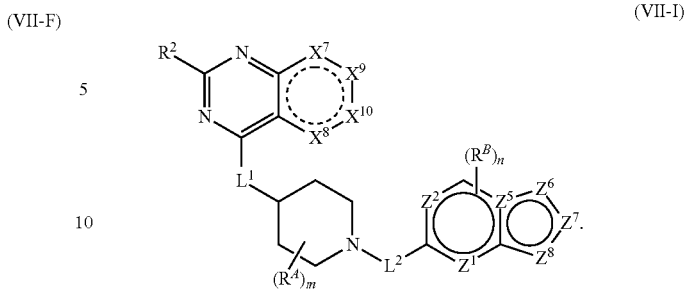

(VII-I)

In certain embodiments, a compound of Formula VII has the structure of Formula VII-G:

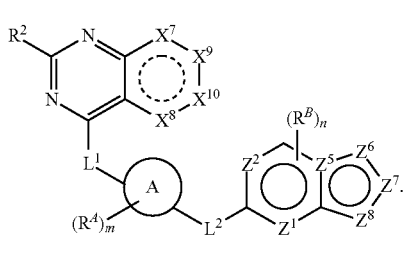

(VII-G)

In certain embodiments, a compound of Formula VII has the structure of Formula VII-J:

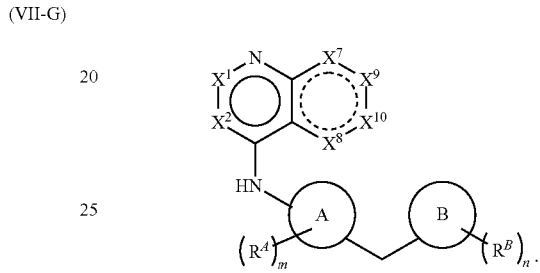

(VII-J)

In certain embodiments, a compound of Formula VII has the structure of Formula VII-H:

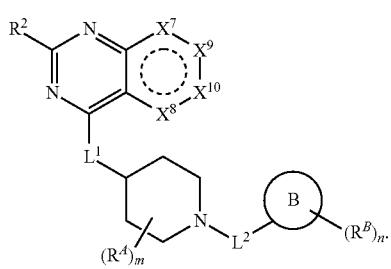

(VII-H)

In certain embodiments, a compound of Formula VII has the structure of Formula VII-K:

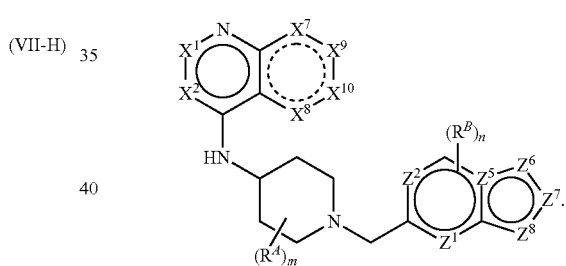

(VII-K)

In certain embodiments, a compound of Formula VII has the structure of Formula VII-I:

A compound of Formula VII may be selected from any one of compounds VII-1 to VII-38 listed in Table 4g. In certain embodiments, a compound of Formula VII is other than the structures listed in Table 4g.

TABLE 4g

Exemplary compounds of Formula VII

| Compound Number | Structure |
| --- | --- |
| VII-1 | (structure shown) |

TABLE 4g-continued

Exemplary compounds of Formula VII

| Compound Number | Structure |
|---|---|
| VII-2 | 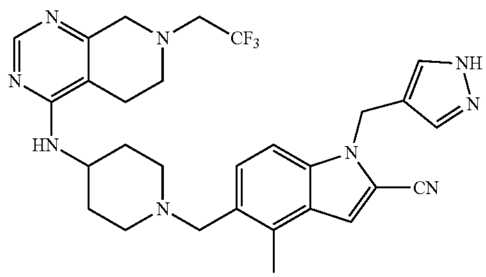 [SMILES: Cc1c(CN2CCC(Nc3ncnc4c3CCN(CC(F)(F)F)C4)CC2)ccc2c1cc(C#N)n2Cc1cn[nH]c1] |
| VII-3 | 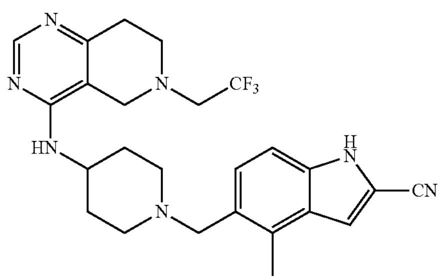 [SMILES: Cc1c(CN2CCC(Nc3ncnc4c3CN(CC(F)(F)F)CC4)CC2)ccc2[nH]c(C#N)cc12] |
| VII-4 | 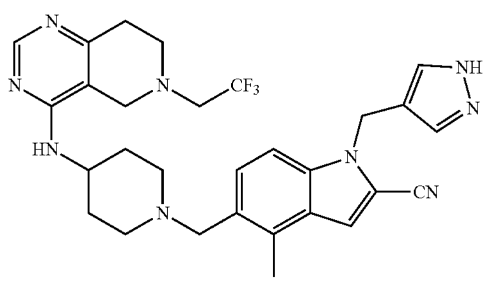 [SMILES: Cc1c(CN2CCC(Nc3ncnc4c3CN(CC(F)(F)F)CC4)CC2)ccc2c1cc(C#N)n2Cc1cn[nH]c1] |
| VII-5 | 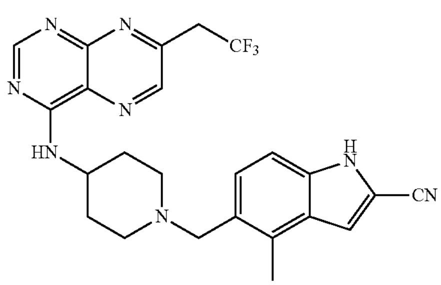 [SMILES: Cc1c(CN2CCC(Nc3ncnc4nc(CC(F)(F)F)cnc34)CC2)ccc2[nH]c(C#N)cc12] |
| VII-6 | 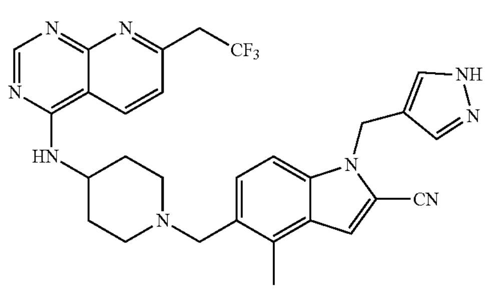 [SMILES: Cc1c(CN2CCC(Nc3ncnc4nc(CC(F)(F)F)ccc34)CC2)ccc2c1cc(C#N)n2Cc1cn[nH]c1] |

TABLE 4g-continued

Exemplary compounds of Formula VII

| Compound Number | Structure |
| --- | --- |
| VII-7 | 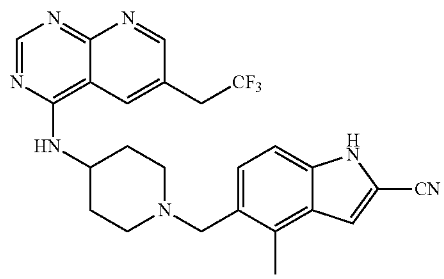 [SMILES: Cc1c(CN2CCC(Nc3ncnc4ncc(CC(F)(F)F)cc34)CC2)ccc2[nH]c(C#N)cc12] |
| VII-8 | 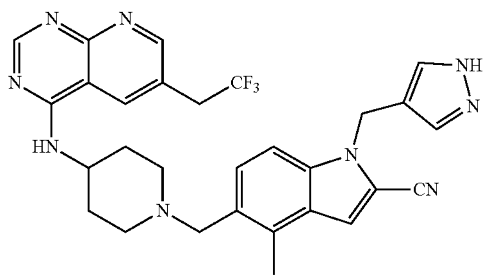 [SMILES: Cc1c(CN2CCC(Nc3ncnc4ncc(CC(F)(F)F)cc34)CC2)ccc2c1cc(C#N)n2Cc1cn[nH]c1] |
| VII-9 | 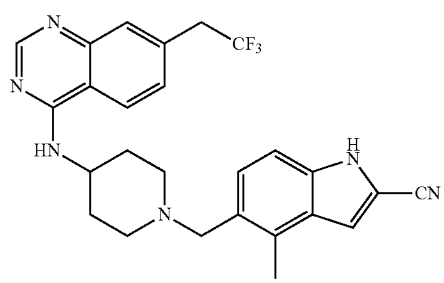 [SMILES: Cc1c(CN2CCC(Nc3ncnc4cc(CC(F)(F)F)ccc34)CC2)ccc2[nH]c(C#N)cc12] |
| VII-10 | 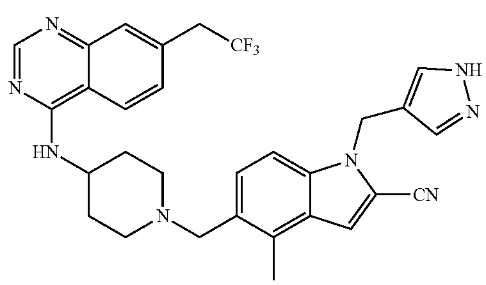 [SMILES: Cc1c(CN2CCC(Nc3ncnc4cc(CC(F)(F)F)ccc34)CC2)ccc2c1cc(C#N)n2Cc1cn[nH]c1] |
| VII-11 | 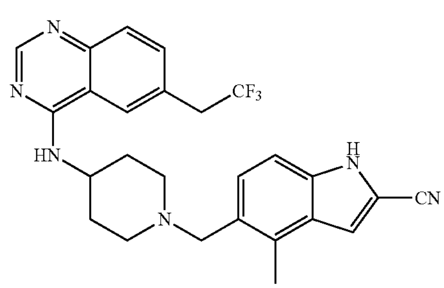 [SMILES: Cc1c(CN2CCC(Nc3ncnc4ccc(CC(F)(F)F)cc34)CC2)ccc2[nH]c(C#N)cc12] |

TABLE 4g-continued
Exemplary compounds of Formula VII
| Compound Number | Structure |
|---|---|
| VII-12 | 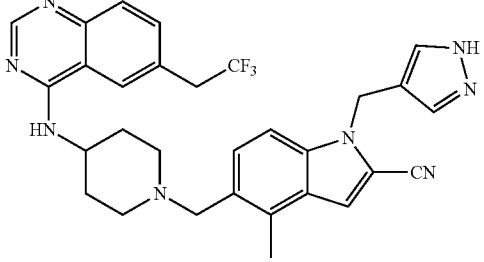 |
| VII-13 | 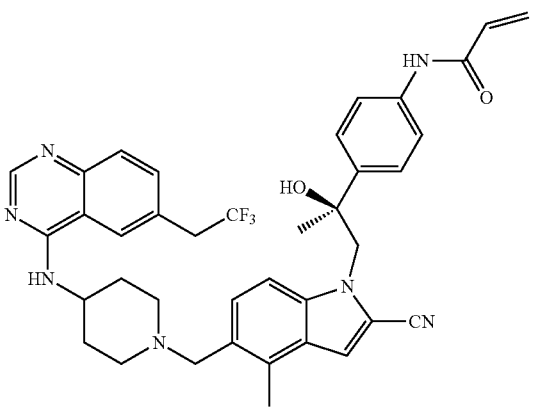 [SMILES: C=CC(=O)Nc1ccc([C@](C)(O)Cn2c(C#N)cc3c(C)c(CN4CCC(Nc5ncnc6ccc(CC(F)(F)F)cc56)CC4)ccc32)cc1] |
| VII-14 | 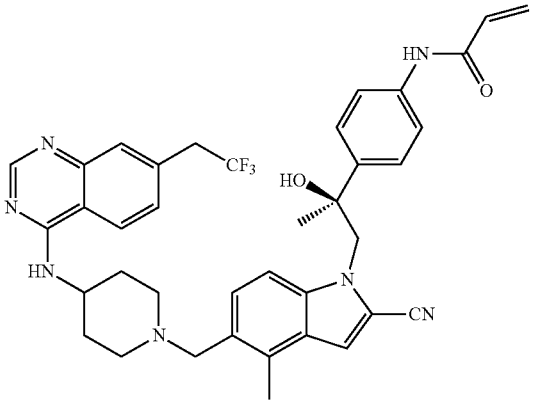 [SMILES: C=CC(=O)Nc1ccc([C@](C)(O)Cn2c(C#N)cc3c(C)c(CN4CCC(Nc5ncnc6cc(CC(F)(F)F)ccc56)CC4)ccc32)cc1] |
| VII-15 | 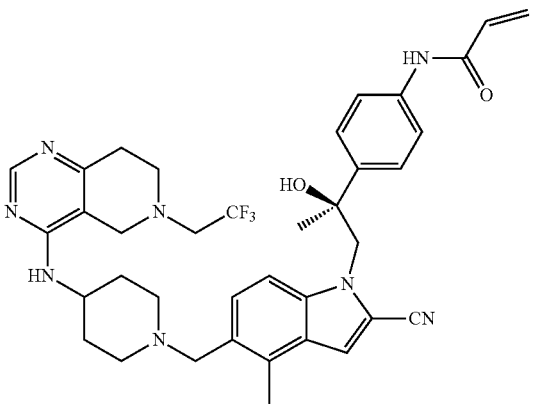 [SMILES: C=CC(=O)Nc1ccc([C@](C)(O)Cn2c(C#N)cc3c(C)c(CN4CCC(Nc5ncnc6c5CN(CC(F)(F)F)CC6)CC4)ccc32)cc1] |

TABLE 4g-continued
Exemplary compounds of Formula VII
| Compound Number | Structure |
| --- | --- |
| VII-16 | 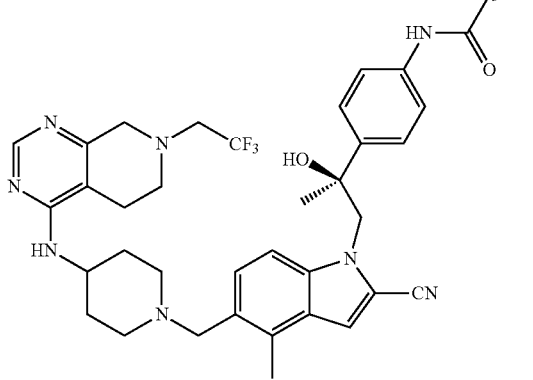 |
| VII-17 | 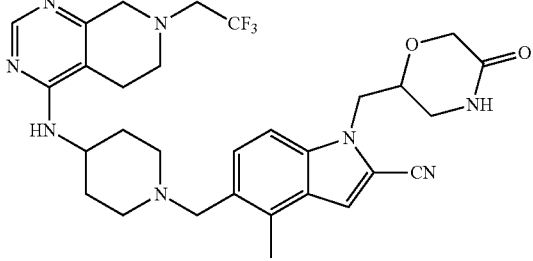 |
| VII-18 | 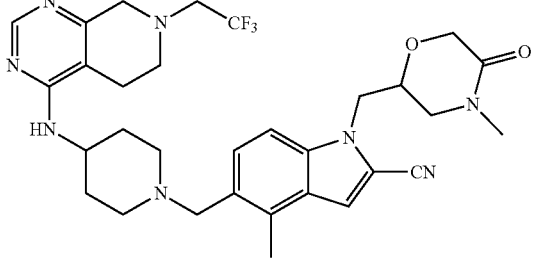 |
| VII-19 | 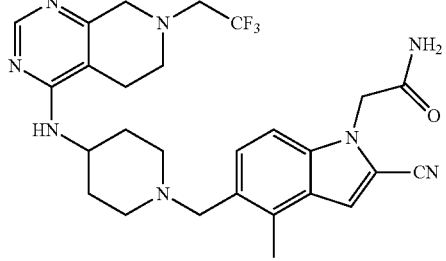 |
| VII-20 | 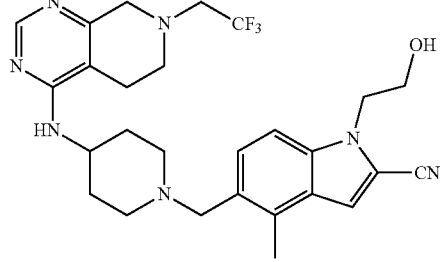 |

TABLE 4g-continued

Exemplary compounds of Formula VII

| Compound Number | Structure |
| --- | --- |
| VII-21 | 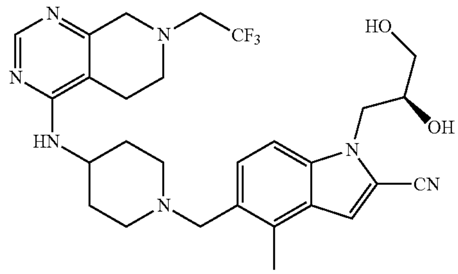 [SMILES: Cc1c(CN2CCC(Nc3ncnc4c3CCN(CC(F)(F)F)C4)CC2)ccc2c1cc(C#N)n2C[C@H](O)CO] |
| VII-22 | 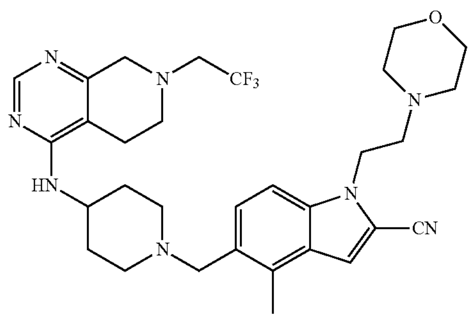 [SMILES: Cc1c(CN2CCC(Nc3ncnc4c3CCN(CC(F)(F)F)C4)CC2)ccc2c1cc(C#N)n2CCN1CCOCC1] |
| VII-23 | 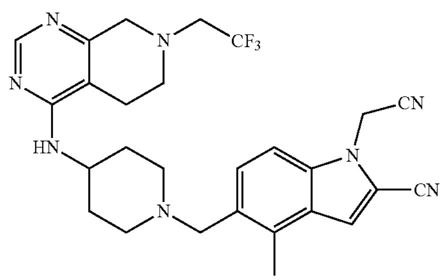 [SMILES: Cc1c(CN2CCC(Nc3ncnc4c3CCN(CC(F)(F)F)C4)CC2)ccc2c1cc(C#N)n2CC#N] |
| VII-24 | 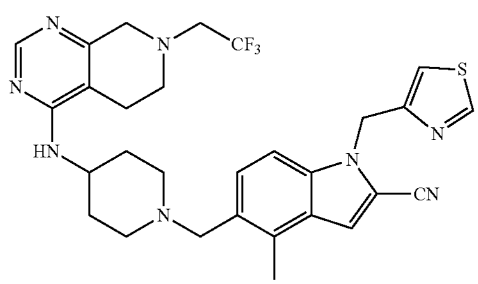 [SMILES: Cc1c(CN2CCC(Nc3ncnc4c3CCN(CC(F)(F)F)C4)CC2)ccc2c1cc(C#N)n2Cc1cscn1] |
| VII-25 | 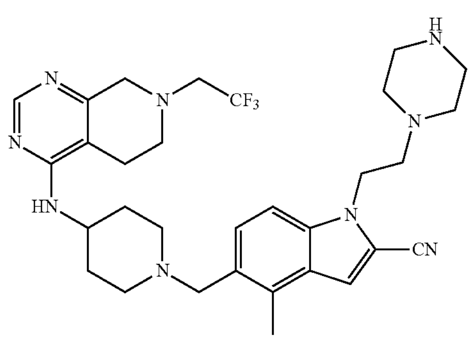 [SMILES: Cc1c(CN2CCC(Nc3ncnc4c3CCN(CC(F)(F)F)C4)CC2)ccc2c1cc(C#N)n2CCN1CCNCC1] |

TABLE 4g-continued

Exemplary compounds of Formula VII

| Compound Number | Structure |
|---|---|
| VII-26 | 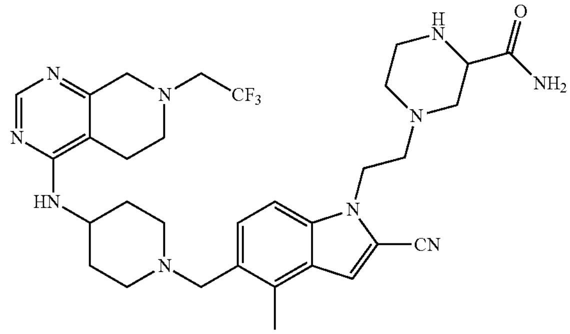 [SMILES: Cc1c(CN2CCC(Nc3ncnc4c3CCN(CC(F)(F)F)C4)CC2)ccc2c1cc(C#N)n2CCN1CCNC(C(N)=O)C1] |
| VII-27 | 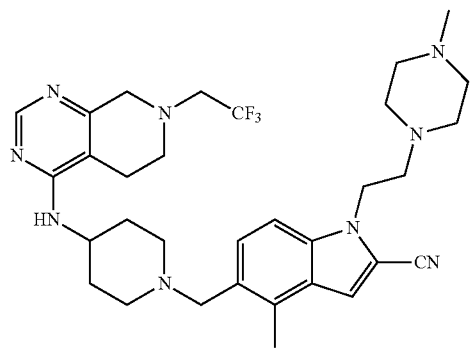 [SMILES: Cc1c(CN2CCC(Nc3ncnc4c3CCN(CC(F)(F)F)C4)CC2)ccc2c1cc(C#N)n2CCN1CCN(C)CC1] |
| VII-28 | 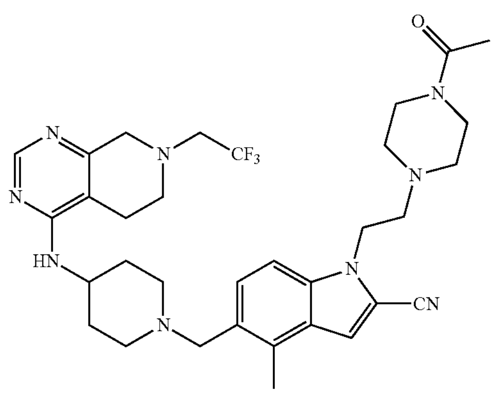 [SMILES: CC(=O)N1CCN(CCn2c(C#N)cc3c(C)c(CN4CCC(Nc5ncnc6c5CCN(CC(F)(F)F)C6)CC4)ccc32)CC1] |
| VII-29 | 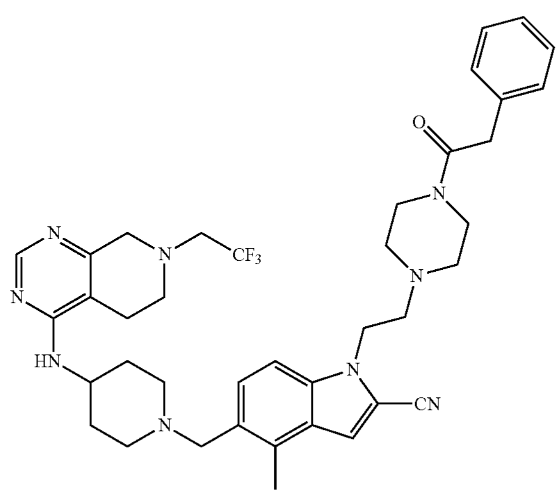 [SMILES: Cc1c(CN2CCC(Nc3ncnc4c3CCN(CC(F)(F)F)C4)CC2)ccc2c1cc(C#N)n2CCN1CCN(C(=O)Cc2ccccc2)CC1] |

TABLE 4g-continued

Exemplary compounds of Formula VII

| Compound Number | Structure |
| --- | --- |
| VII-30 | 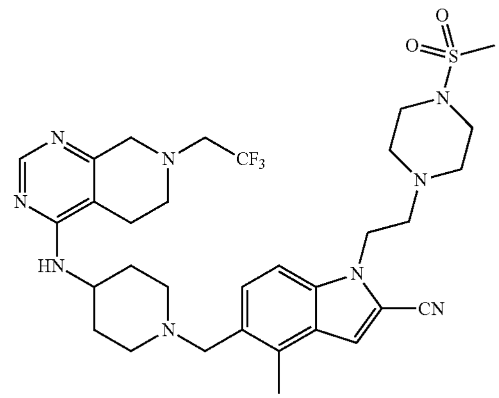 [SMILES: Cc1c(CN2CCC(Nc3ncnc4c3CCN(CC(F)(F)F)C4)CC2)ccc2c1cc(C#N)n2CCN1CCN(S(C)(=O)=O)CC1] |
| VII-31 | 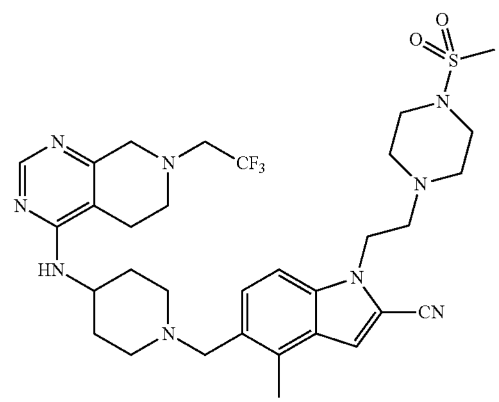 [SMILES: Cc1c(CN2CCC(Nc3ncnc4c3CCN(CC(F)(F)F)C4)CC2)ccc2c1cc(C#N)n2CCN1CCN(S(C)(=O)=O)CC1] |
| VII-32 | 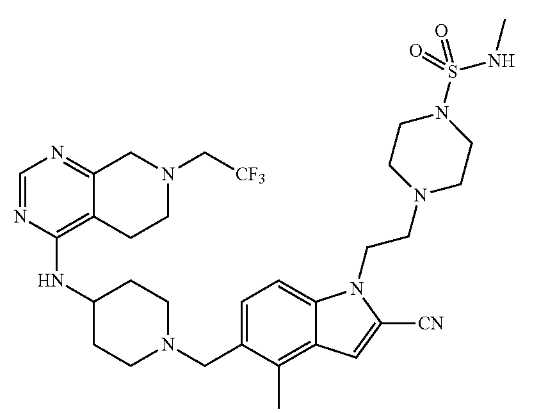 [SMILES: CNS(=O)(=O)N1CCN(CCn2c(C#N)cc3c(C)c(CN4CCC(Nc5ncnc6c5CCN(CC(F)(F)F)C6)CC4)ccc32)CC1] |

TABLE 4g-continued

Exemplary compounds of Formula VII

| Compound Number | Structure |
| --- | --- |
| VII-33 | 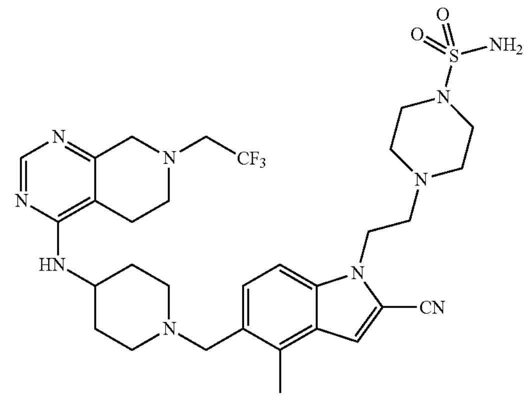 [SMILES: Cc1c(CN2CCC(Nc3ncnc4c3CCN(CC(F)(F)F)C4)CC2)ccc2c1cc(C#N)n2CCN1CCN(S(N)(=O)=O)CC1] |
| VII-34 | 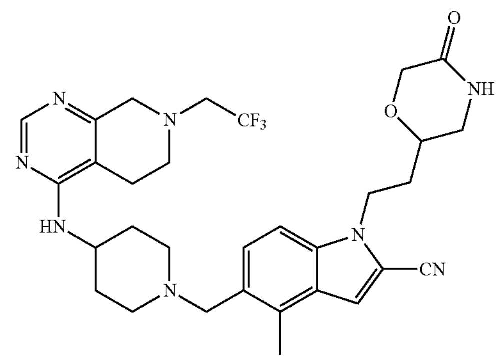 [SMILES: Cc1c(CN2CCC(Nc3ncnc4c3CCN(CC(F)(F)F)C4)CC2)ccc2c1cc(C#N)n2CCC1CNC(=O)CO1] |
| VII-35 | 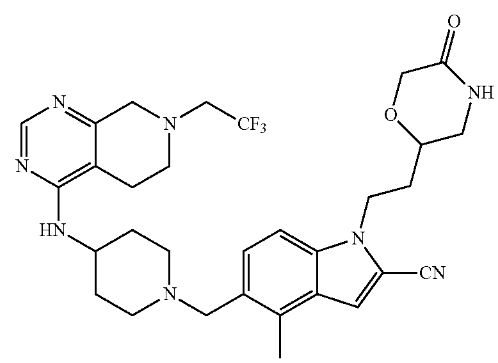 [SMILES: Cc1c(CN2CCC(Nc3ncnc4c3CCN(CC(F)(F)F)C4)CC2)ccc2c1cc(C#N)n2CCC1CNC(=O)CO1] |
| VII-36 | 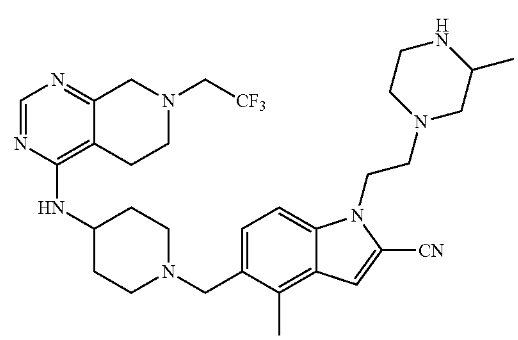 [SMILES: Cc1c(CN2CCC(Nc3ncnc4c3CCN(CC(F)(F)F)C4)CC2)ccc2c1cc(C#N)n2CCN1CCNC(C)C1] |

TABLE 4g-continued

Exemplary compounds of Formula VII

| Compound Number | Structure |
| --- | --- |
| VII-37 | 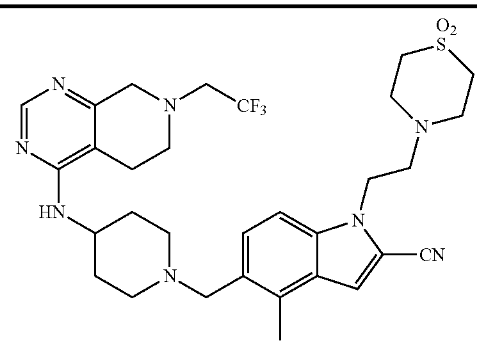 |
| VII-38 | 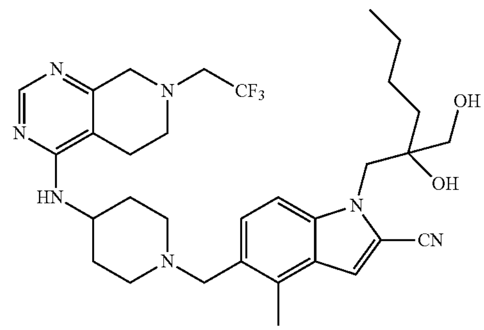 [SMILES: CCCCC(O)(CO)Cn1c(C#N)cc2c(C)c(CN3CCC(Nc4ncnc5c4CCN(CC(F)(F)F)C5)CC3)ccc21] |

In some embodiments of a compound of Formula VII or pharmaceutically acceptable salts thereof, the compound comprises an $R^B$ selected from:

wherein:
G is selected from a bond, alkylene, heteroalkylene, $C_{3-12}$ carbocycle, 3- to 12-membered heterocycle, and combinations thereof, wherein G is optionally substituted with one or more $R^{32}$ groups;

V is absent or selected from a $C_{3-12}$ carbocycle, and 3- to 12-membered heterocycle; wherein V is optionally substituted with one or more $R^{32}$ groups;

each of $R^{21}$ and $R^{32}$ is, at each occurrence, independently selected from:
H, halogen, —$OR^{20}$, —$SR^{20}$, —$N(R^{20})_2$, —$N(R^{20})C(O)R^{20}$, —$C(O)R^{20}$, —$C(O)OR^{20}$, —$C(O)N(R^{20})_2$, —$OC(O)R^{20}$, —$S(O)_2R^{20}$, —$S(O)_2N(R^{20})_2$, —$N(R^{20})S(O)_2R^{20}$, —$NO_2$, =O, =S, =$N(R^{20})$, —$P(O)(OR^{20})_2$, —$P(O)(R^{20})_2$, —$OP(O)(OR^{20})_2$, and —CN;

$C_{1-6}$ alkyl, $C_{2-6}$ alkenyl, and $C_{2-6}$ alkynyl, each of which is independently optionally substituted at each occurrence with one or more substituents selected from halogen, —$OR^{20}$, —$SR^{20}$, —$N(R^{20})_2$, —$N(R^{20})C(O)R^{20}$, —$C(O)R^{20}$, —$C(O)OR^{20}$, —$C(O)N(R^{20})_2$, —$OC(O)R^{20}$, —$S(O)_2R^{20}$, —$S(O)_2N(R^{20})_2$, —$N(R^{20})S(O)_2R^{20}$, —$NO_2$, =O, =S, =$N(R^{20})$, —$P(O)(OR^{20})_2$, —$P(O)(R^{20})_2$, —$OP(O)(OR^{20})_2$, —CN, $C_{3-10}$ carbocycle, and 3- to 10-membered heterocycle; and $C_{3-10}$ carbocycle and 3- to 10-membered heterocycle; wherein two $R^{32}$ on the same carbon atom can come together to form a $C_{3-10}$ carbocycle or 3- to 10-membered heterocycle;

wherein each $C_{3-10}$ carbocycle and 3- to 10-membered heterocycle of $R^{32}$ is independently optionally substituted with one or more substituents selected from halogen, —$OR^{20}$, —$SR^{20}$, —$N(R^{20})_2$, —$N(R^{20})C(O)R^2$, —$C(O)R^{20}$, —$C(O)OR^{20}$, —$C(O)N(R^{20})_2$, —$OC(O)R^{20}$, —$S(O)_2R^{20}$, —$S(O)_2N(R^{20})_2$, —$N(R^{20})S(O)_2R^{20}$, —$NO_2$, =O, =S, =$N(R^{20})$, —$P(O)(OR^{20})_2$, —$P(O)(R^{20})_2$, —$OP(O)(OR^{20})_2$, —CN, $C_{1-6}$ alkyl, $C_{2-6}$ alkenyl, and $C_{2-6}$ alkynyl;

$R^{20}$ at each occurrence is independently selected from:
hydrogen;
$C_{1-6}$ alkyl, $C_{2-6}$ alkenyl, and $C_{2-6}$ alkynyl, each of which is independently optionally substituted at each occurrence with one or more substituents selected from halogen, —$OR^{30}$, —$SR^{30}$, —$N(R^{30})_2$, —$N(R^{30})C(O)R^{30}$, —$C(O)R^{30}$, —$C(O)OR^{30}$, —$C(O)N(R^{30})_2$, —$OC(O)R^{30}$, —$S(O)_2R^{30}$, —$S(O)_2N(R^{30})_2$, —$N(R^{30})S(O)_2R^{30}$, —$NO_2$, —$P(O)(OR^{30})_2$, —$P(O)(R^{30})_2$, —$OP(O)(OR^{30})_2$, and —CN; and 3- to 10-membered heterocycle and $C_{3-10}$ carbocycle; and $R^{30}$ at each occurrence is independently selected from hydrogen, $C_{1-6}$ alkyl, $C_{2-6}$ alkenyl, and $C_{2-6}$ alkynyl.

In some embodiments of a compound of Formula VII or pharmaceutically acceptable salts thereof, $R^{21}$ is a moiety with 5 to 50 atoms, such as a moiety with 5 to 40 atoms.

In some embodiments, V is selected from a 3-8 membered saturated ring, 3-8 membered unsaturated ring, 4-10 membered fused bicyclic ring, and 5-11 membered spiro bicyclic ring. V may be optionally substituted with one or more $R^{32}$ groups, such as with 1, 2, 3, 4, or 5 $R^{32}$ groups. In some embodiments, V is a 3-7 membered saturated ring, such as a 3-7 membered cycloalkyl or 3-7 membered aromatic or non-aromatic heterocycle. In some embodiments, V is a 3-7 membered unsaturated ring, such as a 6 membered aryl, 5-6 membered heteroaryl, or 3-7 membered cycloalkenyl.

In some embodiments of a compound of Formula VII or pharmaceutically acceptable salts thereof, V is selected from a 3-8 membered saturated ring optionally substituted with one or more $R^{32}$ groups. In some embodiments of a compound of Formula VII or pharmaceutically acceptable salts thereof, V is a 3-, 4-, 5-, 6- or 7-membered saturated carbocycle, any one of which is optionally substituted with one or more $R^{32}$ groups. In some embodiments of a compound of Formula VII or pharmaceutically acceptable salts thereof, V is selected from:

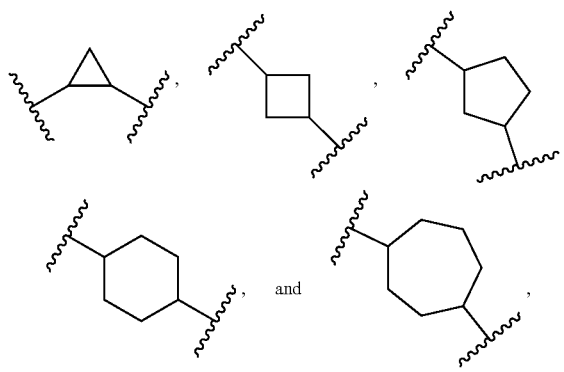

any one of which is optionally substituted with one or more $R^{32}$ groups.

In some embodiments of a compound of Formula VII or pharmaceutically acceptable salts thereof, V is a 4-, 5-, 6-, 7- or 8-membered saturated heterocycle, any one of which is optionally substituted with one or more $R^{32}$ groups. In some embodiments of a compound of Formula VII or pharmaceutically acceptable salts thereof, V is selected from azetidine, oxetane, piperidine, oxane, piperazine, pyrrolidine, tetrahydrofuran, thiolane, imidazolidine, morpholine, thiomorpholine, azepane, and homopiperazine, any one of which is optionally substituted with one or more $R^{32}$ groups. In some embodiments of a compound of Formula VII or pharmaceutically acceptable salts thereof, V is selected from:

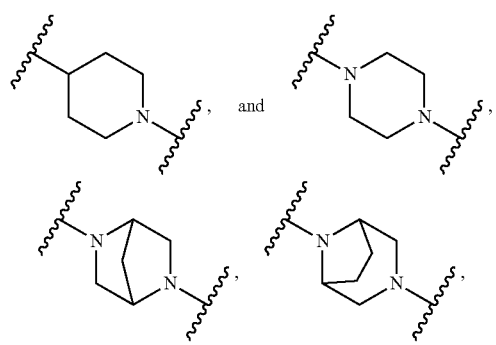

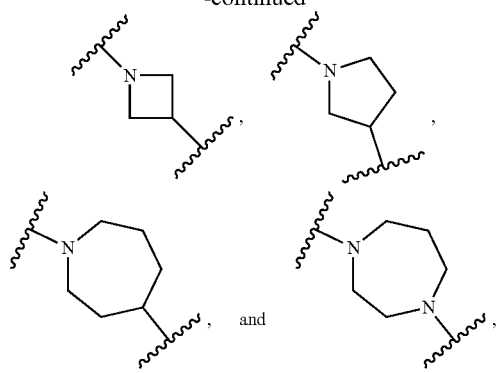

any one of which is optionally substituted with one or more $R^{32}$ groups.

In some embodiments of a compound of Formula VII or pharmaceutically acceptable salts thereof, V is a bicyclic heterocycle, optionally substituted with one or more $R^{32}$ groups. In some embodiments of a compound of Formula VII or pharmaceutically acceptable salts thereof, V is selected from

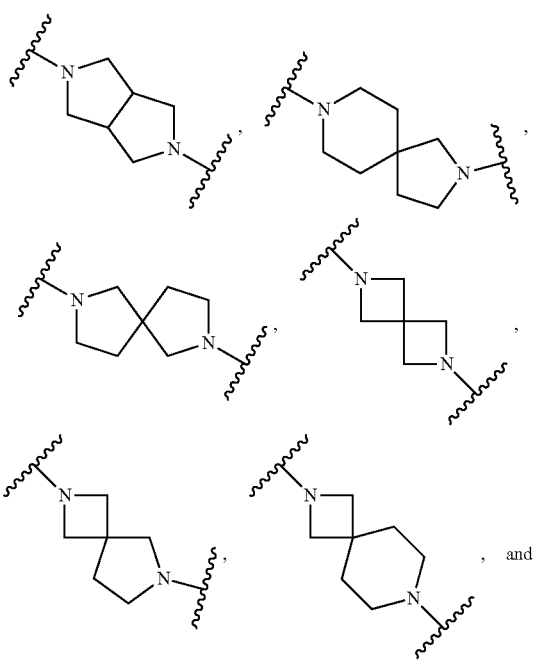

any one of which is optionally substituted with one or more $R^{32}$ groups.

In certain embodiments, V is a 4-10 membered fused bicyclic ring, such as a 8-10 membered fused bicyclic ring. In certain embodiments, the fused bicyclic ring includes one or more heteroatoms such as one or more atoms selected from N, O, and S. In certain embodiments, the fused bicyclic ring includes two heteroatoms such as two nitrogen atoms. Each of the rings of the fused bicyclic ring may be saturated or unsaturated. In particular embodiments, both rings of the fused bicyclic ring are saturated. Non-limiting examples of V comprising a fused bicyclic ring include and

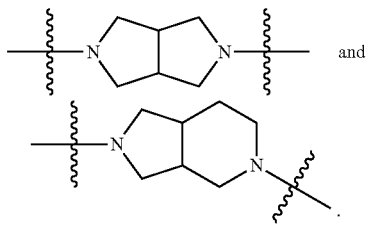

In some embodiments, V is a 5-11 membered spiro bicyclic ring, such as a 7-11 membered spiro bicyclic ring. In certain embodiments, the fused bicyclic ring includes one or more heteroatoms such as one or more atoms selected from N, O, and S. In particular embodiments, the fused bicyclic ring includes two heteroatoms such as two nitrogen atoms. Non-limiting examples of V comprising a spiro bicyclic ring include

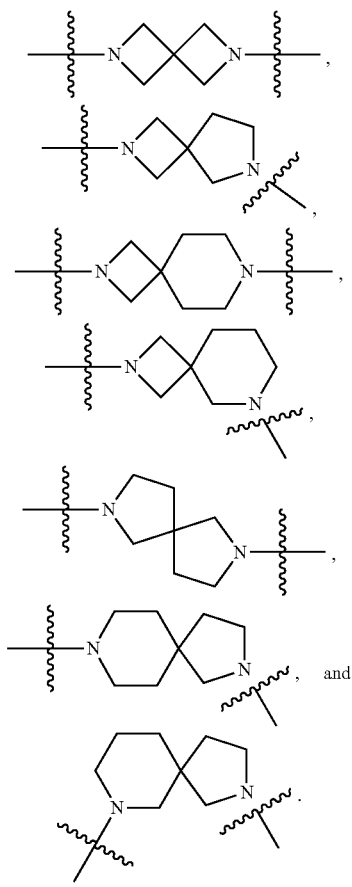

In some embodiments of a compound of Formula VII or pharmaceutically acceptable salts thereof, V is selected from an unsaturated, aromatic, or heteroaromatic ring, any one of which is optionally substituted with one or more $R^{32}$ groups. In some embodiments of a compound of Formula VII or pharmaceutically acceptable salts thereof, V is selected from phenyl, pyridine, pyrazine, pyrimidine, pyridazine, naphthalene, anthracene, quinoline, isoquinoline, quinoxaline, acridine, quinazoline, cinnoline, phthalazine, furan, dihydrofuran, thiophene, dihydrothiophene, imidazole, imidazoline, oxazole, oxazoline, pyrrole, dihydropyrrole, thiazole, dihydrothiazole, pyrazole, dihydropyrazole, isoxazole, dihydroisoxazole, isothiazole, dihydroisothiazole, benzofuran, isobenzofuran, indole, isoindole, benzothiophene, benzimidazole, purine, indazole, benzoxazole, benzisoxazole, and benzothiazole, any one of which is optionally substituted with one or more $R^{32}$ groups. In some embodiments of a compound of Formula VII or pharmaceutically acceptable salts thereof, V is phenyl, optionally substituted with one or more $R^{32}$ groups. In some embodiments of a compound of Formula VII or pharmaceutically acceptable salts thereof, V is a heteroaromatic ring optionally substituted with one or more $R^{32}$ groups. In some embodiments of a compound of Formula VII or pharmaceutically acceptable salts thereof, V is selected from pyridine, pyrazine, pyrimidine, pyridazine, naphthalene, anthracene, quinoline, isoquinoline, quinoxaline, acridine, quinazoline, cinnoline, phthalazine, furan, thiophene, imidazole, oxazole, pyrrole, thiazole, pyrazole, isoxazole, isothiazole, benzofuran, isobenzofuran, indole, isoindole, benzothiophene, benzimidazole, purine, indazole, benzoxazole, benzisoxazole, and benzothiazole, any one of which is optionally substituted with one or more $R^{32}$ groups. In some embodiments of a compound of Formula VII or pharmaceutically acceptable salts thereof, V is selected from

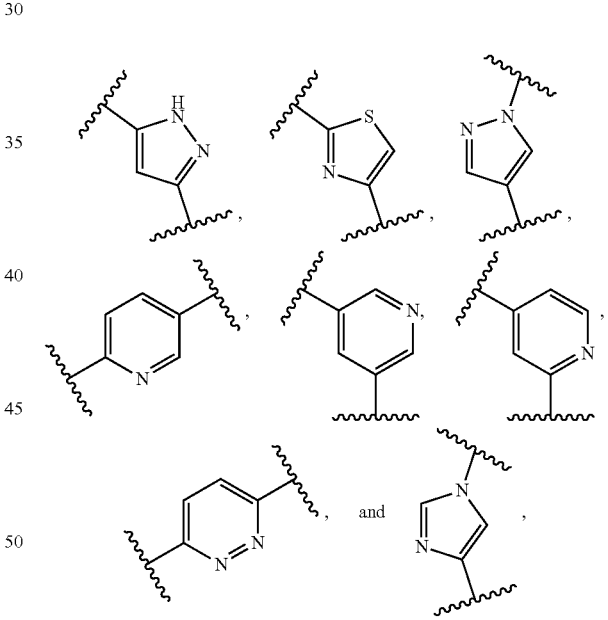

wherein any one of which is optionally substituted with one or more $R^{32}$ groups.

In some embodiments of a compound of Formula VII or pharmaceutically acceptable salts thereof, V is absent.

In some embodiments of a compound of Formula VII or pharmaceutically acceptable salts thereof, G is a bond.

In some embodiments of a compound of Formula VII or pharmaceutically acceptable salts thereof, G is alkylene optionally substituted with one or more $R^{32}$ groups.

In some embodiments of a compound of Formula VII or pharmaceutically acceptable salts thereof, G is selected from methylene, ethylene, propylene, and butylene, any one of which is optionally substituted with one or more $R^{32}$ groups.

In some embodiments of a compound of Formula VII or pharmaceutically acceptable salts thereof, G is selected from:

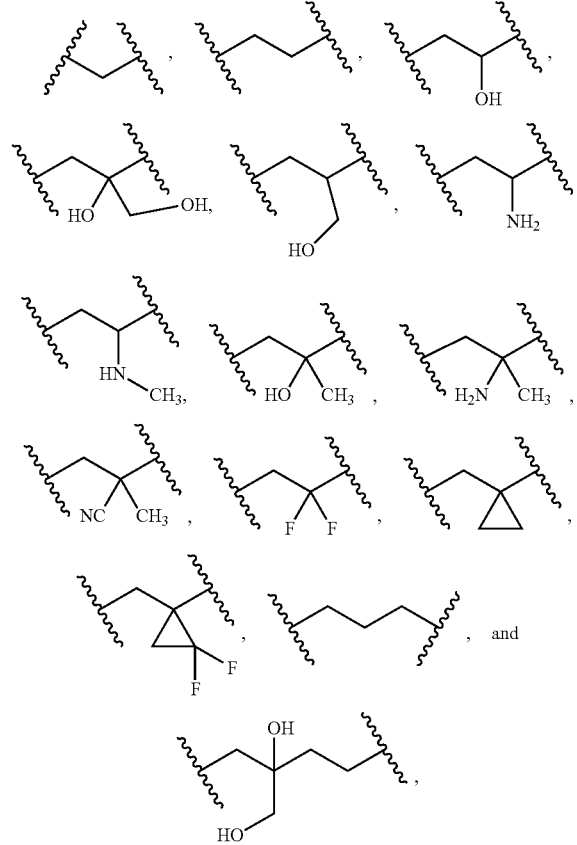

wherein any one of which is optionally substituted with one or more $R^{32}$ groups.

In some embodiments of a compound of Formula VII or pharmaceutically acceptable salts thereof, G is a heteroalkylene optionally substituted with one or more $R^{32}$ groups.

In some embodiments of a compound of Formula VII or pharmaceutically acceptable salts thereof, G is a $C_{3-10}$ carbocycle or 3- to 10-membered heterocycle, any one of which is optionally substituted with one or more $R^{32}$ groups.

In some embodiments of a compound of Formula VII or pharmaceutically acceptable salts thereof, G is a saturated $C_{3-10}$ carbocycle or saturated 3- to 10-membered heterocycle, any one of which is optionally substituted with one or more $R^{32}$ groups.

In some embodiments of a compound of Formula VII or pharmaceutically acceptable salts thereof, G is selected from:

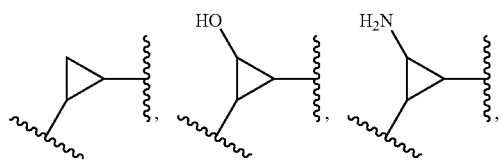

-continued

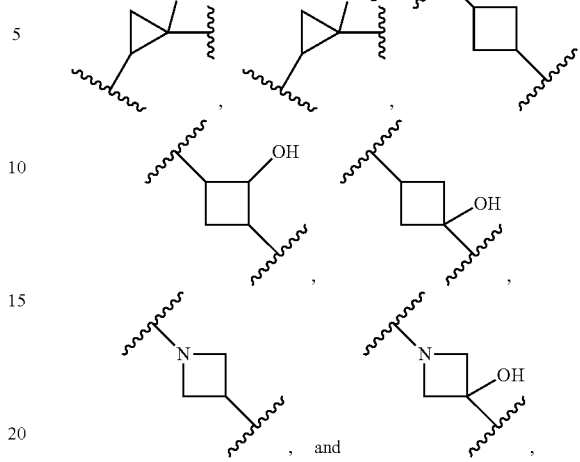

wherein any one of which is optionally substituted with one or more $R^{32}$ groups.

In some embodiments, the compound is selected from Table 4g.

In certain aspects, compounds of the disclosure covalently bond with menin and inhibit the interaction of menin with MLL. Such bonding may lead to an increase in the affinity of the compound for menin, which is an advantageous property in many applications, including therapeutic and diagnostic uses. In certain embodiments, the compounds of the disclosure comprise electrophilic groups capable of reacting with a nucleophilic group present in a menin protein. Suitable electrophilic groups are described throughout the application, while suitable nucleophilic groups include, for example, cysteine moieties present in the binding domain of a menin protein. Without wishing to be bound by theory, a cysteine residue in the menin binding domain may react with the electrophilic group of a compound of the disclosure, leading to formation of a conjugate product. In certain embodiments, the compounds of the disclosure are capable of covalently bonding to the cysteine residue at position 329 of a menin isoform 2 (SEQ ID NO: 2) or cysteine 334 in menin isoform 1 (SEQ ID NO: 1). In certain embodiments, the disclosure provides a conjugate of a compound of the disclosure with a menin protein. For example, the disclosure provides a conjugate of a compound of the invention with menin, bound at the cysteine residue 329 of menin isoform 2 (SEQ ID NO: 2) or cysteine 334 in menin isoform 1 (SEQ ID NO: 1).

In some embodiments of a compound of Formula VII or pharmaceutically acceptable salts thereof, one or more of $R^2, R^5, R^6, R^7, R^8, R^9, R^{10}, R^{11}, R^{12}, R^{13}, R^{16}, R^{17}, R^{18}, R^{19}, R^A$, and $R^B$, when present, comprises a functional group that covalently reacts with one or more residues on menin. In some embodiments of a compound provided herein, the functional group covalently reacts with one or more cysteine residues on menin. In some embodiments of a compound provided herein, the functional group covalently reacts with a cysteine on menin at position 329 relative to SEQ ID NO: 2 when optimally aligned or position 334 relative to SEQ ID NO: 1 when optimally aligned. In certain embodiments, the functional group covalently reacts with one or more residues on menin selected from cysteine 329, cysteine 241, and/or cysteine 230 on menin relative to SEQ ID NO: 2 when optimally aligned. In certain embodiments, the functional group covalently reacts with cysteine 329 relative to SEQ ID NO: 2 when optimally aligned.

In certain embodiments of a compound of Formula VII or pharmaceutically acceptable salts thereof, one or more of $R^2$, $R^5$, $R^6$, $R^7$, $R^8$, $R^9$, $R^{10}$, $R^{11}$, $R^{12}$, $R^{13}$, $R^{16}$, $R^{17}$, $R^{18}$, $R^{19}$, $R^A$, and $R^B$, when present, comprises a moiety that covalently reacts with one or more residues on menin. In particular embodiments, one or more of $R^2$, $R^5$, $R^6$, $R^7$, $R^8$, $R^9$, $R^{10}$, $R^{11}$, $R^{12}$, $R^{13}$, $R^{16}$, $R^1$, $R^{18}$, $R^{19}$, $R^A$, and $R^B$, when present, comprises a moiety that covalently reacts with any one or more isoforms of menin, for example, isoform 1 (SEQ ID NO: 1), isoform 2 (SEQ ID NO: 2) or isoform 3 (SEQ ID NO: 3) of menin. In certain embodiments, one or more of $R^2$, $R^5$, $R^6$, $R^7$, $R^8$, $R^9$, $R^{10}$, $R^{11}$, $R^{12}$, $R^{13}$, $R^{16}$, $R^{17}$, $R^{18}$, $R^{19}$, $R^A$, and $R^B$, when present, comprises a moiety that covalently reacts with menin, wherein the menin protein shares 60% or more, 70% or more, 75% or more, 80% or more, 85% or more, 90% or more, 95% or more, or 99% or more sequence identity with isoform 1 (SEQ ID NO: 1), isoform 2 (SEQ ID NO: 2) or isoform 3 (SEQ ID NO: 3).

In certain embodiments, for a compound or salt of Formula VII, one or more of $R^2$, $R^5$, $R^6$, $R^7$, $R^8$, $R^9$, $R^{10}$, $R^{11}$, $R^{12}$, $R^{13}$, $R^{16}$, $R^{17}$, $R^{18}$, $R^{19}$, $R^A$, and $R^B$, when present, comprises an electrophilic group that is susceptible to nucleophilic attack from a residue on menin. Included in the present disclosure are all electrophilic moieties that are known by one of skill in the art to bind to nucleophilic residues, for example, any electrophilic moiety known to bind to cysteine residues. In certain embodiments, for a compound or salt of Formula VII, one or more of $R^2$, $R^5$, $R^6$, $R^7$, $R^8$, $R^9$, $R^{10}$, $R^{11}$, $R^{12}$, $R^{13}$, $R^{16}$, $R^{17}$, $R^{18}$, $R^{19}$, $R^A$, and $R^B$, when present, comprises a moiety other than an electrophile wherein the moiety is capable of binding or covalently reacting with a residue on menin. In particular embodiments, for a compound or salt of Formula VII, one or more of $R^2$, $R^5$, $R^6$, $R^7$, $R^8$, $R^9$, $R^{10}$, $R^{11}$, $R^{12}$, $R^{13}$, $R^{16}$, $R^{17}$, $R^{18}$, $R^{19}$, $R^A$, and $R^B$, when present, comprises a moiety that covalently reacts with one or more cysteine residues on menin, for example, one or more of cysteine 329, cysteine 241, and cysteine 230 relative to SEQ ID NO: 2 when optimally aligned. In certain embodiments, one or more of $R^2$, $R^5$, $R^6$, $R^7$, $R^8$, $R^9$, $R^{10}$, $R^{11}$, $R^{12}$, $R^{13}$, $R^{16}$, $R^{17}$, $R^{18}$, $R^{19}$, $R^A$, and $R^B$, when present, comprises a moiety that covalently reacts with cysteine 329 in menin isoform 2 (SEQ ID NO: 2) or cysteine 334 in menin isoform 1 (SEQ ID NO: 1). In certain embodiments, a compound or salt of Formula VII, is capable of (a) binding covalently to menin and (b) inhibiting the iteration of menin and MLL.

In some embodiments of a compound of Formula VII or pharmaceutically acceptable salts thereof, the compound is capable of (a) binding covalently to menin and (b) inhibiting the iteration of menin and MLL.

In some embodiments of a compound of Formula VII or pharmaceutically acceptable salts thereof, $R^{21}$ comprises a functional group that covalently reacts with one or more residues on menin. In some embodiments of a compound provided herein, the functional group covalently reacts with one or more cysteine residues on menin. In some embodiments of a compound provided herein, the functional group covalently reacts with a cysteine on menin at position 329 relative to SEQ ID NO: 2 when optimally aligned or position 334 relative to SEQ ID NO: 1 when optimally aligned.

In some embodiments of a compound of Formula VII or pharmaceutically acceptable salts thereof, $R^{21}$ is a moiety comprising an alpha, beta-unsaturated carbonyl; an alpha, beta-unsaturated sulfonyl; an epoxide; an aldehyde; sulfonyl fluoride; a halomethylcarbonyl; a dihalomethylcarbonyl; or a trihalomethylcarbonyl.

In some embodiments of a compound of Formula VII or pharmaceutically acceptable salts thereof, $R^{21}$ is selected from:

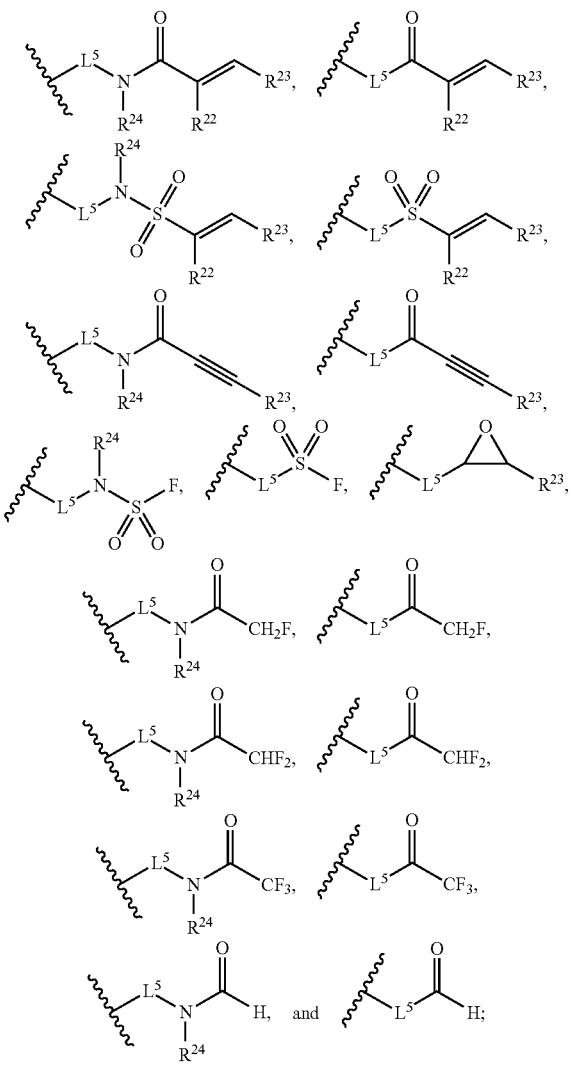

wherein:
$L^5$ is selected from a bond; and $C_{1-6}$ alkylene, $C_{1-6}$ heteroalkylene, $C_{2-6}$ alkenylene, and $C_{2-6}$ alkynylene, each of which is independently optionally substituted with one or more $R^{32}$ groups;
$R^{22}$ and $R^{23}$ are selected from
hydrogen, halogen, $-OR^{20}$, $-SR^{20}$, $-N(R^{20})_2$, $-N(R^{20})C(O)R^{20}$, $-C(O)R^{20}$, $-C(O)OR^{20}$, $-C(O)N(R^{20})_2$, $-OC(O)R^{20}$, $-S(O)_2R^{20}$, $-S(O)_2N(R^{20})_2$, $-N(R^{20})S(O)_2R^{20}$, $-NO_2$, $=O$, $=S$, $=N(R^{20})$, $-P(O)(OR^{20})_2$, $-P(O)(R^{20})_2$, $-OP(O)(OR^{20})_2$, and $-CN$;
$C_{1-6}$ alkyl, $C_{2-6}$ alkenyl, and $C_{2-6}$ alkynyl, each of which is independently optionally substituted at each occurrence with one or more substituents selected from halogen, $-OR^{20}$, $-SR^{20}$, $-N(R^{20})_2$, $-N(R^{20})C(O)R^{20}$, $-C(O)R^{20}$, $-C(O)OR^{20}$, —C(O)N($R^{20}$)$_2$, —OC(O)$R^{20}$, —S(O)$_2R^{20}$, —S(O)$_2$N($R^{20}$)$_2$, —N($R^{20}$)S(O)$_2R^{20}$, —NO$_2$, =O, =S, =N($R^{20}$), —P(O)(O$R^{20}$)$_2$, —P(O)($R^{20}$)$_2$, —OP(O)(O$R^{20}$)$_2$, —CN, $C_{3-10}$ carbocycle, and 3- to 10-membered heterocycle; and $C_{3-10}$ carbocycle and 3- to 10-membered heterocycle, wherein each $C_{3-10}$ carbocycle and 3- to 10-membered heterocycle of $R^{22}$ and $R^{23}$ is independently optionally substituted with one or more substituents selected from halogen, —O$R^{20}$, —S$R^{20}$, —N($R^{20}$)$_2$, —N($R^{20}$)C(O)$R^{20}$, —C(O)$R^{20}$, —C(O)O$R^{20}$, —C(O)N($R^{20}$)$_2$, —OC(O)$R^{20}$, —S(O)$_2R^{20}$, —S(O)$_2$N($R^{20}$)$_2$, —N($R^{20}$)S(O)$_2R^{20}$, —NO$_2$, =O, =S, =N($R^{20}$), —P(O)(O$R^{20}$)$_2$, —P(O)($R^{20}$)$_2$, —OP(O)(O$R^{20}$)$_2$, —CN, $C_{1-6}$ alkyl, $C_{2-6}$ alkenyl, and $C_{2-6}$ alkynyl; or $R^{22}$ and $R^{23}$, together with the carbon atoms to which they are attached, form a carbocyclic ring;

$R^{24}$ is selected from:
hydrogen, —C(O)$R^{20}$, —C(O)O$R^{20}$, —C(O)N($R^{20}$)$_2$, —OC(O)$R^{20}$, —S(O)$_2R^{20}$, and —S(O)$_2$N($R^{20}$)$_2$;

$C_{1-6}$ alkyl, $C_{2-6}$ alkenyl, and $C_{2-6}$ alkynyl, each of which is independently optionally substituted at each occurrence with one or more substituents selected from halogen, —O$R^{20}$, —S$R^{20}$, —N($R^{20}$)$_2$, —N($R^{20}$)C(O)$R^{20}$, —C(O)$R^{20}$, —C(O)O$R^{20}$, —C(O)N($R^{20}$)$_2$, —OC(O)$R^{20}$, —S(O)$_2R^{20}$, —S(O)$_2$N($R^{20}$)$_2$, —N($R^{20}$)S(O)$_2R^{20}$, —NO$_2$, =O, =S, =N($R^{20}$), —P(O)(O$R^{20}$)$_2$, —P(O)($R^{20}$)$_2$, —OP(O)(O$R^{20}$)$_2$, —CN, $C_{3-10}$ carbocycle, and 3- to 10-membered heterocycle; and $C_{3-10}$ carbocycle and 3- to 10-membered heterocycle, wherein each $C_{3-10}$ carbocycle and 3- to 10-membered heterocycle of $R^{24}$ is independently optionally substituted with one or more substituents selected from halogen, —O$R^{20}$, —S$R^{20}$, —N($R^{20}$)$_2$, —N($R^{20}$)C(O)$R^{20}$, —C(O)$R^{20}$, —C(O)O$R^{20}$, —C(O)N($R^{20}$)$_2$, —OC(O)$R^{20}$, —S(O)$_2R^{20}$, —S(O)$_2$N($R^{20}$)$_2$, —N($R^{20}$)S(O)$_2R^{20}$, —NO$_2$, =O, =S, =N($R^{20}$), —P(O)(O$R^{20}$)$_2$, —P(O)($R^{20}$)$_2$, —OP(O)(O$R^{20}$)$_2$, —CN, $C_{1-6}$ alkyl, $C_{2-6}$ alkenyl, and $C_{2-6}$ alkynyl.

In some embodiments of a compound of Formula VII or pharmaceutically acceptable salts thereof, $L^5$ is a bond. In some embodiments of a compound of Formula VII or pharmaceutically acceptable salts thereof, $L^5$ is optionally substituted $C_{1-6}$ alkylene. In some embodiments of a compound of Formula VII or pharmaceutically acceptable salts thereof, $L^5$ is selected from methylene, ethylene or propylene. In some embodiments of a compound of Formula VII or pharmaceutically acceptable salts thereof, $L^5$ is substituted with one or more substituents selected from halogen, —NO$_2$, =O, =S, —O$R^{20}$, —S$R^{20}$, and —N($R^{20}$)$_2$.

In some embodiments of a compound of Formula VII or pharmaceutically acceptable salts thereof, $R^{23}$ is selected from:
hydrogen;
$C_{1-6}$ alkyl, $C_{2-6}$ alkenyl, and $C_{2-6}$ alkynyl, each of which is independently optionally substituted at each occurrence with one or more substituents selected from halogen, —O$R^{20}$, —S$R^{20}$, —N($R^{20}$)$_2$, —N($R^{20}$)C(O)$R^{20}$, —C(O)$R^{20}$, —C(O)O$R^{20}$, —C(O)N($R^{20}$)$_2$, —OC(O)$R^{20}$, —S(O)$_2R^{20}$, —S(O)$_2$N($R^{20}$)$_2$, —N($R^{20}$)S(O)$_2R^{20}$, —NO$_2$, =O, =S, =N($R^{20}$), —P(O)(O$R^{20}$)$_2$, —P(O)($R^{20}$)$_2$, —OP(O)(O$R^{20}$)$_2$, —CN, $C_{3-10}$ carbocycle, and 3- to 10-membered heterocycle; and $C_{3-10}$ carbocycle, and 3- to 10-membered heterocycle, wherein each $C_{3-10}$ carbocycle and 3- to 10-membered heterocycle is independently optionally substituted with one or more substituents selected from halogen, —O$R^{20}$, —S$R^{20}$, —N($R^{20}$)$_2$, —N($R^{20}$)C(O)$R^{20}$, —C(O)$R^{20}$, —C(O)O$R^{20}$, —C(O)N($R^{20}$)$_2$, —OC(O)$R^{20}$, —S(O)$_2R^{20}$, —S(O)$_2$N($R^{20}$)$_2$, —N($R^{20}$)S(O)$_2R^{20}$, —NO$_2$, =O, =S, =N($R^{20}$), —P(O)(O$R^{20}$)$_2$, —P(O)($R^{20}$)$_2$, —OP(O)(O$R^{20}$)$_2$, —CN, $C_{1-6}$ alkyl, $C_{2-6}$ alkenyl, and $C_{2-6}$ alkynyl.

In some embodiments of a compound of Formula VII or pharmaceutically acceptable salts thereof, $R^{23}$ is selected from:
hydrogen;
$C_{1-6}$ alkyl optionally substituted with one or more substituents selected from halogen, —O$R^{20}$, —S$R^{20}$, —N($R^{20}$)$_2$, =O, =S, =N($R^{20}$), and —CN; and 3- to 10-membered heterocycle optionally substituted with one or more substituents selected from halogen, —O$R^{20}$, —S$R^{20}$, —N($R^{20}$)$_2$, —N($R^{20}$)C(O)$R^{20}$, —C(O)$R^{20}$, —C(O)O$R^{20}$, —C(O)N($R^{20}$)$_2$, —OC(O)$R^{20}$, —S(O)$_2R^{20}$, —S(O)$_2$N($R^{20}$)$_2$, —N($R^{20}$)S(O)$_2R^{20}$, —NO$_2$, =O, =S, =N($R^{20}$), —P(O)(O$R^{20}$)$_2$, —P(O)($R^{20}$)$_2$, —OP(O)(O$R^{20}$)$_2$, —CN, $C_{1-6}$ alkyl, $C_{2-6}$ alkenyl, and $C_{2-6}$ alkynyl.

In some embodiments of a compound of Formula VII or pharmaceutically acceptable salts thereof, $R^{23}$ is selected from hydrogen and $C_{1-6}$ alkyl optionally substituted with one or more substituents selected from halogen, —O$R^{20}$, —S$R^{20}$, —N($R^{20}$)$_2$, =O, =S, =N($R^{20}$), and —CN.

In some embodiments of a compound of Formula VII or pharmaceutically acceptable salts thereof, $R^{22}$ is selected from:
hydrogen and —CN;
$C_{1-6}$ alkyl, $C_{2-6}$ alkenyl, and $C_{2-6}$ alkynyl, each of which is independently optionally substituted at each occurrence with one or more substituents selected from halogen, —O$R^{20}$, —S$R^{20}$, —N($R^{20}$)$_2$, —N($R^{20}$)C(O)$R^{20}$, —C(O)$R^{20}$, —C(O)O$R^{20}$, —C(O)N($R^{20}$)$_2$, —OC(O)$R^{20}$, —S(O)$_2R^{20}$, —S(O)$_2$N($R^{20}$)$_2$, —N($R^{20}$)S(O)$_2R^{20}$, —NO$_2$, =O, =S, =N($R^{20}$), —P(O)(O$R^{20}$)$_2$, —P(O)($R^{20}$)$_2$, —OP(O)(O$R^{20}$)$_2$, —CN, $C_{3-10}$ carbocycle and 3- to 10-membered heterocycle; and $C_{3-10}$ carbocycle and 3- to 10-membered heterocycle, wherein each $C_{3-10}$ carbocycle and 3- to 10-membered heterocycle is independently optionally substituted with one or more substituents selected from halogen, —O$R^{20}$, —S$R^{20}$, —N($R^{20}$)$_2$, —N($R^{20}$)C(O)$R^{20}$, —C(O)$R^{20}$, —C(O)O$R^{20}$, —C(O)N($R^{20}$)$_2$, —OC(O)$R^{20}$, —S(O)$_2R^{20}$, —S(O)$_2$N($R^{20}$)$_2$, —N($R^{20}$)S(O)$_2R^{20}$, —NO$_2$, =O, =S, =N($R^{20}$), —P(O)(O$R^{20}$)$_2$, —P(O)($R^{20}$)$_2$, —OP(O)(O$R^{20}$)$_2$, —CN, $C_{1-6}$ alkyl, $C_{2-6}$ alkenyl, and $C_{2-6}$ alkynyl.

In some embodiments of a compound of Formula VII or pharmaceutically acceptable salts thereof, $R^{22}$ is selected from hydrogen; —CN; and $C_{1-6}$ alkyl optionally substituted with one or more substituents selected from halogen, —O$R^{20}$, —S$R^{20}$, and —N($R^{20}$)$_2$.

In some embodiments of a compound of Formula VII or pharmaceutically acceptable salts thereof, $R^{22}$ and $R^{23}$, together with the carbon atoms to which they are attached, form a 5-, 6-, or 7-membered carbocyclic ring.

In some embodiments of a compound of Formula VII or pharmaceutically acceptable salts thereof, $R^{24}$ is selected from hydrogen and $C_{1-6}$ alkyl optionally substituted with one or more substituents selected from halogen, —O$R^{20}$, —S$R^{20}$, —N($R^{20}$)$_2$, —NO$_2$, =O, and —CN.

In some embodiments of a compound of Formula VII or pharmaceutically acceptable salts thereof, $R^{21}$ is selected from:

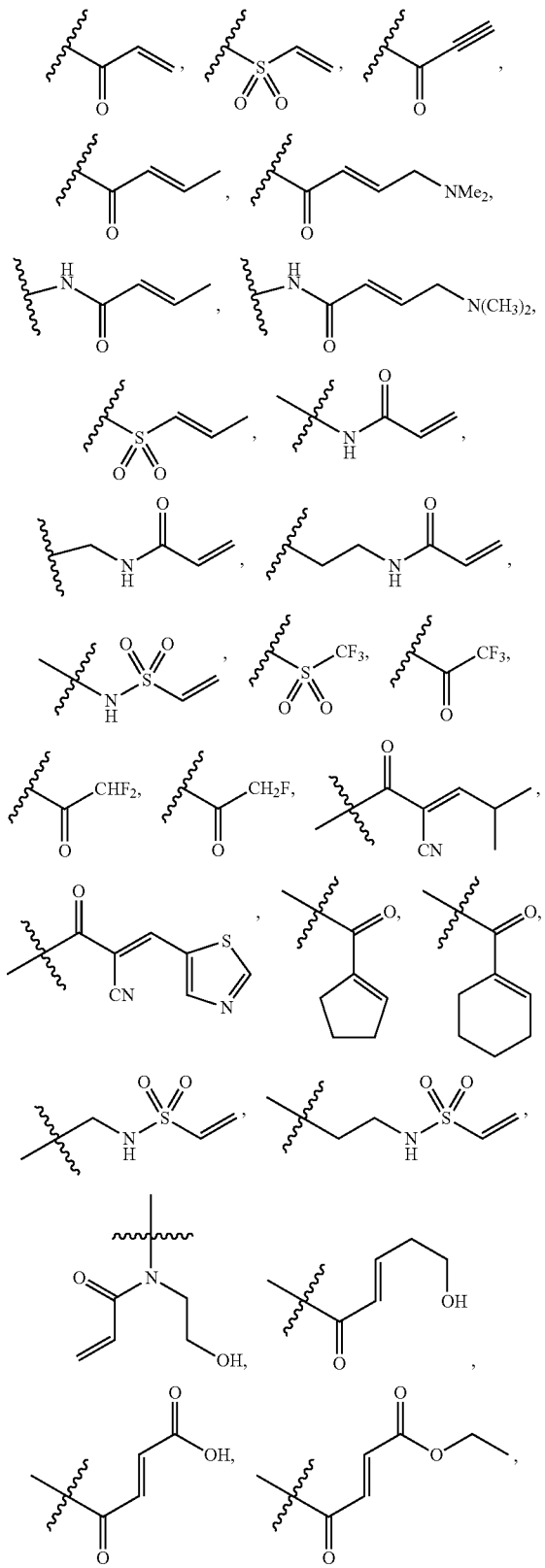

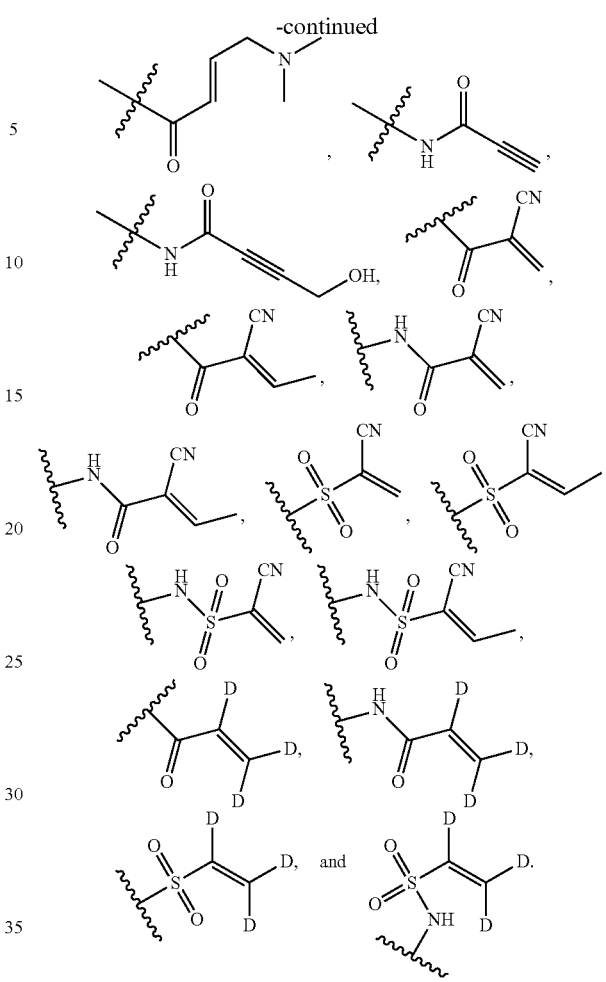

Pharmaceutical Compositions

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of Formula VII or pharmaceutically acceptable salt thereof and a pharmaceutically acceptable carrier.

In some embodiments, the pharmaceutical composition is formulated for oral administration. In other embodiments, the pharmaceutical composition is formulated for injection. In still more embodiments, the pharmaceutical compositions comprise a compound as disclosed herein and an additional therapeutic agent (e.g., anticancer agent). Non-limiting examples of such therapeutic agents are described herein below.

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a composition of a compound of Formula VII or pharmaceutically acceptable salt thereof is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, a compound of Formula VII or pharmaceutically acceptable salt thereof is delivered in a targeted drug delivery system, for example, in a liposome coated with organ-specific antibody. In such embodiments, the liposomes are targeted to and taken up selectively by the organ. In yet other embodiments, the composition is provided in the form of a rapid release formulation, in the form of an extended release formulation, or in the form of an intermediate release formulation. In yet other embodiments, the composition is administered topically.

The compounds of Formula VII or pharmaceutically acceptable salt thereof may be effective over a wide dosage range. For example, in the treatment of adult humans, dosages from 0.01 to 1000 mg per day, from 0.5 to 100 mg per day, from 1 to 50 mg per day, and from 5 to 40 mg per day are examples of dosages that may be used in some embodiments. The exact dosage will depend upon the route of administration, the form in which the compound is administered, the subject to be treated, the body weight of the subject to be treated, and the preference and experience of the attending physician.

In some embodiments, a compound of Formula VII or pharmaceutically acceptable salt thereof is administered in a single dose. Typically, such administration will be by injection, e.g., intravenous injection, in order to introduce the agent quickly. However, other routes are used as appropriate. In some embodiments, a single dose of a compound of Formula VII or pharmaceutically acceptable salt thereof is used for treatment of an acute condition.

In some embodiments, a compound of Formula VII or pharmaceutically acceptable salt thereof is administered in multiple doses. In some embodiments, dosing is about once, twice, three times, four times, five times, six times, or more than six times per day. In other embodiments, dosing is about once a month, once every two weeks, once a week, or once every other day. In another embodiment, a compound of Formula VII or pharmaceutically acceptable salt thereof and another agent are administered together about once per day to about 6 times per day. In another embodiment, the administration of a compound of Formula VII or pharmaceutically acceptable salt thereof and an agent continues for less than about 7 days. In yet another embodiment, the administration continues for more than about 6 days, more than about 10 days, more than about 14 days, more than about 28 days, more than about two months, more than about six months, or one year or more. In some cases, continuous dosing is achieved and maintained as long as necessary.

Administration of the compounds of Formula VII or pharmaceutically acceptable salt thereof may continue as long as necessary. In some embodiments, a compound of the invention is administered for more than 1, more than 2, more than 3, more than 4, more than 5, more than 6, more than 7, more than 14, or more than 28 days. In some embodiments, a compound of the invention is administered 28 days or less, 14 days or less, 7 days or less, 6 days or less, 5 days or less, 4 days or less, 3 days or less, 2 days or less, or 1 day or a part thereof. In some embodiments, a compound of Formula VII or pharmaceutically acceptable salt thereof is administered chronically on an ongoing basis, e.g., for the treatment of chronic effects.

In some embodiments, the compounds of Formula VII or pharmaceutically acceptable salt thereof are administered in dosages. It is known in the art that due to intersubject variability in compound pharmacokinetics, individualization of dosing regimen is necessary for optimal therapy. Dosing for a compound of Formula VII or pharmaceutically acceptable salt thereof may be found by routine experimentation in light of the instant disclosure.

In some embodiments, the compound of Formula VII or pharmaceutically acceptable salt thereof are formulated into pharmaceutical compositions. In specific embodiments, pharmaceutical compositions are formulated in a conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

Provided herein are pharmaceutical compositions comprising a compound of Formula VII or pharmaceutically acceptable salt thereof and a pharmaceutically acceptable diluent(s), excipient(s), or carrier(s). In certain embodiments, the compounds or salts described are administered as pharmaceutical compositions in which a compound of Formula VII or pharmaceutically acceptable salt thereof is mixed with other active ingredients, as in combination therapy. Encompassed herein are all combinations of actives set forth in the combination therapies section below and throughout this disclosure. In specific embodiments, the pharmaceutical compositions include one or more compounds of Formula VII or pharmaceutically acceptable salt thereof.

A pharmaceutical composition, as used herein, refers to a mixture of a compound of Formula VII or pharmaceutically acceptable salt thereof with other chemical components, such as carriers, stabilizers, diluents, dispersing agents, suspending agents, thickening agents, and/or excipients. In certain embodiments, the pharmaceutical composition facilitates administration of the compound to an organism. In some embodiments, practicing the methods of treatment or use provided herein, therapeutically effective amounts of compounds of Formula VII or pharmaceutically acceptable salt thereof are administered in a pharmaceutical composition to a mammal having a disease, disorder or medical condition to be treated. In specific embodiments, the mammal is a human. In certain embodiments, therapeutically effective amounts vary depending on the severity of the disease, the age and relative health of the subject, the potency of the compound used and other factors. The compounds of Formula VII or pharmaceutically acceptable salt thereof are used singly or in combination with one or more therapeutic agents as components of mixtures.

In one embodiment, one or more compounds of Formula VII or pharmaceutically acceptable salt thereof are formulated in an aqueous solution. In specific embodiments, the aqueous solution is selected from, by way of example only, a physiologically compatible buffer, such as Hank's solution, Ringer's solution, or physiological saline buffer. In other embodiments, one or more compounds of Formula VII or pharmaceutically acceptable salt thereof are formulated for transmucosal administration. In specific embodiments, transmucosal formulations include penetrants that are appropriate to the barrier to be permeated. In still other embodiments wherein the compounds of Formula VII or pharmaceutically acceptable salt thereof are formulated for other parenteral injections, appropriate formulations include aqueous or nonaqueous solutions. In specific embodiments, such solutions include physiologically compatible buffers and/or excipients.

In another embodiment, compounds of Formula VII or pharmaceutically acceptable salt thereof are formulated for oral administration. Compounds of Formula VII or pharmaceutically acceptable salt thereof are formulated by combining the active compounds with, e.g., pharmaceutically acceptable carriers or excipients. In various embodiments, the compounds of Formula VII or pharmaceutically acceptable salt thereof are formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipient with one or more of the compounds of Formula VII or pharmaceutically acceptable salt thereof, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

In one embodiment, dosage forms, such as dragee cores and tablets, are provided with one or more suitable coating. In specific embodiments, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, therapeutically effective amounts of at least one of the compounds of Formula VII or pharmaceutically acceptable salt thereof are formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules, contain one or more active compound that is dissolved or suspended in a suitable liquid. Suitable liquids include, by way of example only, one or more fatty oil, liquid paraffin, or liquid polyethylene glycol. In addition, stabilizers are optionally added.

In other embodiments, therapeutically effective amounts of at least one of the compounds of Formula VII or pharmaceutically acceptable salt thereof are formulated for buccal or sublingual administration. Formulations suitable for buccal or sublingual administration include, by way of example only, tablets, lozenges, or gels. In still other embodiments, the compounds of Formula VII or pharmaceutically acceptable salt thereof are formulated for parental injection, including formulations suitable for bolus injection or continuous infusion. In specific embodiments, formulations for injection are presented in unit dosage form (e.g., in ampoules) or in multi-dose containers. Preservatives are, optionally, added to the injection formulations. In still other embodiments, the pharmaceutical compositions are formulated in a form suitable for parenteral injection as sterile suspensions, solutions or emulsions in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active compounds in water-soluble form. In additional embodiments, suspensions of Formula VII or pharmaceutically acceptable salt thereof are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. In certain embodiments, the active agent is in powder form for constitution with a suitable vehicle, e.g., sterile pyrogen-free water, before use.

In still other embodiments, the compounds of Formula VII or pharmaceutically acceptable salt thereof are administered topically. The compounds of Formula VII or pharmaceutically acceptable salt thereof may be formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

In yet other embodiments, the compounds of Formula VII or pharmaceutically acceptable salt thereof are formulated for transdermal administration. Transdermal formulations may employ transdermal delivery devices and transdermal delivery patches and can be lipophilic emulsions or buffered, aqueous solutions, dissolved and/or dispersed in a polymer or an adhesive. In various embodiments, such patches are constructed for continuous, pulsatile, or on demand delivery of pharmaceutical agents. In additional embodiments, the transdermal delivery of the compounds of Formula VII or pharmaceutically acceptable salts thereof is accomplished by means of iontophoretic patches and the like. In certain embodiments, transdermal patches provide controlled delivery of the compounds of Formula VII or pharmaceutically acceptable salt thereof. In specific embodiments, the rate of absorption is slowed by using rate-controlling membranes or by trapping the compound within a polymer matrix or gel. In alternative embodiments, absorption enhancers are used to increase absorption. Absorption enhancers or carriers include absorbable pharmaceutically acceptable solvents that assist passage through the skin. For example, in one embodiment, transdermal devices are in the form of a bandage comprising a backing member, a reservoir containing the compound of Formula VII or pharmaceutically acceptable salt thereof optionally with carriers, optionally a rate controlling barrier to deliver the compound to the skin of the host at a controlled and predetermined rate over a prolonged period of time, and means to secure the device to the skin.

In other embodiments, the compounds of Formula VII or pharmaceutically acceptable salt thereof are formulated for administration by inhalation. Various forms suitable for administration by inhalation include, but are not limited to, aerosols, mists or powders. Pharmaceutical compositions of a compound of Formula VII or pharmaceutically acceptable salt thereof are conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In specific embodiments, the dosage unit of a pressurized aerosol is determined by providing a valve to deliver a metered amount. In certain embodiments, capsules and cartridges of, such as, by way of example only, gelatin for use in an inhaler or insufflator are formulated containing a powder mix of the compound of Formula VII or pharmaceutically acceptable salt thereof and a suitable powder base such as lactose or starch.

In still other embodiments, the compounds of Formula VII or pharmaceutically acceptable salt thereof are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In certain embodiments, pharmaceutical compositions are formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients may be optionally used as suitable. Pharmaceutical compositions comprising a compound of Formula VII or pharmaceutically acceptable salt thereof are manufactured in a conventional manner, such as, by way of example only, by means of conventional mixing, dissolving, granulating, dragee-making, levigating, emulsifying, encapsulating, entrapping or compression processes.

Pharmaceutical compositions include at least one pharmaceutically acceptable carrier, diluent or excipient and at least one compound of Formula VII or pharmaceutically acceptable salt thereof, sometimes referred to herein as an active agent or ingredient. The active ingredient may be in free-acid or free-base form, or in a pharmaceutically acceptable salt form. Additionally, the compounds of Formula VII or pharmaceutically acceptable salt thereof may be in unsolvated or solvated forms with pharmaceutically acceptable solvents such as water and ethanol. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

Methods for the preparation of compositions comprising the compounds of Formula VII or pharmaceutically acceptable salt thereof include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound of Formula VII or pharmaceutically acceptable salt thereof. Semi-solid compositions include, but are not limited to, gels, suspensions and creams. The form of the pharmaceutical compositions of Formula VII or pharmaceutically acceptable salt thereof include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, pharmaceutical composition comprising at least one compound of Formula VII or pharmaceutically acceptable salt thereof illustratively takes the form of a liquid where the agents are present in solution, in suspension or both. Typically when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

In certain embodiments, aqueous suspensions contain one or more polymers as suspending agents. Polymers include water-soluble polymers such as cellulosic polymers, e.g., hydroxypropyl methylcellulose, and water-insoluble polymers such as cross-linked carboxyl-containing polymers. Certain pharmaceutical compositions described herein comprise a mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

Pharmaceutical compositions also, optionally, include solubilizing agents to aid in the solubility of a compound described herein. The term "solubilizing agent" generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, useful compositions also, optionally, include one or more salts in an amount required to bring osmolality of the composition into an acceptable range.

Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Pharmaceutical compositions may include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Pharmaceutical compositions may include one or more antioxidants to enhance chemical stability where required. Suitable antioxidants include, by way of example only, ascorbic acid and sodium metabisulfite.

In certain embodiments, aqueous suspension compositions are packaged in single-dose non-reclosable containers. Alternatively, multiple-dose reclosable containers are used, in which case it is typical to include a preservative in the composition.

In certain embodiments, delivery systems for hydrophobic pharmaceutical compounds are employed. Liposomes and emulsions are examples of delivery vehicles or carriers useful herein. In certain embodiments, organic solvents such as N-methylpyrrolidone are also employed. In additional embodiments, the compounds of Formula VII or pharmaceutically acceptable salt thereof are delivered using a sustained-release system, such as semipermeable matrices of solid hydrophobic polymers containing the therapeutic agent. Various sustained-release materials may be used herein. In some embodiments, sustained-release capsules release the compounds for a few weeks up to over 100 days. Depending on the chemical nature and the biological stability of the therapeutic reagent, additional strategies for protein stabilization are employed.

In certain embodiments, the formulations described herein comprise one or more antioxidants, metal chelating agents, thiol containing compounds and/or other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

In some embodiments, the concentration of one or more compounds of Formula VII or pharmaceutically acceptable salt thereof provided in a pharmaceutical compositions is less than about: 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the concentration of one or more compounds of Formula VII or pharmaceutically acceptable salt thereof provided in a pharmaceutical composition is greater than about: 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 1.25%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the concentration of one or more compounds of Formula VII or pharmaceutically acceptable salt thereof is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the concentration of one or more compounds of Formula VII or pharmaceutically acceptable salt thereof is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of one or more compounds of Formula VII or pharmaceutically acceptable salt thereof is equal to or less than about: 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of one or more compounds of Formula VII or pharmaceutically acceptable salt thereof is more than about: 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

In some embodiments, the amount of one or more compounds of Formula VII or pharmaceutically acceptable salt thereof is in the range of 0.0001-10 g, 0.0005-9 g, 0.001-8 g, 0.005-7 g, 0.01-6 g, 0.05-5 g, 0.1-4 g, 0.5-4 g, or 1-3 g.

Kits/Articles of Manufacture

For use in the therapeutic applications described herein, kits and articles of manufacture are also provided. In some embodiments, such kits comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers are formed from a variety of materials such as glass or plastic.

The articles of manufacture provided herein contain packaging materials. Packaging materials for use in packaging pharmaceutical products include those found in, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. For example, the container(s) includes one or more compounds of Formula VII or pharmaceutically acceptable salt thereof, optionally in a composition or in combination with another agent as disclosed herein. The container(s) optionally have a sterile access port (for example the container is an intravenous solution bag or a vial having a stopper pierceable by a hypodermic injection needle). Such kits optionally comprising a compound with an identifying description or label or instructions relating to its use in the methods described herein.

For example, a kit typically includes one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included. A label is optionally on or associated with the container. For example, a label is on a container when letters, numbers or other characters forming the label are attached, molded or etched into the container itself, a label is associated with a container when it is present within a receptacle or carrier that also holds the container, e.g., as a package insert. In addition, a label is used to indicate that the contents are to be used for a specific therapeutic application. In addition, the label indicates directions for use of the contents, such as in the methods described herein. In certain embodiments, the pharmaceutical composition is presented in a pack or dispenser device which contains one or more unit dosage forms containing a compound provided herein. The pack, for example, contains metal or plastic foil, such as a blister pack. Or, the pack or dispenser device is accompanied by instructions for administration. Or, the pack or dispenser is accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In some embodiments, compositions containing a compound provided herein formulated in a compatible pharmaceutical carrier are prepared, placed in an appropriate container, and labeled for treatment of an indicated condition.

Methods

The present invention provides a method of inhibiting the interaction of menin and one or more proteins (e.g., MLL1, MLL2, a MLL fusion protein, or a MLL Partial Tandem Duplication) comprising contacting a cell with an effective amount of one or more compounds of Formula VII or pharmaceutically acceptable salt thereof. Inhibition of the interaction of menin and one or more proteins (e.g., MLL1, MLL2, a MLL fusion protein, or a MLL Partial Tandem Duplication) can be assessed and demonstrated by a wide variety of ways known in the art. Non-limiting examples include a showing of (a) a decrease in menin binding to one or more proteins or protein fragments (e.g., MLL1, MLL2, a MLL fusion protein, a MLL Partial Tandem Duplication, or a peptide fragment thereof); (b) a decrease in cell proliferation and/or cell viability; (c) an increase in cell differentiation; (d) a decrease in the levels of downstream targets of MLL1, MLL2, a MLL fusion protein, and/or a MLL Partial Tandem Duplication (e.g., Hoxa9, DLX2, and Meis1); and/or (e) decrease in tumor volume and/or tumor volume growth rate. Kits and commercially available assays can be utilized for determining one or more of the above.

The invention also provides methods of using the compounds or pharmaceutical compositions of the present invention to treat disease conditions, including but not limited to conditions implicated by menin, MLL, MLL1, MLL2, and/or MLL fusion proteins (e.g., cancer).

In some embodiments, a method for treatment of cancer is provided, the method comprising administering an effective amount of any of the foregoing pharmaceutical compositions comprising a compound of Formula VII or pharmaceutically acceptable salt thereof to a subject in need thereof. In some embodiments, the cancer is mediated by a MLL fusion protein. In other embodiments, the cancer is leukemia, breast cancer, prostate cancer, pancreatic cancer, lung cancer, liver cancer, skin cancer, or a brain tumor. In certain embodiments, the cancer is leukemia.

In some embodiments the invention provides method of treating a disorder in a subject in need thereof, wherein the method comprises determining if the subject has a MLL fusion protein and if the subject is determined to have a MLL fusion protein, then administering to the subject a therapeutically effective dose of at least one compound of Formula VII or a pharmaceutically acceptable salt, ester, or prodrug thereof.

MLL fusion proteins have also been identified in hematological malignancies (e.g., cancers that affect blood, bone marrow and/or lymph nodes). Accordingly, certain embodiments are directed to administration of a compound of Formula VII to a patient in need of treatment of a hematological malignancy. Such malignancies include, but are not limited to leukemias and lymphomas. For example, the presently disclosed compounds can be used for treatment of diseases such as Acute lymphoblastic leukemia (ALL), Acute myelogenous leukemia (AML), Chronic lymphocytic leukemia (CLL), small lymphocytic lymphoma (SLL), Chronic myelogenous leukemia (CML), Acute monocytic leukemia (AMoL), hairy cell leukemia, and/or other leukemias. In other embodiments, the compounds can be used for treatment of lymphomas such as all subtypes of Hodgkins lymphoma or non-Hodgkins lymphoma.

Determining whether a tumor or cancer comprises a MLL fusion protein can be undertaken by assessing the nucleotide sequence encoding the MLL fusion protein, by assessing the amino acid sequence of the MLL fusion protein, or by assessing the characteristics of a putative MLL fusion protein.

Methods for detecting a MLL fusion protein nucleotide sequence are known by those of skill in the art. These methods include, but are not limited to, polymerase chain reaction-restriction fragment length polymorphism (PCR-RFLP) assays, polymerase chain reaction-single strand conformation polymorphism (PCR-SSCP) assays, real-time PCR assays, PCR sequencing, mutant allele-specific PCR amplification (MASA) assays, direct sequencing, primer extension reactions, electrophoresis, oligonucleotide ligation assays, hybridization assays, TaqMan assays, SNP genotyping assays, high resolution melting assays and microarray analyses. In some embodiments, the MLL fusion protein is identified using a direct sequencing method of specific regions (e.g., exon 2 and/or exon 3) in the MLL or fusion partner gene, for example. This technique will identify all possible mutations in the region sequenced.

Methods for detecting a MLL fusion protein are known by those of skill in the art. These methods include, but are not limited to, detection of a MLL fusion protein using a binding agent (e.g., an antibody) specific for the fusion protein, protein electrophoresis and Western blotting, and direct peptide sequencing.

Methods for determining whether a tumor or cancer comprises a MLL fusion protein can use a variety of samples. In some embodiments, the sample is taken from a subject having a tumor or cancer. In some embodiments, the sample is taken from a subject having a cancer or tumor. In some embodiments, the sample is a fresh tumor/cancer sample. In some embodiments, the sample is a frozen tumor/cancer sample. In some embodiments, the sample is a formalin-fixed paraffin-embedded sample. In some embodiments, the sample is processed to a cell lysate. In some embodiments, the sample is processed to DNA or RNA.

The invention also relates to a method of treating a hyperproliferative disorder in a mammal that comprises administering to the mammal a therapeutically effective amount of a compound of Formula VII or a pharmaceutically acceptable salt, ester, or prodrug thereof. In some embodiments, the method relates to the treatment of cancer such as acute myeloid leukemia, cancer in adolescents, adrenocortical carcinoma childhood, AIDS-related cancers (e.g., Lymphoma and Kaposi's Sarcoma), anal cancer, appendix cancer, astrocytomas, atypical teratoid, basal cell carcinoma, bile duct cancer, bladder cancer, bone cancer, brain stem glioma, brain tumor, breast cancer, bronchial tumors, burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myeloproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, hodgkin lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer multiple endocrine neoplasia syndromes, multiple myeloma/plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-hodgkin lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or Viral-Induced cancer. In some embodiments, the method relates to the treatment of a non-cancerous hyperproliferative disorder such as benign hyperplasia of the skin (e.g., psoriasis), restenosis, or prostate (e.g., benign prostatic hypertrophy (BPH)). In some cases, the method relates to the treatment of leukemia, hematologic malignancy, solid tumor cancer, prostate cancer (e.g., castration-resistant prostate cancer), breast cancer, Ewing's sarcoma, bone sarcoma, primary bone sarcoma, T-cell prolymphocyte leukemia, glioma, glioblastoma, liver cancer (e.g., hepatocellular carcinoma), or diabetes. In some cases, the leukemia comprises AML, ALL, Mixed Lineage Leukemia or leukemias with Partial Tandem Duplications of MLL.

In certain particular embodiments, the invention relates to methods for treatment of lung cancers, the methods comprise administering an effective amount of any of the above described compound (or a pharmaceutical composition comprising the same) to a subject in need thereof. In certain embodiments the lung cancer is a non-small cell lung carcinoma (NSCLC), for example adenocarcinoma, squamous-cell lung carcinoma or large-cell lung carcinoma. In other embodiments, the lung cancer is a small cell lung carcinoma. Other lung cancers treatable with the disclosed compounds include, but are not limited to, glandular tumors, carcinoid tumors and undifferentiated carcinomas.

Subjects that can be treated with compounds of the invention, or pharmaceutically acceptable salt, ester, prodrug, solvate, tautomer, stereoisomer, isotopologue, hydrate or derivative of the compounds, according to the methods of this invention include, for example, subjects that have been diagnosed as having acute myeloid leukemia, acute myeloid leukemia, cancer in adolescents, adrenocortical carcinoma childhood, AIDS-related cancers (e.g., Lymphoma and Kaposi's Sarcoma), anal cancer, appendix cancer, astrocytomas, atypical teratoid, basal cell carcinoma, bile duct cancer, bladder cancer, bone cancer, brain stem glioma, brain tumor, breast cancer, bronchial tumors, burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myleoproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, hodgkin lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer multiple endocrine neoplasia syndromes, multiple myeloma/plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-hodgkin lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, Viral-Induced cancer, leukemia, hematologic malignancy, solid tumor cancer, prostate cancer, castration-resistant prostate cancer, breast cancer, Ewing's sarcoma, bone sarcoma, primary bone sarcoma, T-cell prolymphocyte leukemia, glioma, glioblastoma, hepatocellular carcinoma, liver cancer, or diabetes. In some embodiments subjects that are treated with the compounds of the invention include subjects that have been diagnosed as having a non-cancerous hyperproliferative disorder such as benign hyperplasia of the skin (e.g., psoriasis), restenosis, or prostate (e.g., benign prostatic hypertrophy (BPH)).

The invention further provides methods of modulating the interaction of menin and one or more proteins (e.g., MLL1, MLL2, a MLL fusion protein, or a MLL Partial Tandem Duplication) by contacting the menin with an effective amount of a compound of Formula VII or pharmaceutically acceptable salt thereof. Modulation can be inhibiting or activating protein activity of menin, one or more of its binding partners, and/or one or more of the downstream targets of menin or one or more of its binding partners. In some embodiments, the invention provides methods of inhibiting the interaction of menin and one or more proteins (e.g., MLL1, MLL2, a MLL fusion protein, or a MLL Partial Tandem Duplication) by contacting menin with an effective amount of a compound of Formula VII or pharmaceutically acceptable salt thereof. In some embodiments, the invention provides methods of inhibiting the interaction of menin and one or more proteins (e.g., MLL1, MLL2, a MLL fusion protein, or a MLL Partial Tandem Duplication) by contacting a cell, tissue, or organ that expresses menin, MLL1, MLL2, a MLL fusion protein, and/or a MLL Partial Tandem Duplication. In some embodiments, the invention provides methods of inhibiting protein activity in subject including but not limited to rodents and mammal (e.g., human) by administering into the subject an effective amount of a compound of Formula VII or pharmaceutically acceptable salt thereof. In some embodiments, the percentage modulation exceeds 25%, 30%, 40%, 50%, 60%, 70%, 80%, or 90%. In some embodiments, the percentage of inhibiting exceeds 25%, 30%, 40%, 50%, 60%, 70%, 80%, or 90%.

In some embodiments, the invention provides methods of inhibiting the interaction of menin and one or more proteins (e.g., MLL1, MLL2, a MLL fusion protein, or a MLL Partial Tandem Duplication) in a cell by contacting the cell with an amount of a compound of the invention sufficient to inhibit the interaction of menin and one or more proteins (e.g., MLL1, MLL2, a MLL fusion protein, or a MLL Partial Tandem Duplication) in the cell. In some embodiments, the invention provides methods of inhibiting the interaction of menin and one or more proteins (e.g., MLL1, MLL2, a MLL fusion protein, or a MLL Partial Tandem Duplication) in a tissue by contacting the tissue with an amount of a compound of Formula VII or pharmaceutically acceptable salt thereof sufficient to inhibit the interaction of menin and one or more proteins (e.g., MLL1, MLL2, a MLL fusion protein, or a MLL Partial Tandem Duplication) in the tissue. In some embodiments, the invention provides methods of inhibiting the interaction of menin and one or more proteins (e.g., MLL1, MLL2, a MLL fusion protein, or a MLL Partial Tandem Duplication) in an organism by contacting the organism with an amount of a compound of Formula VII or pharmaceutically acceptable salt thereof sufficient to inhibit the interaction of menin and one or more proteins (e.g., MLL1, MLL2, a MLL fusion protein, or a MLL Partial Tandem Duplication) in the organism. In some embodiments, the invention provides methods of inhibiting the interaction of menin and one or more proteins (e.g., MLL1, MLL2, a MLL fusion protein, or a MLL Partial Tandem Duplication) in an animal by contacting the animal with an amount of a compound of the invention sufficient to inhibit the interaction of menin and one or more proteins (e.g., MLL1, MLL2, a MLL fusion protein, or a MLL Partial Tandem Duplication) in the animal. In some embodiments, the invention provides methods of inhibiting the interaction of menin and one or more proteins (e.g., MLL1, MLL2, a MLL fusion protein, or a MLL Partial Tandem Duplication) in a mammal by contacting the mammal with an amount of a compound of the invention sufficient to inhibit the interaction of menin and one or more proteins (e.g., MLL1, MLL2, a MLL fusion protein, or a MLL Partial Tandem Duplication) in the mammal. In some embodiments, the invention provides methods of inhibiting the interaction of menin and one or more proteins (e.g., MLL1, MLL2, a MLL fusion protein, or a MLL Partial Tandem Duplication) in a human by contacting the human with an amount of a compound of the invention sufficient to inhibit the interaction of menin and one or more proteins (e.g., MLL1, MLL2, a MLL fusion protein, or a MLL Partial Tandem Duplication) in the human. The present invention provides methods of treating a disease mediated by the interaction of menin and one or more proteins (e.g., MLL1, MLL2, a MLL fusion protein, or a MLL Partial Tandem Duplication) in a subject in need of such treatment.

The invention further provides methods of stabilizing menin, comprising contacting menin with a compound of Formula VII or pharmaceutically acceptable salts thereof. In some embodiments, the contacting step comprises contacting menin with an amount of the compound sufficient to stabilize menin. In some embodiments, the contacting step takes place in vivo. In some embodiments, the contacting step takes place in vitro. In some embodiments, the contacting step takes place in a cell.

The invention also provides methods of treating a disorder mediated by menin interaction with one or more proteins (e.g., MLL1, MLL2, a MLL fusion protein, or a MLL Partial Tandem Duplication) by administering to a subject in need thereof a therapeutically effective amount of a compound of Formula VII or pharmaceutically acceptable salt thereof.

The invention further provides methods of treating a disorder mediated by chromosomal rearrangement on chromosome 11 q23 in a subject in need thereof by administering to the subject a therapeutically effective amount of a compound of Formula VII or pharmaceutically acceptable salt thereof.

The invention also provides methods for the treatment of a disease or condition by administering an effective amount of a compound of Formula VII or pharmaceutically acceptable salt thereof to a subject suffering from the disease or condition.

The invention further provides methods for the treatment of a disease or condition by administering a compound of Formula VII or pharmaceutically acceptable salt thereof to a subject suffering from the disease or condition, wherein the compound binds to menin and inhibits the interaction of menin with one or more proteins (e.g., MLL1, MLL2, a MLL fusion protein, or a MLL Partial Tandem Duplication).

The present invention also provides methods for combination therapies in which an agent known to modulate other pathways, or other components of the same pathway, or even overlapping sets of target enzymes are used in combination with a compound of Formula VII or pharmaceutically acceptable salt thereof. In one aspect, such therapy includes but is not limited to the combination of one or more compounds of the invention with chemotherapeutic agents, therapeutic antibodies, and radiation treatment, to provide a synergistic or additive therapeutic effect.

Where desired, the compounds or pharmaceutical composition of the present invention can be used in combination with Notch inhibitors and/or c-Myb inhibitors. Where desired, the compounds or pharmaceutical composition of the present invention can be used in combination with MLL-WDR5 inhibitors and/or Dot11 inhibitors.

Many chemotherapeutics are presently known in the art and can be used in combination with the compounds of the invention. In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

Non-limiting examples are chemotherapeutic agents, cytotoxic agents, and non-peptide small molecules such as Gleevec® (Imatinib Mesylate), Velcade® (bortezomib), Casodex (bicalutamide), Iressa® (gefitinib), and Adriamycin as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, tri ethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g., paclitaxel (TAXOL™, Bristol-Myers Squibb Oncology, Princeton, N.J.) and docetaxel (TAXOTERE™, Rhone-Poulenc Rorer, Antony, France); retinoic acid; esperamicins; capecitabine; and pharmaceutically acceptable salts, acids or derivatives of any of the above. Also included as suitable chemotherapeutic cell conditioners are anti-hormonal agents that act to regulate or inhibit hormone action on tumors such as anti-estrogens including for example tamoxifen, (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomerase inhibitor RFS 2000; difluoromethylornithine (DMFO). Where desired, the compounds or pharmaceutical composition of the present invention can be used in combination with commonly prescribed anti-cancer drugs such as Herceptin®, Avastin®, Erbitux®, Rituxan®, Taxol®, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl)amine, Troxacitabine, Uramustine, Vadimezan, Vinflunine, ZD6126 or Zosuquidar.

This invention further relates to a method for using the compounds of Formula VII or pharmaceutically acceptable salt thereof or pharmaceutical compositions provided herein, in combination with radiation therapy for inhibiting abnormal cell growth or treating the hyperproliferative disorder in the mammal. Techniques for administering radiation therapy are known in the art, and these techniques can be used in the combination therapy described herein. The administration of the compound of the invention in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g., At-211, I-131, I-125, Y-90, Re-186, Re-188, Sm-153, Bi-212, P-32, and radioactive isotopes of Lu). Suitable radiation sources for use as a cell conditioner of the present invention include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

The compounds or pharmaceutical compositions of the invention can be used in combination with an amount of one or more substances selected from anti-angiogenesis agents, signal transduction inhibitors, antiproliferative agents, glycolysis inhibitors, or autophagy inhibitors.

Anti-angiogenesis agents, such as MMP-2 (matrix-metalloproteinase 2) inhibitors, MMP-9 (matrix-metalloproteinase 9) inhibitors, and COX-11 (cyclooxygenase 11) inhibitors, can be used in conjunction with a compound of the invention and pharmaceutical compositions described herein. Anti-angiogenesis agents include, for example, rapamycin, temsirolimus (CCI-779), everolimus (RAD001), sorafenib, sunitinib, and bevacizumab. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931, 788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or AMP-9 relative to the other matrix-metalloproteinases (e.g., MAP-1, MMP-3, MMP-4, MMP-5, MMP-6, MMP-7, MMP-8, MMP-10, MMP-11, MMP-12, and MMP-13). Some specific examples of MMP inhibitors useful in the invention are AG-3340, RO 32-3555, and RS 13-0830.

Autophagy inhibitors include, but are not limited to chloroquine, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNA that inhibits expression of proteins including but not limited to ATG5 (which are implicated in autophagy), may also be used.

In some embodiments, the compounds described herein are formulated or administered in conjunction with liquid or solid tissue barriers also known as lubricants. Examples of tissue barriers include, but are not limited to, polysaccharides, polyglycans, seprafilm, interceed and hyaluronic acid.

In some embodiments, medicaments which are administered in conjunction with the compounds described herein include any suitable drugs usefully delivered by inhalation for example, analgesics, e.g., codeine, dihydromorphine, ergotamine, fentanyl or morphine; anginal preparations, e.g., diltiazem; antiallergics, e.g., cromoglycate, ketotifen or nedocromil; anti-infectives, e.g., cephalosporins, penicillins, streptomycin, sulphonamides, tetracyclines or pentamidine; antihistamines, e.g., methapyrilene; anti-inflammatories, e.g., beclomethasone, flunisolide, budesonide, tipredane, triamcinolone acetonide or fluticasone; antitussives, e.g., noscapine; bronchodilators, e.g., ephedrine, adrenaline, fenoterol, formoterol, isoprenaline, metaproterenol, phenylephrine, phenylpropanolamine, pirbuterol, reproterol, rimiterol, salbutamol, salmeterol, terbutalin, isoetharine, tulobuterol, orciprenaline or (−)-4-amino-3,5-dichloro-α-[[[6-[2-(2-pyridinyl)ethoxy]hexyl]-amino]methyl]benzenemethanol; diuretics, e.g., amiloride; anticholinergics e.g., ipratropium, atropine or oxitropium; hormones, e.g., cortisone, hydrocortisone or prednisolone; xanthines e.g., aminophylline, choline theophyllinate, lysine theophyllinate or theophylline; and therapeutic proteins and peptides, e.g., insulin or glucagon. It will be clear to a person skilled in the art that, where appropriate, the medicaments are used in the form of salts (e.g., as alkali metal or amine salts or as acid addition salts) or as esters (e.g., lower alkyl esters) or as solvates (e.g., hydrates) to optimize the activity and/or stability of the medicament.

Other exemplary therapeutic agents useful for a combination therapy include but are not limited to agents as described above, radiation therapy, hormone antagonists, hormones and their releasing factors, thyroid and antithyroid drugs, estrogens and progestins, androgens, adrenocorticotropic hormone; adrenocortical steroids and their synthetic analogs; inhibitors of the synthesis and actions of adrenocortical hormones, insulin, oral hypoglycemic agents, and the pharmacology of the endocrine pancreas, agents affecting calcification and bone turnover: calcium, phosphate, parathyroid hormone, vitamin D, calcitonin, vitamins such as water-soluble vitamins, vitamin B complex, ascorbic acid, fat-soluble vitamins, vitamins A, K, and E, growth factors, cytokines, chemokines, muscarinic receptor agonists and antagonists; anticholinesterase agents; agents acting at the neuromuscular junction and/or autonomic ganglia; catecholamines, sympathomimetic drugs, and adrenergic receptor agonists or antagonists; and 5-hydroxytryptamine (5-HT, serotonin) receptor agonists and antagonists.

Therapeutic agents can also include agents for pain and inflammation such as histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in humoral and cellular immune responses, lipid-derived autacoids, eicosanoids, β-adrenergic agonists, ipratropium, glucocorticoids, methylxanthines, sodium channel blockers, opioid receptor agonists, calcium channel blockers, membrane stabilizers and leukotriene inhibitors.

Additional therapeutic agents contemplated herein include diuretics, vasopressin, agents affecting the renal conservation of water, rennin, angiotensin, agents useful in the treatment of myocardial ischemia, anti-hypertensive agents, angiotensin converting enzyme inhibitors, β-adrenergic receptor antagonists, agents for the treatment of hypercholesterolemia, and agents for the treatment of dyslipidemia.

Other therapeutic agents contemplated include drugs used for control of gastric acidity, agents for the treatment of peptic ulcers, agents for the treatment of gastroesophageal reflux disease, prokinetic agents, antiemetics, agents used in irritable bowel syndrome, agents used for diarrhea, agents used for constipation, agents used for inflammatory bowel disease, agents used for biliary disease, agents used for pancreatic disease. Therapeutic agents used to treat protozoan infections, drugs used to treat Malaria, Amebiasis, Giardiasis, Trichomoniasis, Trypanosomiasis, and/or Leishmaniasis, and/or drugs used in the chemotherapy of helminthiasis. Other therapeutic agents include antimicrobial agents, sulfonamides, trimethoprim-sulfamethoxazole quinolones, and agents for urinary tract infections, penicillins, cephalosporins, and other, β-lactam antibiotics, an agent comprising an aminoglycoside, protein synthesis inhibitors, drugs used in the chemotherapy of tuberculosis, *Mycobacterium avium* complex disease, and leprosy, antifungal agents, antiviral agents including nonretroviral agents and antiretroviral agents.

Examples of therapeutic antibodies that can be combined with a compound of the invention include but are not limited to anti-receptor tyrosine kinase antibodies (cetuximab, panitumumab, trastuzumab), anti CD20 antibodies (rituximab, tositumomab), and other antibodies such as alemtuzumab, bevacizumab, and gemtuzumab.

Moreover, therapeutic agents used for immunomodulation, such as immunomodulators, immunosuppressive agents, tolerogens, and immunostimulants are contemplated by the methods herein. In addition, therapeutic agents acting on the blood and the blood-forming organs, hematopoietic agents, growth factors, minerals, and vitamins, anticoagulant, thrombolytic, and antiplatelet drugs.

For treating renal carcinoma, one may combine a compound of the present invention with sorafenib and/or avastin. For treating an endometrial disorder, one may combine a compound of the present invention with doxorubincin, taxotere (taxol), and/or cisplatin (carboplatin). For treating ovarian cancer, one may combine a compound of the present invention with cisplatin (carboplatin), taxotere, doxorubincin, topotecan, and/or tamoxifen. For treating breast cancer, one may combine a compound of the present invention with taxotere (taxol), gemcitabine (capecitabine), tamoxifen, letrozole, tarceva, lapatinib, PD0325901, avastin, herceptin, OSI-906, and/or OSI-930. For treating lung cancer, one may combine a compound of the present invention with taxotere (taxol), gemcitabine, cisplatin, pemetrexed, Tarceva, PD0325901, and/or avastin.

Further therapeutic agents that can be combined with a compound of the invention are found in Goodman and Gilman's "The Pharmacological Basis of Therapeutics" Tenth Edition edited by Hardman, Limbird and Gilman or the Physician's Desk Reference, both of which are incorporated herein by reference in their entirety.

The compounds described herein can be used in combination with the agents disclosed herein or other suitable agents, depending on the condition being treated. Hence, in some embodiments the one or more compounds of the invention will be co-administered with other agents as described above. When used in combination therapy, the compounds described herein are administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound of the invention and any of the agents described above can be simultaneously administered, wherein both the agents are present in separate formulations. In another alternative, a compound of the present invention can be administered just followed by and any of the agents described above, or vice versa. In some embodiments of the separate administration protocol, a compound of the invention and any of the agents described above are administered a few minutes apart, or a few hours apart, or a few days apart.

The examples and preparations provided below further illustrate and exemplify the compounds of the present invention and methods of preparing such compounds. It is to be understood that the scope of the present invention is not limited in any way by the scope of the following examples and preparations. In the following examples, and throughout the specification and claims, molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

EXAMPLES

Non-Limiting Examples of Compound Synthesis
Synthesis of a Compound of Formula VII

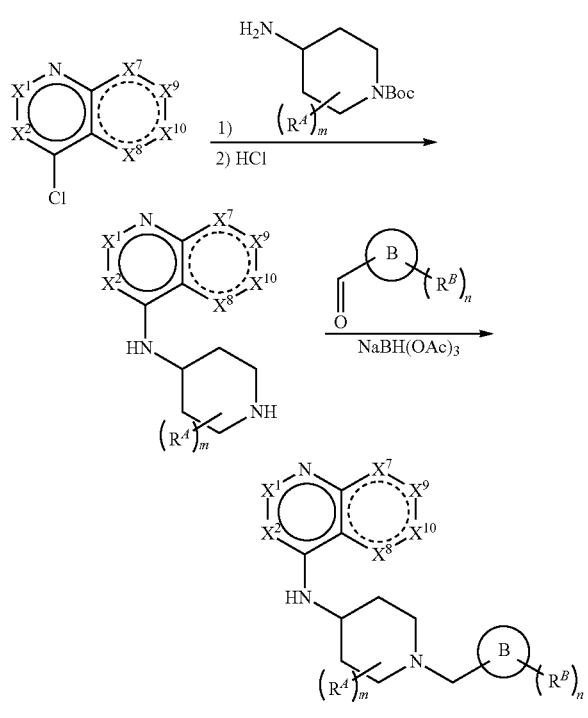

Synthesis of a Compound of Formula VII, Compound VII-7

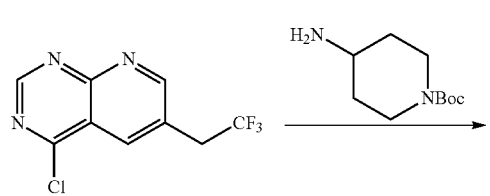

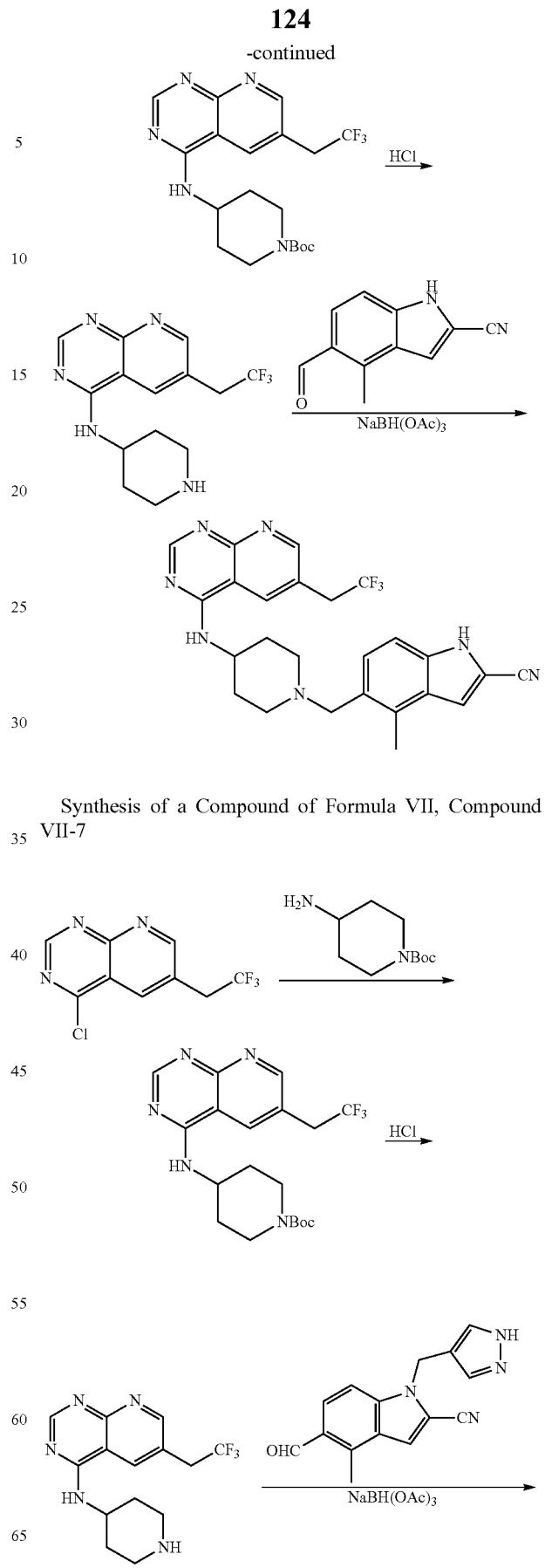

Synthesis of a Compound of Formula VII, Compound VII-7

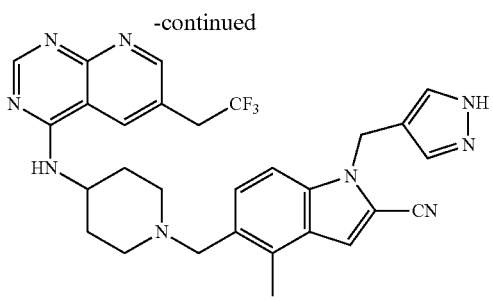

Non-Limiting Examples of Experimental Assays

Fluorescence Polarization Assay.

This example illustrates an assay effective in monitoring the binding of MLL to menin. Fluorescence polarization (FP) competition experiments are performed to determine the effectiveness with which a compound inhibits the menin-MLL interaction, reported as an $IC_{50}$ value. A fluorescein-labeled 12-amino acid peptide containing the high affinity menin binding motif found in MLL is produced according to Yokoyama et al. (*Cell*, 2005, 123(2): 207-218), herein incorporated by reference in its entirety. Binding of the labeled peptide (1.7 kDa) to the much larger menin (~67 kDa) is accompanied by a significant change in the rotational correlation time of the fluorophore, resulting in a substantial increase in the fluorescence polarization and fluorescence anisotropy (excitation at 500 nm, emission at 525 nm). The effectiveness with which a compound inhibits the menin-MLL interaction is measured in an FP competition experiment, wherein a decrease in fluorescence anisotropy correlates with inhibition of the interaction and is used as a read-out for $IC_{50}$ determination.

Homogeneous Time-Resolve Fluorescence (HTRF) Assay.

A homogeneous time-resolve fluorescence (HTRF) assay is utilized as a secondary assay to confirm the results of the FP assay. In some embodiments, the HTRF assay is the primary assay and the FP assay is used as a secondary assay to confirm results. HTRF is based on the non-radiative energy transfer of the long-lived emission from the Europium cryptate ($Eu^{3+}$-cryptate) donor to the allophycocyanin (XL665) acceptor, combined with time-resolved detection. An $Eu^{3+}$-cryptate donor is conjugated with mouse anti-6His monoclonal antibody (which binds His-tagged menin) and XL665-acceptor is conjugate to streptavidin (which binds biotinylated MLL peptide). When these two fluorophores are brought together by the interaction of menin with the MLL peptide, energy transfer to the acceptor results in an increase in fluorescence emission at 665 nm and increased HTRF ratio (emission intensity at 665 nm/emission intensity at 620 nm). Inhibition of the menin-MLL interaction separates the donor from the acceptor, resulting in a decrease in emission at 665 nm and decreased HTRF ratio.

Menin Engagement Assay.

Sample Preparation: 2.5 µL of 100 µM compound is added to 47.5 µL of 526 nM menin in PBS (5 M compound 500 nM menin in 5% DMSO final concentration). Reaction is incubated at room temperature for variable lengths of time and quenched with 2.5 µL of 4% formic acid (FA, 0.2% final concentration). Method: A Thermo Finnigan Surveyor Autosampler, PDA Plus UV detector and MS Pump along with an LTQ linear ion trap mass spectrometer are used to collect sample data under XCalibur software control. A 5 µL sample in "no waste" mode is injected onto a Phenomenex Jupiter 5u 300A C5 (guard column) 2×4.00 mm at 45° C. Mobile phase composition: Buffer A (95:5 water:acetonitrile, 0.1% FA) and Buffer B (acetonitrile, 0.1% FA). Gradient elution is used with an initial mobile phase of 85:15 (Buffer A:B) and a flow rate of 250 µL/min. Upon injection, 85:15 A:B is held for 1.3 min, Buffer B is increased to 90% over 3.2 min, held for 1 min, and then returned to initial conditions in 0.1 min and held for 2.4 min. The total run time is 8 min. A post-column divert valve employed to direct void volume salts to waste is used for the first 2 min of the sample method. Blank injection of Buffer A is used in between each of the sample injections. A needle wash of 1:1 acetonitrile:water with 0.1% FA is used. The electrospray ionization (ESI) source uses a 300° C. capillary temperature, 40 units sheath gas flow, 20 units aux gas flow, 3 units sweep gas flow, 3.5 kV spray voltage, and 120 V tube lens. Data Collection: Data collection is performed in the positive ion full scan mode 550-1500 Da, 10 microscans, 200 ms max ion time. Data analysis: Protein mass spectra are acquired as XCalibur datafiles. The best scans are added together using XCalibur Qual Browser. The spectra are displayed using "View/Spectrum List with a Display option to display all peaks. The Edit/Copy cell menu is used to copy the mass spectrum into the PC clipboard. The spectrum in the PC clipboard is pasted into Excel. The first two columns (m/z and Intensity are kept and the third column (Relative) is deleted. The remaining two columns are then saved as a tab delimited file (m/z and intensity) as filename.txt from Excel. The Masslynx Databridge program is then used to convert the filename.txt tab delimited file to Masslynx format. In some cases, an external calibration using a (similarly converted) myoglobin spectrum is applied in Masslynx to correct the m/z values of the menin protein m/z data. MaxEnt1 software from the MassLynx software suite is used for deconvolution of the mass spectrum to yield the average MW of the protein(s). The percentage of covalent adduct formation is determined from the deconvoluted spectrum and used to calculate the reaction rate (k) of the covalent reaction.

Cell Proliferation Assay.

The ability of a compound of the present invention to inhibit the growth of cells, such as human leukemia, VCaP, LNCaP, 22RV1, DU145, LNCaP-AR, MV4;11, KOPN-8, ML-2, MOLM-13, bone marrow cells (BMCs), MLL-AF9, MLL-ENL, MLL-CBP, MLL-GAS7, MLL-AF1p, MLL-AF6, HM-2, E2A-HLF, HL-60 and NB4 cells, is tested using a cell viability assay, such as the Promega CellTiter-Glo® Luminescent Cell Viability Assay (Promega Technical Bulletin, 2015, "CellTiter-Glo® Luminescent Cell Viability Assay": 1-15, herein incorporated by reference in its entirety). Cells are plated at relevant concentrations, for example about $1 \times 10^5 - 2 \times 10^5$ cells per well in a 96-well plate. A compound of the present invention is added at a concentration up to about 2 µM with eight, 2-fold serial dilutions for each compound. Cells are incubated at 37° C. for a period of time, for example, 72 hours, then cells in the control wells are counted. Media is changed to restore viable cell numbers to the original concentration, and compounds are re-supplied. Proliferation is measured about 72 hours later using Promega CellTiter-Glo® reagents, as per kit instructions.

RT-PCR Analysis of MLL Fusion Protein Downstream Targets.

The effect of a compound of the present invention on expression of one or more MLL fusion protein downstream targets is assessed by RT-PCR. Cells, such as VCaP, LNCaP, 22RV1, DU145, LNCaP-AR, MV4;11, KOPN-8, ML-2, MOLM-13, bone marrow cells (BMCs), MLL-AF9, MLL-ENL, MLL-CBP, MLL-GAS7, MLL-AF1p, MLL-AF6, HM-2, E2A-HLF, HL-60 and NB4 cells, are treated with an effective concentration of a compound for about 7 days or less, then total RNA is extracted from cells using an RNeasy mini kit (QIAGEN). Total RNA is reverse transcribed using a High Capacity cDNA Reverse Transcription Kit (Applied Biosystems), and relative quantification of relevant gene transcripts (e.g., Hoxa9, DLX2, and Meis1) is determined by real-time PCR. Effective inhibition of the menin-MLL interaction is expected to result in the downregulation of downstream targets of MLL, including Hoxa9, DLX2, and Meis1.

Pharmacokinetic Studies in Mice.

The pharmacokinetics of menin-MLL inhibitors are determined in female C57BL/6 mice following intravenous (iv) dosing at 15 mg/kg and oral dosing (po) at 30 mg/kg. Compounds are dissolved in the vehicle containing 25% (v/v) DMSO, 25% (v/v) PEG-400 and 50% (v/v) PBS. Serial blood samples (50 μL) are collected over 24 h, centrifuged at 15,000 rpm for 10 min and saved for analysis. Plasma concentrations of the compounds are determined by the LC-MS/MS method developed and validated for this study. The LC-MS/MS method consists of an Agilent 1200 HPLC system and chromatographic separation of tested compound is achieved using an Agilent Zorbax Extend-C18 column (5 cm×2.1 mm, 3.5 m; Waters). An AB Sciex QTrap 3200 mass spectrometer equipped with an electrospray ionization source (ABI-Sciex, Toronto, Canada) in the positive-ion multiple reaction monitoring (MRM) mode is used for detection. All pharmacokinetic parameters are calculated by noncompartmental methods using WinNonlin® version 3.2 (Pharsight Corporation, Mountain View, Calif., USA).

Efficacy Study in Mouse Xenograft Tumor Model.

Immunodeficient mice, such as 8-10 week-old female nude (nu/nu) mice, are used for in vivo efficacy studies in accordance with the guidelines approved by IACUC. Leukemia cells, such as human MV4-11 leukemia cells available from ATCC, are implanted subcutaneously via needle into female nude mice ($5 \times 10^6$ cells/mouse). When the tumor reaches a size of approximately 150 to 250 mm$^3$ in mice, the tumor-bearing mice are randomly assigned to a vehicle control or compound treatment group (8 animals per group). Animals are treated with a compound of the present invention by oral gavage or intraperitoneal injection in an appropriate amount and frequency as can be determined by the skilled artisan without undue experimentation. Subcutaneous tumor volume in nude mice and mice body weight are measured twice weekly. Tumor volumes are calculated by measuring two perpendicular diameters with calipers (V=(length×width$^2$)/2). Percentage tumor growth inhibition (% TGI=1−[change of tumor volume in treatment group/change of tumor volume in control group]*100) is used to evaluate anti-tumor efficacy. Statistical significance is evaluated using a one-tailed, two sample t test. P<0.05 is considered statistically significant.

Efficacy Study in Prostate Tumor Xenograft Model.

Immunodeficient mice, such as 4-6 week-old male CB17 severe combined immunodeficiency (SCID) mice, are used for in vivo efficacy studies in accordance with the guidelines approved by IACUC. Parental prostate cancer cells, such as VCaP or LNCaP-AR cells, are implanted subcutaneously into male CB.17.SCID mice ($3-4 \times 10^6$ cells in 50% Matrigel). When the tumor reaches a palpable size of approximately 80 mm$^3$, the tumor-bearing mice are randomly assigned to a vehicle control or compound treatment group (6 or more animals per group). Animals are treated with a compound of the present invention by intraperitoneal injection in an appropriate amount and frequency as can be determined by the skilled artisan without undue experimentation. In one example, mice are treated with 40 mg/kg of a compound of the present invention daily by i.p. injection for two weeks, then 5 days per week thereafter. Subcutaneous tumor volume and mice body weight are measured twice weekly. Tumor volumes are calculated by measuring two perpendicular diameters with calipers (V=(length×width$^2$)/2).

Efficacy Study in Castration-Resistant Prostate Tumor Xenograft Model (VCaP).

Immunodeficient mice, such as 4-6 week-old male CB17 severe combined immunodeficiency (SCID) mice, are used for in vivo efficacy studies in accordance with the guidelines approved by IACUC. Parental prostate cancer cells, such as VCaP cells, are implanted subcutaneously into male CB. 17.SCID mice ($3-4 \times 10^6$ cells in 50% Matrigel). When the tumor reaches a size of approximately 200-300 mm$^3$, the tumor-bearing mice are physically castrated and tumors observed for regression and regrowth to approximately 150 mm$^3$. The tumor-bearing mice are randomly assigned to a vehicle control or compound treatment group (6 or more animals per group). Animals are treated with a compound of the present invention by intraperitoneal injection in an appropriate amount and frequency as can be determined by the skilled artisan without undue experimentation. In one example, mice are treated with 40 mg/kg of a compound of the present invention daily by i.p. injection. Subcutaneous tumor volume and mice body weight are measured twice weekly. Tumor volumes are calculated by measuring two perpendicular diameters with calipers (V=(length×width$^2$)/2).

Efficacy Study in Castration-Resistant Prostate Tumor Xenograft Model (LNCaP-AR).

Immunodeficient mice, such as 4-6 week-old male CB17 severe combined immunodeficiency (SCID) mice, are used for in vivo efficacy studies in accordance with the guidelines approved by IACUC. CB. 17.SCID mice are surgically castrated and allowed to recover for 2-3 weeks before implanting parental prostate cancer cells, such as LNCaP-AR cells, subcutaneously into ($3-4 \times 10^6$ cells in 50% Matrigel). When the tumor reaches a size of approximately 80-100 mm$^3$, the tumor-bearing mice are randomly assigned to a vehicle control or compound treatment group (6 or more animals per group). Animals are treated with a compound of the present invention by intraperitoneal injection in an appropriate amount and frequency as can be determined by the skilled artisan without undue experimentation. In one example, mice are treated with 60 mg/kg of a compound of the present invention daily by i.p. injection for 27 days. Subcutaneous tumor volume and mice body weight are measured twice weekly. Tumor volumes are calculated by measuring two perpendicular diameters with calipers (V=(length×width$^2$)/2).

Cellular Thermal Shift Assay (CETSA).

For the cell lysate CETSA experiments, cultured cells from cell lines (e.g., HEK293, bone marrow samples) are harvested and washed with PBS. The cells are diluted in kinase buffer (KB) (25 mM Tris(hydroxymethyl)-aminomethane hydrochloride (Tris-HCl, pH 7.5), 5 mM beta-glycerophosphate, 2 mM dithiothreitol (DTT), 0.1 mM sodium vanadium oxide, 10 mM magnesium chloride) or in phosphate-buffered saline (PBS) (10 mM phosphate buffer (pH 7.4), 2.7 mM potassium chloride and 137 mM sodium chloride). All buffers are supplemented with Complete protease inhibitor cocktail. The cell suspensions are freeze-thawed three times using liquid nitrogen. The soluble fraction (lysate) is separated from the cell debris by centrifugation at 20000×g for 20 minutes at 4° C. The cell lysates are diluted with appropriate buffer and divided into two aliquots, with one aliquot being treated with drug (e.g., compound of any of Formulas I, II, III, IV, V, VI, IX, and X or pharmaceutically acceptable salts thereof) and the other aliquot with the diluent of the inhibitor (control). After 10-30 minute incubation at room temperature the respective lysates are divided into smaller (50 µL) aliquots and heated individually at different temperatures for 3 minutes followed by cooling for 3 minutes at room temperature. The appropriate temperatures are determined in preliminary CETSA experiments. The heated lysates are centrifuged at 20000×g for 20 minutes at 4° C. in order to separate the soluble fractions from precipitates. The supernatants are transferred to new microtubes and analyzed by sodium dodecyl sulfate polyacrylamide gel electrophoresis (SDS-PAGE) followed by western blot analysis.

For the intact cell experiments the drug-treated cells from the in vitro experiments above are heated as previously described followed by addition of KB (30 µL) and lysed using 2 cycles of freeze-thawing with liquid nitrogen. The soluble fractions are isolated and analyzed by western blot.

For the in vivo mice experiments, lysates of frozen tissues are used. The frozen organs (e.g., liver or kidney) are thawed on ice and briefly rinsed with PBS. The organs are homogenized in cold PBS using tissue grinders followed by 3 cycles of freeze-thawing using liquid nitrogen. Tissue lysates are separated from the cellular debris and lipids. The tissue lysates are diluted with PBS containing protease inhibitors, divided into 50 µL aliquots and heated at different temperatures. Soluble fractions are isolated and analyzed by western blot.

CETSA-Like Dot-Blot Experiments on Purified Proteins.

Purified protein (0.5 µg) is added to the wells of a PCR plate and the volume adjusted to 50 µL by addition of buffer or cell lysates and ligands depending on the experimental setup. The samples are heated for the designated time and temperature in a thermocycler. After heating, the samples are immediately centrifuged for 15 min at 3000×g and filtered using a 0.65 µm Multiscreen HTS 96 well filter plate. 3 µL of each filtrate are blotted onto a nitrocellulose membrane. Primary antibody and secondary conjugate are used for immunoblotting. All membranes are blocked with blocking buffer; standard transfer and western blot protocols recommended by the manufacturers are used. All antibodies are diluted in blocking buffer. The dot-blot is developed. Chemiluminescence intensities are detected and imaged. Raw dot blot images are processed. The background is subtracted and intensities are quantified. Graphs are plotted and fitted using sigmoidal dose-response (variable slope).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:
1. A compound selected from the group consisting of:
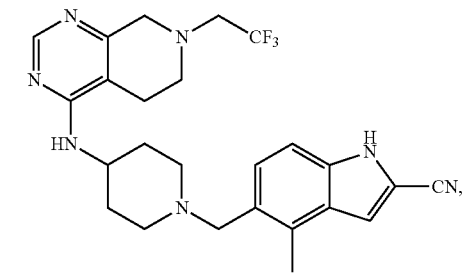
II-1
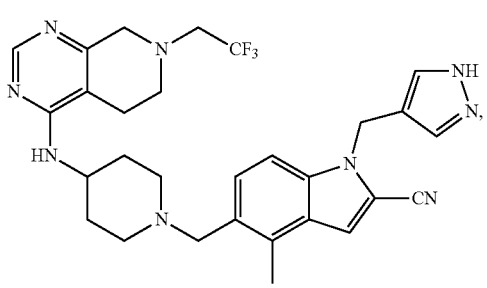
VII-2
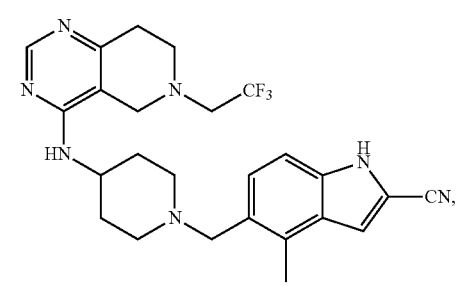
VII-3
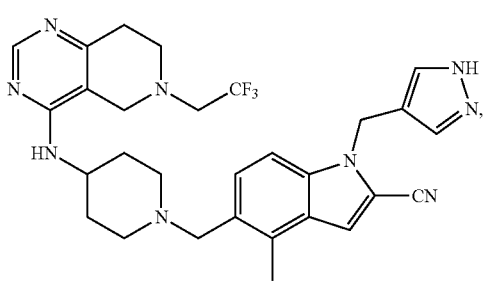
VII-4
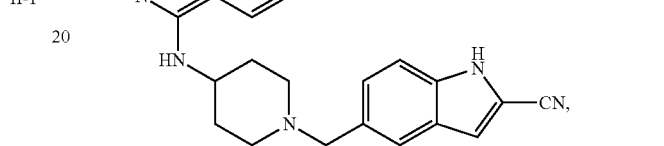
VII-5
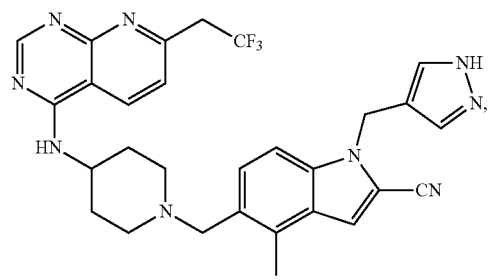
VII-6
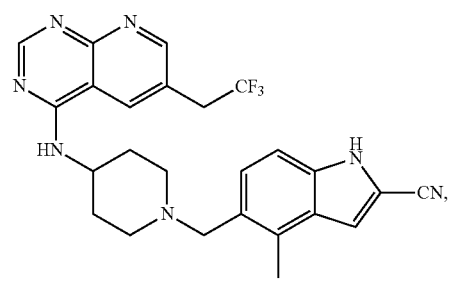
VII-7
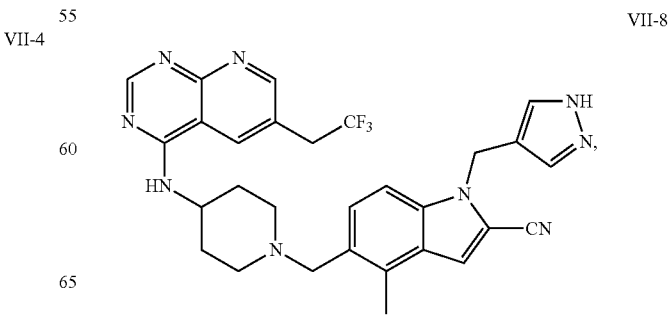
VII-8

VII-9
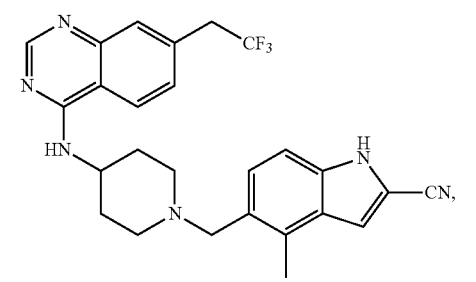
VII-10
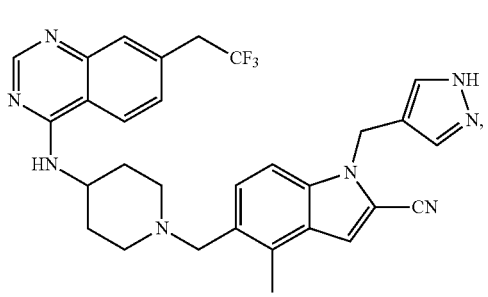
VII-11
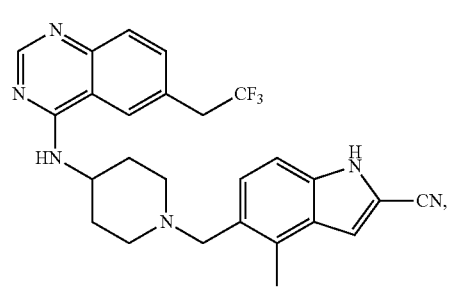
VII-12
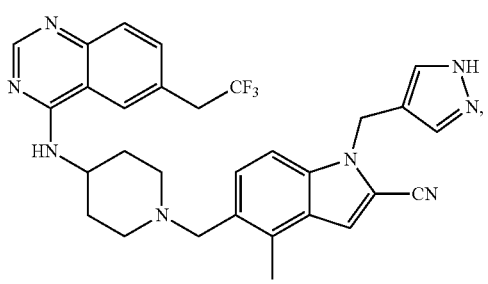
VII-13
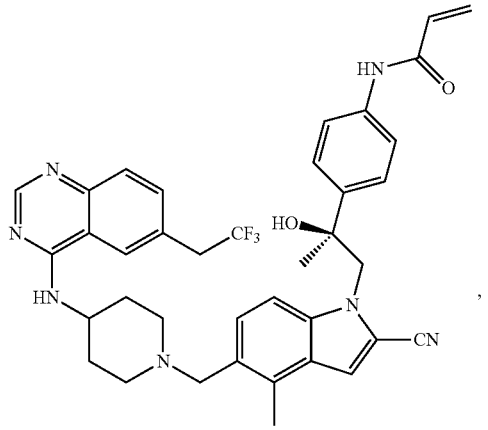
VII-14
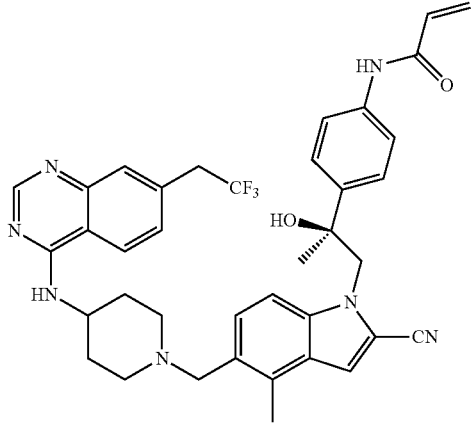
VII-15
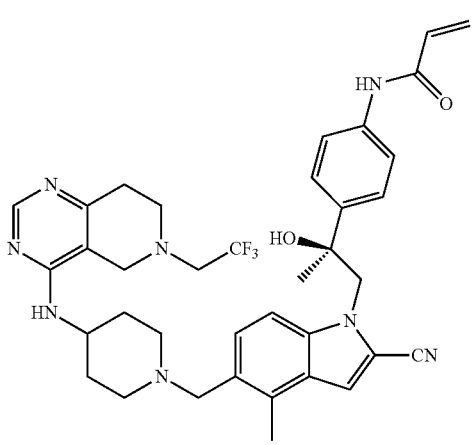
VII-16
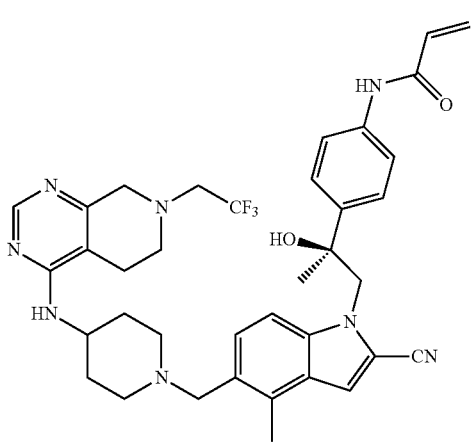
VII-17
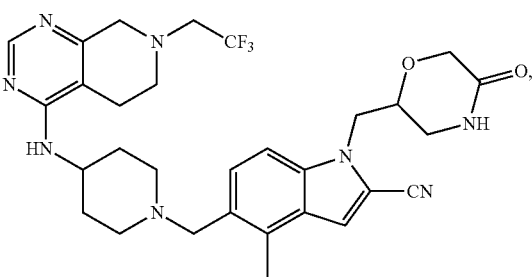

VII-18
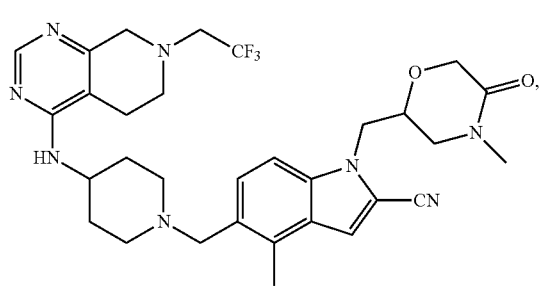
VII-19
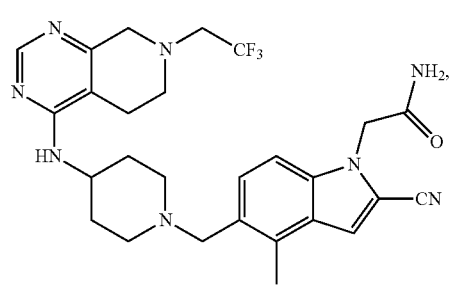
VII-20
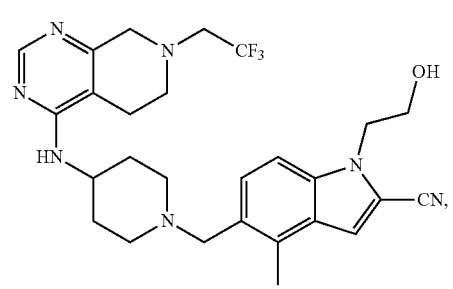
VII-21
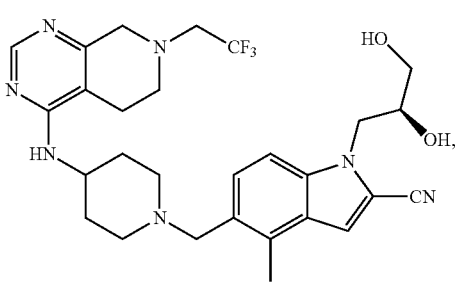
VII-22
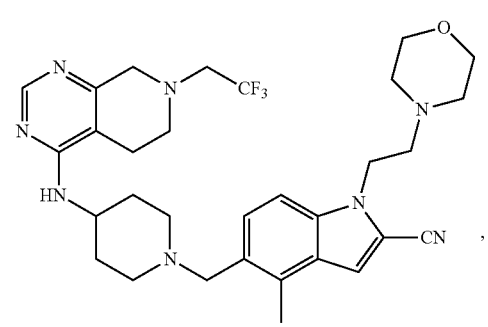
VII-23
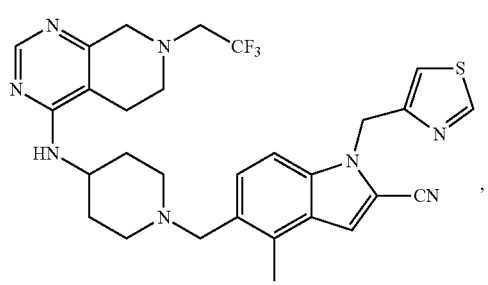
VII-24
VII-25
VII-26
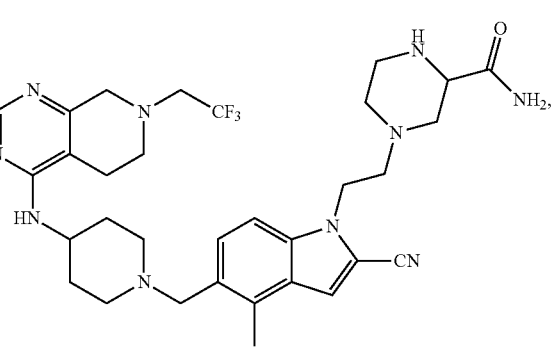
VII-27
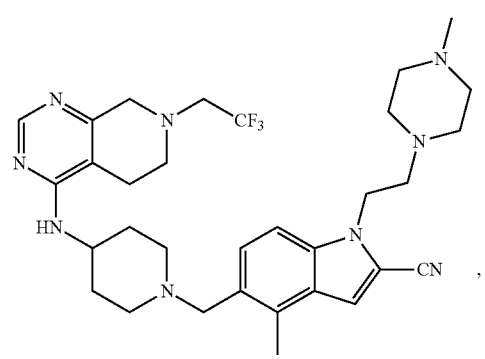

VII-28
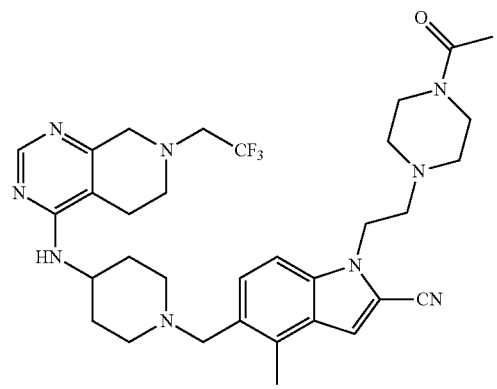
VII-29
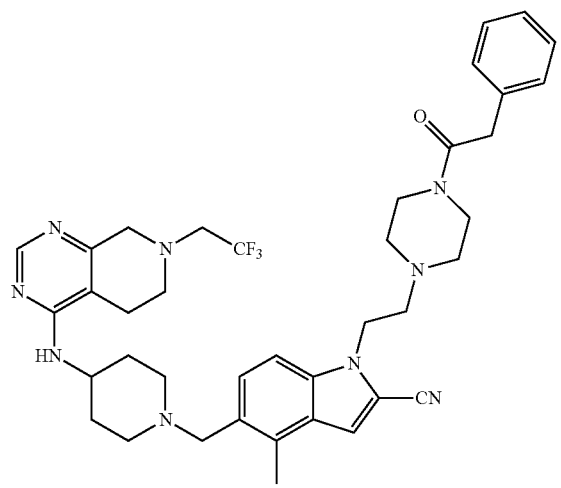
VII-30
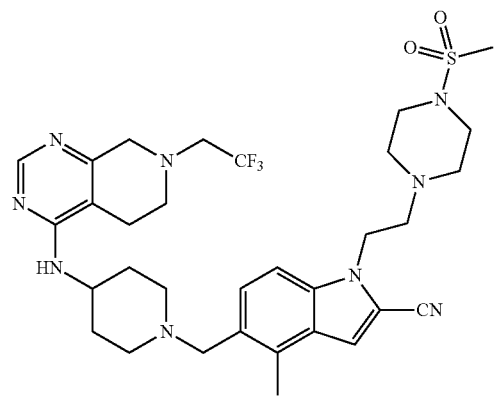
VII-31
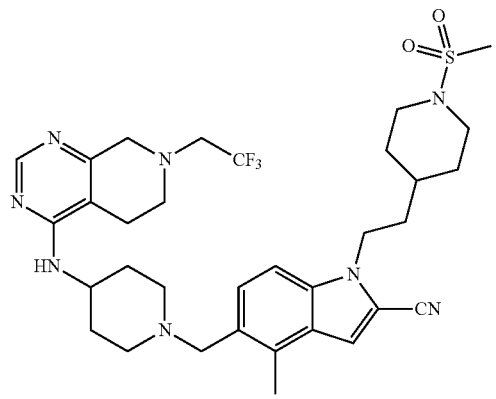
VII-32
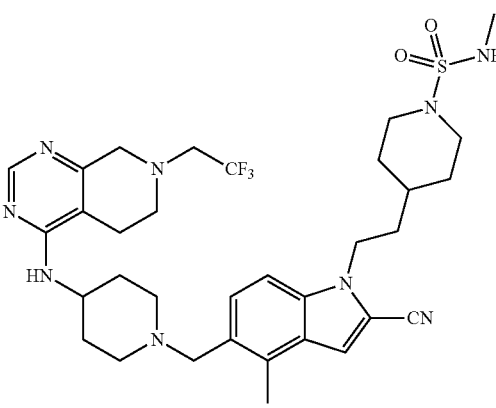
VII-33
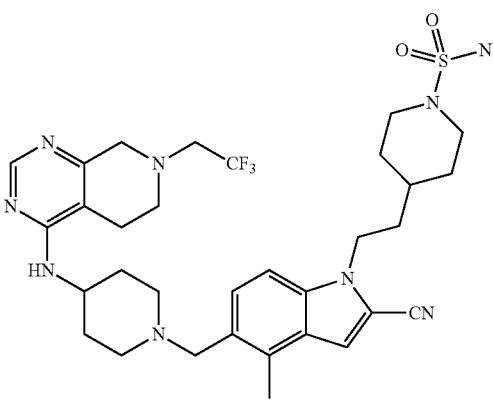
VII-34
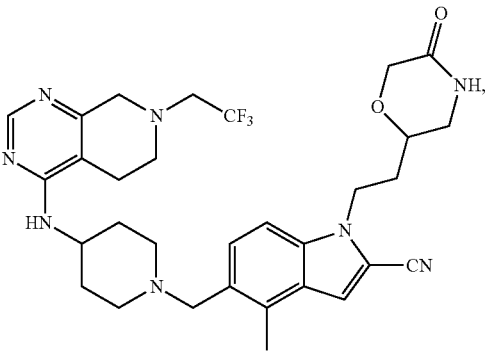

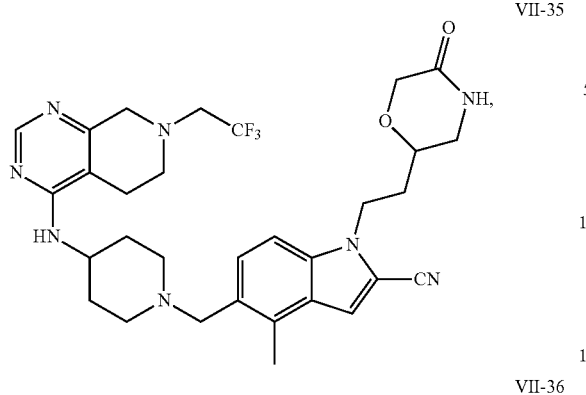
VII-35
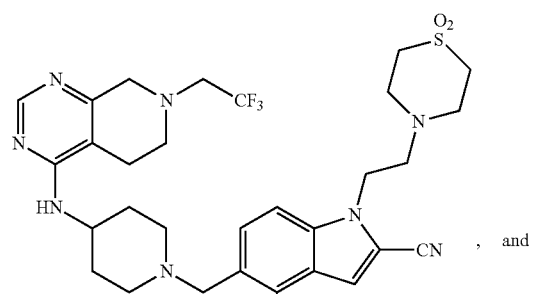
VII-37
, and
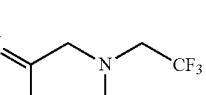
VII-36
,
VII-38
* * * * *